(12) United States Patent
Zhang et al.

(10) Patent No.: US 7,253,342 B2
(45) Date of Patent: Aug. 7, 2007

(54) INCREASED WAX PRODUCTION IN PLANTS

(75) Inventors: Jiyi Zhang, Ardmore, OK (US); Zengyu Wang, Ardmore, OK (US)

(73) Assignee: Samuel Roberts Noble Foundation, Ardmore, OK (US)

( * ) Notice: Subject to any disclaimer, the term of this patent is extended or adjusted under 35 U.S.C. 154(b) by 0 days.

(21) Appl. No.: 11/253,300

(22) Filed: Oct. 18, 2005

(65) Prior Publication Data

US 2006/0107349 A1 May 18, 2006

Related U.S. Application Data

(60) Provisional application No. 60/619,801, filed on Oct. 18, 2004.

(51) Int. Cl.
  A01H 5/00 (2006.01)
  C12N 15/82 (2006.01)
  C12N 5/04 (2006.01)
  C12N 21/00 (2006.01)
  C12N 15/29 (2006.01)

(52) U.S. Cl. .................. 800/298; 435/468; 435/320.1; 435/419; 536/23.1; 536/23.6; 800/281

(58) Field of Classification Search ...................... None
See application file for complete search history.

(56) References Cited

U.S. PATENT DOCUMENTS

2004/0034888 A1  2/2004  Liu et al. .................... 800/289

FOREIGN PATENT DOCUMENTS

WO  WO 03/014327  2/2003

OTHER PUBLICATIONS

Keskin et al. (Protein Science, 13:1043-1055, 2004).*
Guo et al. (PNAS, 101: 9205-9210, 2004).*
Thornton et al. (Nature structural Biology, structural genomics supplement, Nov. 2000).*
Hooker et al. (Plant Physiology, 129:1568-1580, 2002).*
GenBank Accession No. AW775766.
GenBank Accession No. BE124325.
GenBank Accession No. BI310748.
GenBank Accession No. BM814583.
GenBank Accession No. CB893186.
GenBank Accession No. CG963643.
Vogg et al., "Tomato fruit cuticular waxes and their effects on transpiration barrier properties: functional characterization of a mutant deficient in a very-long-chain fatty acid beta-ketoacyl-CoA synthase," *Journal of Experimental Botany*, 55(401): 1401-1410, 2004.
Xia et al., "Cloning and characterization of CER2, an *Arabidopsis* gene that affects cuticular wax accumulation," *Plant Cell*, 8(8):1291-1304, 1996.
Aharoni et al., "The SHINE clade of AP2 domain transcription factors activates wax biosynthesis, alters cuticle properties, and confers drought tolerance when overexpressed in *Arabidopsis*," *Plant Cell*, 16: 2463-2480, 2004.
Broun et al., "WIN1, a transcriptional activator of epidermal wax accumulation in *Arabidopsis*," *Proc. Natl. Acad. Sci. USA*, 101:4706-4711, 2004.
Databank Accession No. AtTC261112.
Databank Accession No. AtTC262267.
Databank Accession No. CTC28125.
Databank Accession No. CTC37888.
Databank Accession No. CTC38239.
Databank Accession No. GmTC215663.
Databank Accession No. GmTC215664.
Databank Accession No. GmTC225042.
Databank Accession No. GmTC225047.
Databank Accession No. GmTC228532.
Databank Accession No. LeTC137279.
Databank Accession No. LeTC154153.
Databank Accession No. LjTC16026.
Databank Accession No. LsTC8978.
Databank Accession No. PplTC29328.
Databank Accession No. PplTC29329.
Databank Accession No. SbTC103215.
Databank Accession No. StTC102572.
Databank Accession No. StTC104330.
Databank Accession No. VvTC45892.
Databank Accession No. ZmTC270551.
Fujimoto et al., "*Arabidopsis* ethylene-responsive element binding factors act as transcriptional activators or repressors of GCC box-mediated gene expression," *Plant Cell*, 12:393-405, 2000.
Gilmour et al., "Overexpression of the *Arabidopsis* CBF3 transcriptional activator mimics multiple biochemical changes associated with cold acclimation," *Plant Physiol.*, 124:1854-1865, 2000.
Gu et al., "Tomato transcription factors pti4, pti5, and pti6 activate defense responses when expressed in *Aarabidopsis*," *Plant Cell*, 14:817-831, 2002.
Haake et al., "Transcription factor CBF4 is a regulator of drought adaptation in *Arabidopsis*," *Plant Physiol.*, 130, 639-648, 2002.
Jaglo-Ottosen et al., "*Arabidopsis* CBF1 overexpression induces COR genes and enhances freezing tolerance," *Science*, 280:104-106, 1998.
Jefferson, "Genetic varioation for epicuticular wax prodution in altai wildrye populations that differ in glaucousness," *Crop Sci.*, 34:367-371, 1994.
Kasuga et al., "Improving plant drought, salt, and freezing tolerance by gene transfer of a single stress-inducible transcription factor," *Nat. Biotechnol.*, 17:287-291, 1999.

(Continued)

Primary Examiner—David H. Kruse
Assistant Examiner—Vinod Kumar
(74) *Attorney, Agent, or Firm*—Fulbright & Jaworski L.L.P.

(57) ABSTRACT

The invention provides genes that activate wax biosynthesis in plants. Also provided are constructs comprising these sequences, plants transformed therewith and methods of use thereof. The invention allows the modification of plants for increased wax production, particularly in leaves. The inventors have demonstrated increased drought tolerance in connection with increased leaf wax production engineered in plants.

17 Claims, 18 Drawing Sheets

OTHER PUBLICATIONS

Liu et al., "Two transcription factors, DREB1 and DREB2, with an EREBP/AP2 DNA binding domain separate two cellular signal transduction pathways in drought- and low-temperature-responsive gene expression, respectively, in *Arabidopsis,*".*Plant Cell*, 10:1391-1406, 1998.

Moose and Sisco, "Glossy15, an APETALA2-like gene from maize that regulates leaf epidermal cell identity," *Genes Dev.*, 10:3018-3027, 1996.

Novillo et al., "CBF2/DREB1C is a negative regulator of CBF1/DREB1B and CBF3/DREB1A expression and plays a central role in stress tolerance in *Arabidopsis,*" *Proc. Natl. Acad. Sci. USA*, 101(11):3985-3990, 2004.

Ohme-Takagi et al., "Ethylene-inducible DNA binding proteins that interact with an ethylene-responsive element," *Plant Cell*, 7:173-182, 1995.

Okamuro et al., "The AP2 domain of APETALA2 defines a large new family of DNA binding proteins in *Arabidopsis,*" *Proc. Natl. Acad. Sci. USA*, 94:7076-7081, 1997.

Shinozaki et al., "Regulatory network of gene expression in the drought and cold stress responses," *Curr. Opin. Plant Biol.*, 6:410-417, 2003.

Stockinger et al., "*Arabidopsis thaliana* CBF1 encodes an AP2 domain-containing transcriptional activator that binds to the C-repeat/DRE, a cis-acting DNA regulatory element that stimulates transcription in response to low temperature and water deficit," *Proc. Natl. Acad. Sci. USA*, 94:1035-1040, 1997.

Thomashow, "Plant cold acclimation: freezing tolerance genes and regulatory mechanisms," *Annu. Rev. Plant Physiol. Plant Mol. Biol.*, 50, 571-599, 1999.

Zhang et al., "Overexpression of WXP1, a putative Medicago truncatula AP2 domain-containing transcription factor gene, increases cuticular wax accumulation and enhances drought tolerance in transgenic alfalfa (Medicago sativa)," *Plant J.*, 42:689-707, 2005.

\* cited by examiner

FIG. 1

SEQUENCE LISTING

<160> NUMBER OF SEQ ID NOS: 46

<210> SEQ ID NO 1
<211> LENGTH: 371
<212> TYPE: PRT
<213> ORGANISM: Medicago truncatula

<400> SEQUENCE: 1

```
Met Asp Phe Phe Asn Asn Ser Gln Asp Pro Phe Asn Gly Glu Leu Met
  1               5                  10                  15

Glu Val Leu Glu Pro Phe Met Lys Ser Ser Ile Ser Pro Ser Ser
             20                  25                  30

Pro Pro Ser Leu Asn Ser His Leu Pro Ser Thr Ser Ser Ser Ser
         35                  40                  45

Ser Pro Phe Tyr Ser Ser Thr Pro Pro Phe Phe Gln Pro Ser Phe Ser
         50                  55                  60

Pro Gln Ser Ser Ser Ser Ser Ser Phe Pro Pro Gln Pro Asn Phe
 65                  70                  75                  80

Tyr Thr Glu Asn Gly Tyr Cys Ser Ser Met Met Asn Tyr Gln Phe Pro
                 85                  90                  95

Ser Leu Gly Asn Ser Ser Thr Ser Gln Asn Asn Phe Ile Gly Phe Glu
                100                 105                 110

Gln Pro Gln Gln Pro Asn Ser Val Ile Gly Leu Asn Thr Leu Thr Pro
            115                 120                 125

Ser Gln Ile Asn Gln Ile Gln Ala Gln Ile Gln Phe Gln Gln Thr Gln
    130                 135                 140

Ser Asn Asn Ser Ser Leu Asn Phe Leu Gly Pro Lys Pro Ile Pro Met
145                 150                 155                 160

Lys Gln Pro Gly Val Pro Pro Lys Pro Thr Lys Leu Tyr Arg Gly Val
                165                 170                 175

Arg Gln Arg His Trp Gly Lys Trp Val Ala Glu Ile Arg Leu Pro Lys
            180                 185                 190

Asn Arg Thr Arg Leu Trp Leu Gly Thr Phe Asp Thr Ala Glu Glu Ala
        195                 200                 205

Ala Leu Ala Tyr Asp Arg Ala Ala Tyr Arg Leu Arg Gly Asp Phe Ala
    210                 215                 220

Arg Leu Asn Phe Pro Asn Met Lys Asp Gln Gln Gln Gly Gly Met Phe
225                 230                 235                 240

Gly Glu Phe Lys Val Leu His Ser Ser Ile Asp Ala Lys Leu Asp Ala
                245                 250                 255

Ile Cys Glu Ser Leu Gly Asn Asn Asn Ser Ser Asp Asn Val Lys Asn
            260                 265                 270

Lys Lys Gln Gly Lys Gly Ser Lys Lys Ser Leu Lys Lys Glu Val Glu
        275                 280                 285

Ala Gln Pro Gln Pro Gln Pro Leu Val Val Glu Asn Asn Asn Asp
    290                 295                 300

Asp Asn Asn Asn Thr Asn Thr Asn Lys Val Val Glu Cys Gly Ser
305                 310                 315                 320

Ser Leu Ser Ser His Ser Glu Gly Gly Ser Asp Ser Ser Pro Leu
                325                 330                 335

Ser Asp Leu Thr Phe Gly Glu Phe Ala Glu Pro Gln Trp Glu Asn Gly
            340                 345                 350

Phe Glu Gln Phe Asn Leu Gln Lys Phe Pro Ser Tyr Glu Ile Asp Trp
```

```
                355                 360                 365
Ala Ser Leu
    370

<210> SEQ ID NO 2
<211> LENGTH: 1116
<212> TYPE: DNA
<213> ORGANISM: Medicago truncatula

<400> SEQUENCE: 2
atggatttct tcaacaattc acaagatcca ttcaatggtg agttaatgga agttcttgaa      60
ccttttatga agagttcttc catttctcct tcatcacccc cttctctaaa ttcacacctc     120
ccttcaactt cttcttcatc atcatcacct ttttactctt ctacaccccc cttttttcaa     180
ccttctttct ctcctcaatc ttcttcttct tcttcttctt ttcctccaca gcccaatttc     240
tacacagaaa atggttactg ttcatccatg atgaattacc aatttccttc tttaggtaat     300
tcatcaacta gccaaaataa tttcattggc tttgaacaac cacaacaacc aaattctgtt     360
attgggctaa acaccttaac cccatctcaa attaaccaga tccaagccca gatccagttt     420
caacaaaccc aaagtaacaa ctcaagcttg aactttcttg ggcctaagcc catcccaatg     480
aaacagcctg gtgtacctcc aaagcccaca aagctttata gaggtgtaag gcaaagacat     540
tggggaaaat gggttgctga gataagacta cccaagaata gaacaaggct ttggcttggt     600
acttttgaca ctgctgaaga agctgctttg gcttatgata gagctgctta tagattaaga     660
ggtgattttg ctagacttaa tttcccaaac atgaaagacc aacaacaagg tggtatgttt     720
ggtgagttta aggttttgca ttcatctatt gatgctaaac ttgatgctat ttgtgagagt     780
ttaggtaaca acaatagtag tgataatgtc aagaacaaga acaagggaa gggttcaaag      840 aagagtttga agaaagaggt tgaagctcaa cctcaacctc aaccattggt tgttgttgaa     900
aataataatg atgataacaa caataccaat accaacaagg ttgttgttga atgtggttct     960
tctttgtctt cacatagtga aggtggttct gatgattctt ctccacttc tgatcttact    1020 tttggtgaat tgctgagcc acaatgggaa atggttttg aacaatttaa tttgcagaaa    1080
tttccttctt atgagattga ttgggcttct ctttga                             1116

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
ggtaccatgg atttcttcaa ca                                                22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
aaccggtcac caaattcatc ca                                                22

<210> SEQ ID NO 5
```

<211> LENGTH: 340
<212> TYPE: PRT
<213> ORGANISM: Medicago truncatula

<400> SEQUENCE: 5

```
Met Ala Ala Met Met Asn Tyr Tyr Ser Asn Met Gln Gln Phe Gln Phe
  1               5                  10                  15

His Asp Ser Asp Pro Phe Arg Gly Glu Leu Met Glu Val Leu Glu Pro
             20                  25                  30

Phe Ile Lys Ser Pro Ser Ser Thr Ser Thr Ser Pro Ser Ser Ser Thr
         35                  40                  45

Pro Ser Pro Ser Tyr Ser Ser Ser Leu Ser Ser Pro Ser Phe Tyr Thr
 50                  55                  60

Glu Gln Asn Phe Ile Gly Phe Ala Gln Pro Ser Ser Ser Phe Ser Ser
 65                  70                  75                  80

Pro Ser Leu Leu Gly Leu Asn His Leu Thr Pro Ser Gln Ile Asn Gln
             85                  90                  95

Ile Gln Val Gln Ile Gln Gln Asn Phe Thr Met Gln His Gln Gln
            100                 105                 110

Ile Gln Gln Gln Gln Arg Cys Leu Ser Asn Thr Leu Ser Phe Leu
        115                 120                 125

Ser Pro Lys Ser Ile Pro Met Lys His Val Gly Gly Ser Ser Val Ser
130                 135                 140

Lys Pro Thr Lys Leu Tyr Arg Gly Val Arg Gln Arg His Trp Gly Lys
145                 150                 155                 160

Trp Val Ala Glu Ile Arg Leu Pro Lys Asn Arg Thr Arg Leu Trp Leu
                165                 170                 175

Gly Thr Phe Asp Thr Ala Glu Glu Ala Ala Leu Ala Tyr Asp Lys Ala
            180                 185                 190

Ala Tyr Lys Leu Arg Gly Asp Phe Ala Arg Leu Asn Phe Pro Asn Leu
        195                 200                 205

Lys His Gln Gly Ser Ile Ile Gly Gly Glu Phe Gly Glu Phe Lys Pro
    210                 215                 220

Leu Pro Ser Ser Val Asp Ala Lys Leu Gln Ala Ile Cys Glu Gly Leu
225                 230                 235                 240

Ala Glu Met Gln Lys Gln Gly Lys Ala Glu Lys Pro Lys Lys Met Pro
                245                 250                 255

Ala Ser Lys Ala Lys Ala Ser Ser Lys Val Val Ser Lys Glu Ser Val
            260                 265                 270

Asp Asp Leu Lys Lys Asp Ser Glu Pro Glu Glu Cys Cys Lys Val Glu
        275                 280                 285

Ala Val Ser Val Ile Thr Glu Ser Glu Gly Ser Glu Gly Ser Ser Pro
    290                 295                 300

Leu Ser Asp Leu Thr Phe Gly Asp Val Gly Glu Pro Gln Trp Glu Gly
305                 310                 315                 320

Asp Ser Glu Asn Phe Asn Leu Leu Lys Tyr Pro Ser Tyr Glu Ile Asp
                325                 330                 335

Trp Asp Ser Leu
            340
```

<210> SEQ ID NO 6
<211> LENGTH: 1023
<212> TYPE: DNA
<213> ORGANISM: Medicago truncatula

<400> SEQUENCE: 6

```
atggcagcta tgatgaatta ttacagtaac atgcaacagt ttcaatttca tgactcagat    60
ccatttagag gtgaattaat ggaagttctt gaaccttta tcaaaagtcc ttcttcaact   120
tcaacttcac cttcatcttc aacaccatca ccttcttatt cttcttctct ctcttcacct   180
tctttctaca cagagcaaaa cttcataggc tttgctcaac catcttcttc tttttcttct   240
ccttctcttc ttggtctcaa ccacttgaca ccatcacaaa tcaaccaaat ccaagtacaa   300
atccaacaac aaaacttcac catgcaacat caacaaattc aacagcaaca caacgttgt    360 cttagtaaca ctttgagttt tcttagtcca aagtcaattc ctatgaagca tgtgggtggt   420
agtagtgttt caaacccac aaagctatac agaggagtga gacaaaggca ctggggaaaa    480
tgggttgctg agataagact acctaagaac cgaacaagat tatggcttgg tactttgac    540 acagctgaag aagcagcttt ggcttatgat aaagctgctt ataagctacg tggtgacttt   600
gctaggctaa attttccaaa tttgaaacac caaggttcaa ttattggtgg tgaatttggt   660
gagtttaaac ctcttccttc ttctgttgat gctaagcttc aagctatttg tgaaggttta   720
gctgagatgc agaaacaggg gaaggctgag aagcctaaga gatgccggc gtcgaaggcg    780 aaagcctctt caaggtggt ttctaaggag tctgttgatg atttgaagaa ggattcagag     840
ccagaggagt gttgtaaggt tgaagcagtt tcagtgatta ctgagagtga aggttctgaa   900
ggttcttcac cactttcaga tcttactttt ggtgatgttg gtgaaccaca gtgggagggt   960
gattcagaaa attttaattt gctcaagtac ccttcttatg agattgattg ggattctctg  1020
tga                                                                1023
```

<210> SEQ ID NO 7
<211> LENGTH: 334
<212> TYPE: PRT
<213> ORGANISM: Arabidopsis thaliana

<400> SEQUENCE: 7

```
Met Ala Ala Met Asn Leu Tyr Thr Cys Ser Arg Ser Phe Gln Asp
  1               5                  10                  15

Ser Gly Gly Glu Leu Met Asp Ala Leu Val Pro Phe Ile Lys Ser Val
             20                  25                  30

Ser Asp Ser Pro Ser Ser Ser Ala Ala Ser Ala Ser Ala Phe Leu
         35                  40                  45

His Pro Ser Ala Phe Ser Leu Pro Pro Leu Pro Gly Tyr Tyr Pro Asp
     50                  55                  60

Ser Thr Phe Leu Thr Gln Pro Phe Ser Tyr Gly Ser Asp Leu Gln Gln
 65                  70                  75                  80

Thr Gly Ser Leu Ile Gly Leu Asn Asn Leu Ser Ser Gln Ile His
                 85                  90                  95

Gln Ile Gln Ser Gln Ile His His Pro Leu Pro Pro Thr His His Asn
            100                 105                 110

Asn Asn Asn Ser Phe Ser Asn Leu Leu Ser Pro Lys Pro Leu Leu Met
        115                 120                 125

Lys Gln Ser Gly Val Ala Gly Ser Cys Phe Ala Tyr Gly Ser Gly Val
    130                 135                 140

Pro Ser Lys Pro Thr Lys Leu Tyr Arg Gly Val Arg Gln Arg His Trp
145                 150                 155                 160

Gly Lys Trp Val Ala Glu Ile Arg Leu Pro Arg Asn Arg Thr Arg Leu
                165                 170                 175

Trp Leu Gly Thr Phe Asp Thr Ala Glu Glu Ala Ala Leu Ala Tyr Asp
```

```
                   180               185               190
Lys Ala Ala Tyr Lys Leu Arg Gly Asp Phe Ala Arg Leu Asn Phe Pro
            195                 200                 205

Asn Leu Arg His Asn Gly Ser His Ile Gly Gly Asp Phe Gly Glu Tyr
        210                 215                 220

Lys Pro Leu His Ser Ser Val Asp Ala Lys Leu Glu Ala Ile Cys Lys
225                 230                 235                 240

Ser Met Ala Glu Thr Gln Lys Gln Asp Lys Ser Thr Lys Ser Ser Lys
                245                 250                 255

Lys Arg Glu Lys Lys Val Ser Ser Pro Asp Leu Ser Glu Lys Val Lys
            260                 265                 270

Ala Glu Glu Asn Ser Val Ser Ile Gly Gly Ser Pro Pro Val Thr Glu
        275                 280                 285

Phe Glu Glu Ser Thr Ala Gly Ser Ser Pro Leu Ser Asp Leu Thr Phe
        290                 295                 300

Ala Asp Pro Glu Glu Pro Gln Trp Asn Thr Phe Ser Leu Glu
305                 310                 315                 320

Lys Tyr Pro Ser Tyr Glu Ile Asp Trp Asp Ser Ile Leu Ala
                325                 330
```

<210> SEQ ID NO 8
<211> LENGTH: 1005
<212> TYPE: DNA
<213> ORGANISM: Arabidopsis thaliana

<400> SEQUENCE: 8

```
atggcagctg ctatgaattt gtacacttgt agcagatcgt ttcaagactc tggtggtgaa      60
ctcatggacg cgcttgtacc ttttatcaaa agcgtttccg attctccttc ttcttcttct     120
gcagcgtctg cgtctgcgtt tcttcacccc tctgcgtttt ctctccctcc tctcccggt      180
tattacccgg attcaacgtt cttgacccaa ccgttttcat acgggtcgga tcttcaacaa     240
accgggtcat taatcggact caacaacctc tcttcttctc agatccacca gatccagtct     300
cagatccatc atcctcttcc tccgacgcat acaacaacaa caactctttt ctcgaatctt     360
ctcagcccaa agccgttact gatgaagcaa tctggagtcg ctggatcttg tttcgcttac     420
ggttcaggtg ttccttcgaa gccgacgaag ctttacagag gtgtgaggca acgtcactgg     480
ggaaaatggg tggctgagat ccgtttgccg agaaatcgga ctcgtctctg gcttgggact     540
tttgacacgg cggaggaagc tgcgttggcc tatgataagg cggcgtacaa gctgcgcggc     600
gatttcgccc ggcttaactt ccctaaccta cgtcataacg gatctcacat cggaggcgat     660
ttcggtgaat ataaacctct tcactcctca gtcgacgcta agcttgaagc tatttgtaaa     720
agcatggcgg agactcagaa acaggacaaa tcgacgaaat catcgaagaa acgtgagaag     780
aaggtttcgt cgccagatct atcggagaaa gtgaaggcgg aggagaattc ggtttcgatc     840
ggtggatctc caccggtgac ggagtttgaa gagtccaccg ctggatcttc gccgttgtcg     900
gacttgacgt tcgctgaccc ggaggagccg ccgcagtgga acgagacgtt ctcgttggag     960
aagtatccgt cgtacgagat cgattgggat tcgattctag cttag                    1005
```

<210> SEQ ID NO 9
<211> LENGTH: 261
<212> TYPE: PRT
<213> ORGANISM: Arabidopsis thaliana

<400> SEQUENCE: 9

```
Met Thr Thr Ser Met Asp Phe Tyr Ser Asn Lys Thr Phe Gln Gln Ser
 1               5                  10                  15

Asp Pro Phe Gly Gly Glu Leu Met Glu Ala Leu Leu Pro Phe Ile Lys
                20                  25                  30

Ser Pro Ser Asn Asp Ser Ser Ala Phe Ala Phe Ser Leu Pro Ala Pro
            35                  40                  45

Ile Ser Tyr Gly Ser Asp Leu His Ser Phe Ser His His Leu Ser Pro
        50                  55                  60

Lys Pro Val Ser Met Lys Gln Thr Gly Thr Ser Ala Ala Lys Pro Thr
 65              70                  75                  80

Lys Leu Tyr Arg Gly Val Arg Gln Arg His Trp Gly Lys Trp Val Ala
                 85                  90                  95

Glu Ile Arg Leu Pro Arg Asn Arg Thr Arg Leu Trp Leu Gly Thr Phe
                100                 105                 110

Asp Thr Ala Glu Glu Ala Ala Leu Ala Tyr Asp Lys Ala Ala Tyr Lys
            115                 120                 125

Leu Arg Gly Asp Phe Ala Arg Leu Asn Phe Pro Asp Leu Arg His Asn
130                 135                 140

Asp Glu Tyr Gln Pro Leu Gln Ser Ser Val Asp Ala Lys Leu Glu Ala
145                 150                 155                 160

Ile Cys Gln Asn Leu Ala Glu Thr Thr Gln Lys Gln Val Arg Ser Thr
                165                 170                 175

Lys Lys Ser Ser Arg Lys Arg Ser Ser Thr Val Ala Val Lys Leu
                180                 185                 190

Pro Glu Glu Asp Tyr Ser Ser Ala Gly Ser Ser Pro Leu Leu Thr Glu
            195                 200                 205

Ser Tyr Gly Ser Gly Gly Ser Ser Ser Pro Leu Ser Glu Leu Thr Phe
210                 215                 220

Gly Asp Thr Glu Glu Glu Ile Gln Pro Pro Trp Asn Glu Asn Ala Leu
225                 230                 235                 240

Glu Lys Tyr Pro Ser Tyr Glu Ile Asp Trp Asp Ser Ile Leu Gln Cys
                245                 250                 255

Ser Ser Leu Val Asn
            260
```

<210> SEQ ID NO 10
<211> LENGTH: 786
<212> TYPE: DNA
<213> ORGANISM: Arabidopsis thaliana

<400> SEQUENCE: 10

```
atgacaactt ctatggattt ttacagtaac aaaacgtttc aacaatctga tccattcggt    60
ggtgaattaa tggaagcgct tttacctttt atcaaaagcc cttccaacga ttcatccgcg   120
tttgcgttct ctctacccgc tccaatttca tacgggtcgg atctccactc attttctcac   180
catcttagtc ctaaaccggt ctcaatgaaa caaaccggta cttccgcggc taaaccgacg   240
aagctataca gaggagtgag acaacgtcac tggggaaaat gggtggctga gattcgttta   300
ccgaggaatc gaactcgact ttggctcgga acattcgaca cggcggagga agctgcttta   360
gcttatgaca aggcggcgta taagctccga ggagattttg cgcggcttaa tttccctgat   420
ctccgtcata cgacgagta tcaacctctt caatcatcag tcgacgctaa gcttgaagct   480
atttgtcaaa acttagctga gacgacgcag aaacaggtga gatcaacgaa gaagtcttct   540
tctcggaaac gttcatcaac cgtcgcagtg aaactaccgg aggaggacta ctctagcgcc   600
```

```
ggatcttcgc cgctgttaac ggagagttat ggatctggtg gatcttcttc gccgttgtcg    660
gagctgacgt ttggtgatac ggaggaggag attcagccgc cgtggaacga gaacgcgttg    720
gagaagtatc cgtcgtacga gatcgattgg gattcgattc ttcagtgttc gagtcttgta    780
aattag                                                                786
```

<210> SEQ ID NO 11
<211> LENGTH: 352
<212> TYPE: PRT
<213> ORGANISM: Gossypium hirsutum

<400> SEQUENCE: 11

```
Met Ala Ala Thr Met Asp Phe Cys Ser Ser Ser Asp Ile Tyr Gly
 1               5                  10                  15

Gly Glu Leu Met Glu Ala Leu Glu Pro Phe Met Lys Ser Ala Ser Ser
             20                  25                  30

Ser Ser Ser Ser Ser Pro Ser Pro Ser Pro Ser Ser Tyr Ser
             35                  40                  45

Pro Ser Pro Ser Pro Ser Pro Ser Thr Ser Tyr Leu Ser Phe
     50                  55                  60

Ser Ser Ser Gln Thr Gln Pro Asn Phe Tyr Ala Asp Gly Cys Cys Tyr
 65                  70                  75                  80

Ser Pro Ala Val Asp Gln Phe Leu Gly Val Gln Gln Pro Gln Leu Gly
                 85                  90                  95

Ser Thr Ile Gly Leu Asn Asn Leu Thr Gln Ala Gln Ile Asn Gln Ile
                100                 105                 110

Gln Ala Gln Phe Leu Phe Gln Asn Asn Gln Pro Ser Tyr Leu Tyr Gln
            115                 120                 125

Asn Pro Gln Leu Asn Ala Asn Pro Asn Thr Asn His Met Leu Ser Phe
130                 135                 140

Leu Gly Pro Lys Pro Val Pro Met Lys Gln Met Gly Ser Pro Pro Lys
145                 150                 155                 160

Pro Thr Lys Leu Tyr Arg Gly Val Arg Gln Arg His Trp Gly Lys Trp
                165                 170                 175

Val Ala Glu Ile Arg Leu Pro Lys Asn Arg Thr Arg Leu Trp Leu Gly
            180                 185                 190

Thr Phe Asp Thr Ala Glu Glu Ala Ala Leu Ala Tyr Asp Lys Ala Ala
        195                 200                 205

Tyr Lys Leu Arg Gly Asp Phe Ala Arg Leu Asn Phe Pro Asn Leu Arg
210                 215                 220

His Gln Gly Ser His Ile Gly Gly Asp Phe Gly Glu Tyr Lys Pro Leu
225                 230                 235                 240

His Ser Ser Val Asp Ala Lys Leu Gln Ala Ile Cys Glu Ser Leu Glu
                245                 250                 255

Leu Asn Gln Lys Gln Gly Asn Asn Asn Lys Lys Lys Ser Ser Lys
            260                 265                 270

Glu Asn Lys Val Gln Leu Ala Glu Pro Glu Glu Lys Thr Val Lys Val
        275                 280                 285

Glu Asn Ser Pro Ser Ser Leu Ser Pro Val Leu Ser Glu Asn Glu Gly
    290                 295                 300

Ser Thr Glu Ser Ser Pro Leu Ser Asp Leu Thr Phe Ser Asp Phe Asn
305                 310                 315                 320

Glu Gln Pro Trp Pro Glu Val Val Thr Ser Ser Glu Ser Phe Met Leu
                325                 330                 335
```

```
Ser Lys Tyr Pro Ser Tyr Glu Ile Asp Trp Asp Ser Ile Leu Lys Ala
        340                 345                 350
```

<210> SEQ ID NO 12
<211> LENGTH: 1059
<212> TYPE: DNA
<213> ORGANISM: Gossypium hirsutum

<400> SEQUENCE: 12

```
atggcagcta caatggattt ctgtagtagc agttcagata tatatggtgg agagttgatg      60
gaagcactcg aacctttat gaaaagtgct tcttcctctt cctcttcttc cccttcccct     120
tctccttccc cttcttctta ttctccctct ccttctcctt ctccttctcc ttctacttca    180
tacctctctt tctcttcttc ccaaacacaa cccaattttt acgcagatgg ttgttgttat    240
tccccagcag ttgatcaatt tttaggtgtt cagcagcctc aacttggttc aaccattggg    300
ctaaacaact taaccaagc tcagatcaac caaattcagg ctcaattcct cttccagaac     360
aatcaaccaa gctaccttta ccaaaatcct caacttaacg ccaaccccaa caccaaccac    420
atgctcagct ttcttggtcc aagccagtc ccgatgaaac agatgggttc accaccaaaa     480
cccaccaagc tctacagggg agttaggcaa cgtcactggg gaaaatgggt cgctgagatc    540
cggctaccta gaaccggac acgtctttgg ttaggcactt tcgatacagc cgaggaagca    600
gccttggctt atgataaagc agcctataaa cttaggggtg attttgcgag actcaacttc    660
cctaaccttc gtcaccaagg ttcccatatc ggtggcgact cggtgaata caagcctttg    720
cattcctctg ttgatgctaa gcttcaagct atctgtgaaa gtttggaact caaccaaaag    780
caagggaaca acaacaagaa gaagaaatca tcgaaggaga acaaagtcca attggctgag    840
cctgaggaaa agacagtgaa ggtggagaac tcccctcat ctttatctcc ggttctgtcg     900
gagaatgagg ggtcgacaga atcttcacct ttgtcggatc ttaccttctc ggacttcaac    960
gagcagccat ggcctgaagt tgttacttcc tcggagtctt tatgttgtc caaatacccca    1020
tcatatgaga tcgattggga ttctattcta aaagcttag                         1059
```

<210> SEQ ID NO 13
<211> LENGTH: 332
<212> TYPE: PRT
<213> ORGANISM: Gossypium hirsutum

<400> SEQUENCE: 13

```
Met Ala Ala Val Ile Asp Met Tyr Asn Ser Ser Arg Asn Ser Val Phe
  1               5                  10                  15

Tyr Asp Pro Leu Arg Glu Glu Leu Met Lys Ala Leu Glu Pro Phe Met
                 20                  25                  30

Lys Ser Ala Ser Ser Ser Ser Ser Pro Leu Gln Pro Asn Leu Tyr Pro
             35                  40                  45

Glu Tyr Cys Ser Pro Leu Asn Ser Ser Thr His Leu Phe Ser Asn His
         50                  55                  60

Gly Phe Ser Asn Tyr Asn Lys Asn Met Leu Gly Phe Glu Gln Thr Gly
 65                  70                  75                  80

Ser Ser Leu Gly Leu Asn Gln Leu Thr Pro Ser Gln Ile Leu Gln Ile
                 85                  90                  95

Gln Ser Gln Ile Leu His Gln Gln Gln Gln Gln Val Ala Ser Met
            100                 105                 110

Ala Ala Val Ala Thr Pro Pro Thr Thr Phe Glu Asn Pro Arg Val
        115                 120                 125
```

```
Gly Phe Leu Ser Pro Lys Pro Val Pro Met Lys His Val Ser Ser Thr
            130                 135                 140
Pro Pro Lys Ala Ala Lys Leu Tyr Arg Gly Val Arg Gln Arg His Trp
145                 150                 155                 160
Gly Lys Trp Val Ala Glu Ile Arg Leu Pro Lys Asn Arg Thr Arg Leu
                165                 170                 175
Trp Leu Gly Thr Phe Asp Thr Ala Glu Glu Ala Ala Leu Ala Tyr Asp
            180                 185                 190
Lys Ala Ala Tyr Lys Leu Arg Gly Glu Phe Ala Arg Leu Asn Phe Pro
        195                 200                 205
His Leu Lys His Gln Gly Ala His Val Phe Gly Glu Phe Gly Asp Tyr
    210                 215                 220
Lys Pro Leu His Ala Ser Val Asp Ala Lys Leu Gln Ala Ile Cys Gln
225                 230                 235                 240
Ser Leu Gln Ala Gln Gly Asn Pro Val Lys Thr Lys Thr Leu Pro Lys
                245                 250                 255
Ala Ala Glu Phe His Tyr Pro Ile Lys Thr Glu Glu Phe Asp His Lys
            260                 265                 270
Gln Asp Asn Ser Ser Ser Ser Ser Ser Val Asp Glu Ser Ser Leu
        275                 280                 285
Ala Gly Ser Leu Ser Ser Pro Glu Ser Asp Ile Thr Phe Phe Asp Phe
    290                 295                 300
Ser Asp Ser Lys Trp Glu Asp Asn Glu Ile Glu Asn Phe Asn Leu Asp
305                 310                 315                 320
Lys Phe Pro Ser Leu Glu Ile Asp Trp Glu Ala Ile
                325                 330

<210> SEQ ID NO 14
<211> LENGTH: 999
<212> TYPE: DNA
<213> ORGANISM: Gossypium hirsutum

<400> SEQUENCE: 14
atggcagctg ttatagatat gtataatagt agcagaaact cagttttta tgatcctta      60
agagaagagt taatgaaagc acttgaacct tttatgaaaa gtgcttcttc ttcttcttct    120
cccttacagc ccaatttgta ccctgaatat tgctccccat gaacagtag tacccacttg    180
ttttcaaacc atgggttctc taactataac aagaacatgt gggttttga gcaaacaggt    240
agttcacttg gcttaaccca actcaccct tctcaaatcc ttcaaattca atcccaaata   300
ttacatcaac aacaacagca acaggttgct tccatggcgg ctgttgcaac accaccacca   360
acaacctttg agaacccaag ggtgggcttt ctttcaccaa gcctgttcc tatgaaacat   420
gtctcttcca ccccaccaaa agctgcgaag ctttataggg gtgtgagaca gaggcattgg    480
ggcaaatggg tggctgaaat tagactccct aagaaccgaa cacgactttg gcttggcact    540
ttcgacacag ctgaagaagc agccttggct tacgacaagg ctgcttacaa gcttagagga    600
gagttcgcta ggctgaattt tccccacctt aagcaccaag gagctcatgt ttttggcgag    660
tttggtgact acaaaccct ccatgcctcg gttgatgcta agctccaggc tatctgtcaa    720
agcttacaag cacaaggcaa tccagtgaag acgaagaccc tcccaaggc cgcggagttt    780
cattacccca tcaaaaccga ggagttcgat cataaacaag caactcatcc atcatcatca    840
tcatcagttg atgaatcatc attagcagga tcattatctt caccagaatc tgatatcact    900
ttcttgatt tctctgattc caatgggaa gacaatgaaa ttgaaaactt caatttagat    960
```

-continued aagttcccat cactggaaat cgattgggaa gccatttga 999

<210> SEQ ID NO 15
<211> LENGTH: 350
<212> TYPE: PRT
<213> ORGANISM: Gossypium hirsutum

<400> SEQUENCE: 15

Met Ala Ala Met Asp Phe Ile Ser Ser Gly Val Asp Gln Ser Asp
1               5                   10                  15

Leu Tyr Gly Gly Glu Leu Met Glu Val Leu Glu Pro Phe Met Lys Ser
                20                  25                  30

Val Ser Ser Ser Pro Ser Pro Ser Pro Ser Pro Ser Ser
            35                  40                  45

Leu Pro Ser Thr Ser Tyr Leu Ser Phe Ser Ser Glu Thr Gln Pro
    50                  55                  60

Asn Phe Tyr Pro Asp Ser Cys Cys Tyr Pro Tyr Pro Thr Pro Met Asp
65                  70                  75                  80

Ser Val Ser Cys Pro Gln Gln Pro Gln Thr Gly Ser Thr Ile Gly Leu
                85                  90                  95

Asn Ser Leu Thr Gln Ala Gln Ile His Gln Ile Gln Leu Gln Phe His
            100                 105                 110

Leu His Asn Asn Gln Pro Ser Tyr Leu Cys Gln Ser Ser Gln Pro Asn
    115                 120                 125

Thr Ile Ser Ala Asn Ser Asn Pro Met Val Ser Phe Leu Cys Pro Lys
130                 135                 140

Pro Val Pro Met Lys His Val Gly Ala Pro Ser Lys Pro Thr Lys Leu
145                 150                 155                 160

Tyr Arg Gly Val Arg Gln Arg His Trp Gly Lys Trp Val Ala Glu Ile
                165                 170                 175

Arg Leu Pro Arg Asn Arg Thr Arg Leu Trp Leu Gly Thr Phe Asp Thr
            180                 185                 190

Ala Glu Glu Ala Ala Leu Ala Tyr Asp Lys Ala Ala Tyr Lys Leu Arg
    195                 200                 205

Gly Asp Phe Ala Arg Leu Asn Phe Pro Asn Leu Arg His His Gly Ser
210                 215                 220

His Val Gly Asp Tyr Lys Pro Leu Pro Ser Ser Val Asp Ala Lys Leu
225                 230                 235                 240

Gln Ala Ile Cys Glu Ser Leu Val Gln Asn Pro Lys Gln Gly Ser Lys
                245                 250                 255

Lys Lys Ser Ser Lys Val Thr Ala Asp Thr Lys Thr Arg Asn Asn Lys
            260                 265                 270

Lys Ser Asp Met Ala Glu Pro Lys Pro Glu Glu Asn Thr Ala Lys Val
    275                 280                 285

Glu Asn Ser Ser Ser Leu Ser Thr Val Gln Ser Glu Ser Glu Gly Ser
290                 295                 300

Ala Val Ser Ser Pro Leu Ser Asp Leu Thr Phe Ser Asp Phe Asp Glu
305                 310                 315                 320

Gln Pro Trp Pro Glu Val Val Ser Ser Glu Thr Phe Met Leu Ser
                325                 330                 335

Lys Tyr Pro Ser Glu Ile Asp Trp Asp Ser Ile Leu Lys Ala
            340                 345                 350

<210> SEQ ID NO 16
<211> LENGTH: 1053

<212> TYPE: DNA
<213> ORGANISM: Gossypium hirsutum

<400> SEQUENCE: 16

```
atggcagctg caatggattt cattagtagt ggagtagatc aatcagatct atatggggga      60
gaattgatgg aagttcttga acctttatg aaaagtgttt cctcctcttc cccctccccc     120
tcccctccc cttcccttc ttctcttcct tctacttctt acctttcttt ctcttcttcc     180
gaaacacagc ctaattttta cccagatagc tgttgttacc cttaccctac accaatggac     240
tcagtatcat gtccccaaca gcctcaaact ggttcaacaa ttgggctaaa tagcttgaca     300
caagctcaga tccatcagat ccagcttcaa ttccacctcc acaacaacca accaagctac     360
cttttgccaaa gttcccaacc caacaccatc agcgccaata gtaacccgat ggttagcttt     420
cttttgccta aacctgtccc aatgaaacac gtgggtgcgc catccaaacc caccaaactt     480
tacagaggag ttaggcaacg ccactgggga aatgggtcg ctgagatccg gttacctaga     540
aaccggacac gtctttggtt aggcactttt gacactgccg aggaagcagc cttggcttat     600
gacaaagcag cttataaact aagaggtgac tttgcgagac tcaacttccc taaccttcgc     660
caccacggtt cccacgttgg tgactacaag cctttgcctt cctctgttga cgctaagctt     720
caagccattt gtgagagctt ggtacaaaac cctaagcaag ggagcaagaa gaaatcatcc     780
aaggttacgg cagacaccaa aaccaggaac aacaaaaaat ccgacatggc agagccaaag     840
cctgaggaga atacagcgaa agtggagaac tcctcatctt tgtctacggt tcaatccgag     900
agtgagggtt cggctgtatc ttcacctta tcagatctta cattctcgga tttcgacgaa     960
caaccatggc cggaagtcgt ttcttcttcg gaaactttta tgttgtccaa gtaccttca    1020
gagatcgatt gggattccat tctaaaagcc tga                                1053
```

<210> SEQ ID NO 17
<211> LENGTH: 321
<212> TYPE: PRT
<213> ORGANISM: Glycine max

<400> SEQUENCE: 17

```
Met Ser Val Val Gly Lys Leu Asn Phe Tyr Met Ala Ala Thr Met Asn
  1               5                  10                  15

Phe Tyr Asn Glu Thr Ser Gln Gln Val Gln Ser Asp Pro Phe Arg Gly
                 20                  25                  30

Glu Leu Met Glu Val Leu Glu Pro Phe Met Lys Thr Cys Pro Ser Ser
             35                  40                  45

Thr Pro Ser Ile Leu Ser Ser Asp Ser Pro Ser Pro Ser Ser Tyr Ser
         50                  55                  60

Pro Leu Leu Pro Pro His Pro Ser Phe Ser Thr Tyr Thr Pro Ser Ala
 65                  70                  75                  80

Tyr Leu Phe Gln Asn Gln Gln Pro Leu Ile Gly Phe Glu Gln Gln Pro
                 85                  90                  95

Ser Ser Leu Leu Gly Leu Asn His Leu Ser Thr Ser Gln Ile Ser Gln
            100                 105                 110

Ile Gln Ala Gln Ala Gln Ala Gln Asn Ser Leu Ser Leu Asn Phe Leu
        115                 120                 125

Gly Pro Lys Pro Val Pro Met Lys His Val Gly Pro Ala Lys Pro
    130                 135                 140

Thr Lys Leu Tyr Arg Gly Val Arg Gln Arg His Trp Gly Lys Trp Val
145                 150                 155                 160
```

Ala Glu Ile Arg Leu Pro Lys Asn Arg Thr Arg Leu Trp Leu Gly Thr
            165                 170                 175

Phe Asp Thr Ala Glu Glu Ala Ala Leu Ala Tyr Asp Lys Ala Ala Tyr
        180                 185                 190

Arg Leu Arg Gly Asp Leu Ala Arg Leu Asn Phe Pro Asn Leu Lys Gly
            195                 200                 205

Ser Cys Pro Gly Glu Glu Tyr Lys Pro Met Gln Ala Ala Val Asp Ala
210                 215                 220

Lys Leu Asp Ala Ile Cys Ala Asn Leu Ala Glu Met Gln Lys Gln Gly
225                 230                 235                 240

Lys Asn Glu Lys Gly Ala Arg Ser Gly Lys Ser Lys Gln Gly Pro
            245                 250                 255

Asn Leu Glu Ala Lys Pro Glu Pro Glu Ala Ser Gly Ser Gly Ala Ala
            260                 265                 270

Ala Leu Ser Pro Glu Ser Glu Gly Ser Ala Asp Ser Ser Ala Leu Ser
            275                 280                 285

Asp Leu Thr Phe Asp Val Thr Glu Pro Gln Trp Glu Asp Ala Ser Ala
        290                 295                 300

His Phe Asn Leu Gln Lys Phe Pro Ser Tyr Glu Ile Asp Trp Asp Ser
305                 310                 315                 320

Leu

<210> SEQ ID NO 18
<211> LENGTH: 966
<212> TYPE: DNA
<213> ORGANISM: Glycine max

<400> SEQUENCE: 18
atgtccgtag ttggaaaatt gaattttat atggcagcta cgatgaattt ctacaacgaa      60
acatcacaac aagttcagtc agatccattc agaggagagc tcatggaagt tctagaacct     120
tttatgaaaa cttgtccttc ctcaactccc tctattctct cctcagattc accatcacct     180
tcctcttact ctcctttact acctccacac cccagtttct ccacatacac ccctctgcc      240 tactattcc aaaaccaaca acccttaata ggctttgagc acaaccaag ttcccttctc       300 gggctcaacc acctaagcac gtctcagatt tcccagatcc aagcccaagc caagcccag      360 aactcgctct ctcttaattt cttgggcccc aagcccgttc tatgaagca cgttggtggg     420 ccggcgaagc ccacgaagct gtaccggggc gtgaggcaga ggcattgggg gaagtgggtg    480
gcggagataa ggctaccgaa gaaccgaacc aggctttggc tcggaacctt cgacacagcc    540
gaggaagccg cttttggctta cgacaaagcc gcgtacaggc tccgaggcga cttggcgagg   600
ctgaacttcc cgaacctgaa aggctcgtgc cccggcgagg agtacaagcc tatgcaggct    660
gcggtggacg ctaagctcga cgcaatctgc gcgaacttgg cggaaatgca gaagcaaggg   720
aagaacgaga agggtgccag gtcggggaag aagtcgaagc aaggtccgaa cctgaggcg   780 aagcccgaac tgaagcttc gggttccggt gctgctgctc tgtctcctga agtgagggt     840 tctgcggatt cttctgcttt gtctgatctt acctttgatg taaccgagcc gcaatgggag    900
gatgcttcag cacatttaa tttgcaaaag tttccttctt atgagatcga ttgggattct    960
ctctga                                                              966

<210> SEQ ID NO 19
<211> LENGTH: 308
<212> TYPE: PRT
<213> ORGANISM: Glycine max

<400> SEQUENCE: 19

```
Met Asn Phe Tyr Asn Gly Thr Ser Gln Glu Gln Val Glu Ser Asp Pro
1               5                   10                  15
Phe Arg Gly Glu Leu Met Glu Val Leu Glu Pro Phe Met Lys Thr Ser
            20                  25                  30
Pro Ser Ser Thr Thr Pro Ser Ile Ile Leu Ser Ser Asp Ser Pro Ser
        35                  40                  45
Ser Ser Ser Phe Asn Phe Pro Ser Ser Ser Leu Leu Ser Pro His Pro
    50                  55                  60
Asn Phe Tyr Thr His Thr Pro Pro Ser Tyr Leu Leu Gln Ser Gln
65                  70                  75                  80
Gln Ser Leu Ile Gly Phe Glu Gln Pro Pro Ser Ser Leu Leu Gly Leu
                85                  90                  95
Asn His Leu Ser Pro Ser Gln Ile Ser Gln Ile Gln Ala Gln Ile Glu
            100                 105                 110
Ala Gln Gln Ser Gln Asn Gln Asn Pro His Ser Leu Asn Phe Leu Gly
        115                 120                 125
Pro Lys Pro Val Pro Met Lys His Val Gly Gly Pro Pro Lys Pro Thr
    130                 135                 140
Lys Leu Tyr Arg Gly Val Arg Gln Arg His Trp Gly Lys Trp Val Ala
145                 150                 155                 160
Glu Ile Arg Leu Pro Lys Asn Arg Thr Arg Leu Trp Leu Gly Thr Phe
                165                 170                 175
Asp Thr Ala Glu Glu Ala Ala Leu Ala Tyr Asp Lys Ala Ala Tyr Arg
            180                 185                 190
Leu Arg Gly Asp Phe Ala Arg Leu Asn Phe Pro Ser Leu Lys Gly Ser
        195                 200                 205
Cys Pro Gly Glu Glu Tyr Lys Pro Val His Ser Ala Val Asp Ala Lys
    210                 215                 220
Leu Asp Ala Ile Cys Ala Asn Leu Ala Glu Met Gln Lys Gln Gly Lys
225                 230                 235                 240
Thr Glu Lys Gly Ala Arg Ser Ala Lys Lys Ser Lys Gln Gly Pro Asn
                245                 250                 255
Gln Glu Ala Lys Pro Glu Pro Gln Ala Ser Ala Glu Ser Glu Gly Ser
            260                 265                 270
Ala Asp Ser Ser Pro Leu Ser Asp Leu Thr Phe Asp Val Thr Glu Pro
        275                 280                 285
Gln Trp Glu His Phe Asn Leu Gln Lys Phe Pro Ser Tyr Glu Ile Asp
    290                 295                 300
Trp Asp Ser Leu
305
```

<210> SEQ ID NO 20
<211> LENGTH: 927
<212> TYPE: DNA
<213> ORGANISM: Glycine max

<400> SEQUENCE: 20

```
atgaatttct acaacggaac atcacaagaa caagttgagt cagatccatt cagaggtgag      60
ctcatggaag ttctagaacc ttttatgaaa actagtcctt cctcaacaac tcctctatt     120
attctctctt cagattcacc ttcatcttca tcttttaatt tcccttcctc ttctttactt     180
tctccacacc ccaatttcta cacacacact ccccccccct tcctacttact ccaaagccaa   240
```

```
caatccttaa taggctttga gcaaccaccg agttcccttc tcgggctcaa ccacctaagc    300
ccgtctcaga tttctcagat ccaggcccag atcgaggccc aacagagcca aaaccagaac    360
ccacactctc tcaactttct cggcccgaag cccgtcccaa tgaagcacgt gggcgggcct    420
ccgaagccca cgaagctgta ccggggcgta aggcagaggc attgggggaa gtgggtggcg    480
gagatcaggc tcccgaagaa ccgaaccagg ctctggctcg gaaccttcga cacggcggag    540
gaagctgctt tggcttacga caaagccgcg tataggctcc gaggcgactt cgcgaggctg    600
aacttcccga gcctgaaagg ctcgtgcccc ggggaggagt acaagcctgt gcattccgcg    660
gtggacgcta agctcgacgc gatttgcgcc aacttggcgg aaatgcagaa gcaagggaag    720
acggagaaag gtgccaggtc agcgaagaaa tcgaagcaag gtccgaacca ggaggccaag    780
cccgaacctc aagcttccgc tgaaagtgag ggttctgcgg attcttctcc gctgtctgat    840
cttacctttg atgtaaccga gccgcaatgg gaacatttta atttgcagaa gtttccttct    900
tatgagatcg attgggattc tctctga                                       927
```

<210> SEQ ID NO 21
<211> LENGTH: 314
<212> TYPE: PRT
<213> ORGANISM: Glycine max

<400> SEQUENCE: 21

```
Met Ala Ala Met Met Asp Phe Tyr Ser Ser Ser Thr Glu Phe Gln Leu
 1               5                  10                  15

His Ser Asp Pro Phe Arg Gly Glu Leu Met Glu Val Leu Glu Pro Phe
            20                  25                  30

Met Lys Ser Pro Phe Ser Thr Pro Ser Pro Ser Asn Ser Cys Phe Leu
        35                  40                  45

Ser Thr Ser Tyr Ser Pro Ser Pro Asn Asn Tyr Ser Pro Ser Leu Tyr
    50                  55                  60

Ser Asn Gly Leu Ser Ser Ile Pro Asn Thr Thr Gln Asn Leu Ile Gly
65                  70                  75                  80

Phe Gly Gln Gly Gln Pro Thr Ser Leu Val Gly Leu Asn His Leu Thr
                85                  90                  95

Pro Ser Gln Ile Ser Gln Ile Gln Ala Gln Ile Gln Ile Gln Asn His
            100                 105                 110

Ser Asn Thr Leu Ser Phe Leu Gly Pro Lys Pro Ile Pro Met Lys His
        115                 120                 125

Val Gly Met Pro Pro Lys Pro Thr Lys Leu Tyr Arg Gly Val Arg Gln
    130                 135                 140

Arg His Trp Gly Lys Trp Val Ala Glu Ile Arg Leu Pro Lys Asn Arg
145                 150                 155                 160

Thr Arg Leu Trp Leu Gly Thr Phe Asp Thr Ala Glu Glu Ala Ala Leu
                165                 170                 175

Ala Tyr Asp Lys Ala Ala Tyr Lys Leu Arg Gly Asp Phe Ala Arg Leu
            180                 185                 190

Asn Phe Pro Asn Leu Arg His Gln Gly Ser Ser Val Gly Gly Asp Phe
        195                 200                 205

Gly Glu Tyr Lys Pro Leu His Ser Ala Val Asp Ala Lys Leu Gln Ala
    210                 215                 220

Ile Cys Glu Gly Leu Ala Glu Leu Gln Lys Gln Gly Lys Thr Glu Lys
225                 230                 235                 240

Pro Pro Arg Lys Thr Arg Ser Lys Leu Ala Ser Pro Pro Glu Asn Asp
                245                 250                 255
```

```
Asn Asn Asn Asp Asn Asn Ser Cys Lys Val Glu Ala Ala Ser Ser Ser
                260                 265                 270

Ser Glu Gly Ser Ser Pro Leu Ser Val Leu Thr Phe Ala Asp Val Ser
        275                 280                 285

Glu Pro Gln Trp Glu Gly Asp Ser Asp Asn Phe Asn Leu Gln Lys Tyr
    290                 295                 300

Pro Ser Tyr Glu Ile Asp Trp Asp Ser Leu
305                 310

<210> SEQ ID NO 22
<211> LENGTH: 945
<212> TYPE: DNA
<213> ORGANISM: Glycine max

<400> SEQUENCE: 22
atggcagcta tgatggattt ttacagcagc agcacagagt ttcaacttca ctcagatcca      60
ttcagggtg aactaatgga agttcttgaa ccttttatga aaagtccttt ctcaaccct     120
tctccttcaa attcttgttt tctttctacc tcttactctc cttcccccaa caactactct    180
ccctccctat actcaaacgg gttatcatcc atacccaaca ccacccaaaa cttaattggt    240
ttcgggcaag gcagcccac atctcttgtg ggcctgaacc acctaaccc atctcagatc     300
tctcagatcc aggcccaaat ccagatccag aatcacagca cacgctgag cttcctgggg    360
ccgaagccca tccctatgaa gcacgtgggc atgcctccga gcccacgaa gctatacaga    420
ggggttcgac agaggcactg ggggaagtgg gtggctgaga ttagactccc gaagaaccgg    480
accaggctat ggctgggaac cttcgacacc gccgaggaag ccgctctggc gtacgacaag    540
gccgcgtaca agctccgagg tgacttcgcc aggctcaact tccccaacct ccgacaccag    600
ggttcctccg tcggtggtga cttcggggag tataagcctc ttcattccgc cgttgacgcc    660
aagcttcagg ccatttgcga gggcctggct gagctgcaga acaggggaa gaccgagaag    720
cctccgagga aacgcgatc caaactcgct ctccgccag agaacgacaa caacaacgac    780
aacaactctt gtaaggtcga agctgcttcc tcctcttctg aaggttcttc gccgctttcg   840
gttctgactt tcgctgacgt cagcgagccg cagtgggaag gtgattcgga taattttaat   900
ctccagaagt accctctta tgagatcgac tgggattctc tgtga                    945

<210> SEQ ID NO 23
<211> LENGTH: 302
<212> TYPE: PRT
<213> ORGANISM: Glycine max

<400> SEQUENCE: 23

Met Ala Ala Leu Met Asp Phe Tyr Ser Ser Ser Pro Glu Phe Gln Leu
  1               5                  10                  15

His Ser Asp Pro Phe Arg Gly Glu Leu Met Glu Val Leu Glu Pro Phe
                 20                  25                  30

Met Lys Ser Pro Ser Pro Asn Tyr Phe Pro Ser Ser Pro Ser Leu Pro
             35                  40                  45

Asn Leu Tyr Ser Asn Gly Leu Ser Ser Asn Thr Gln Ser Leu Ile Gly
         50                  55                  60

Phe Gly Gln Ala Gln Pro Thr Ser Leu Val Gly Leu Asn His Leu Thr
 65                  70                  75                  80

Pro Ser Gln Ile Ser Gln Ile Gln Ala Gln Ile Gln Ile Gln Ala Gln
                 85                  90                  95
```

-continued

```
Gln His Gln Asn Arg Ser Asn Thr Leu Ser Phe Leu Gly Pro Lys Pro
            100                 105                 110

Ile Pro Met Lys His Ala Gly Met Pro Pro Lys Pro Thr Lys Leu Tyr
        115                 120                 125

Arg Gly Val Arg Gln Arg His Trp Gly Lys Trp Val Ala Glu Ile Arg
    130                 135                 140

Leu Pro Lys Asn Arg Thr Arg Leu Trp Leu Gly Thr Phe Asp Thr Ala
145                 150                 155                 160

Glu Glu Ala Ala Leu Ala Tyr Asp Lys Ala Ala Tyr Lys Leu Arg Gly
                165                 170                 175

Asp Phe Ala Arg Leu Asn Phe Pro Asn Leu Arg His Gln Gly Ser Ser
            180                 185                 190

Val Gly Gly Asp Phe Gly Glu Tyr Lys Pro Leu His Ser Ala Val Asp
        195                 200                 205

Ala Lys Leu Gln Ala Ile Cys Glu Gly Leu Ala Glu Leu Gln Lys Gln
    210                 215                 220

Gly Lys Thr Glu Lys Pro Pro Arg Lys Ser Arg Ser Lys Leu Ala Glu
225                 230                 235                 240

Lys Val Val Ser Asp Lys Glu Asn Asn Asn Ser Cys Lys Val Glu Ala
                245                 250                 255

Ala Ser Trp Ser Ser Glu Gly Ser Ser Pro Leu Ser Asp Leu Thr Phe
            260                 265                 270

Ala Asp Val Ser Glu Ala Gln Trp Glu Gly Asp Ser Asp Asn Tyr Asn
        275                 280                 285

Leu Gln Lys Tyr Pro Ser Tyr Glu Ile Asp Trp Asp Ser Leu
    290                 295                 300
```

<210> SEQ ID NO 24
<211> LENGTH: 909
<212> TYPE: DNA
<213> ORGANISM: Glycine max

<400> SEQUENCE: 24

| | | | | | |
|---|---|---|---|---|---|
| atggcagctt | tgatggattt | ttacagcagc | agcccagagt | tcaacttca | ctcagatcca | 60 |
| ttcaggggag | aactaatgga | agttcttgaa | ccttttatga | aaagtccttc | tcccaactat | 120 |
| ttcccttcct | cccctccct | ccctaatctt | tactcaaacg | ggttatccag | caacacccaa | 180 |
| agcttaattg | gcttcgggca | agcgcaaccc | acatctcttg | tgggcctgaa | ccacctaacc | 240 |
| ccatctcaga | tctctcagat | ccaagcccaa | atccagatcc | aggcccagca | gcatcagaat | 300 |
| cgcagcaaca | ccctgagctt | ccttgggccg | aagcccatcc | ccatgaagca | cgcgggcatg | 360 |
| cctccgaagc | ccacgaagct | tacagagggg | gtgagacaga | ggcactgggg | aaagtgggtg | 420 |
| gctgagatca | gacttcccaa | gaaccggacc | aggctgtggc | tgggaacctt | cgacaccgcc | 480 |
| gaggaagccg | ctctggcata | cgacaaggcc | gcgtacaagc | tccgaggtga | cttcgccagg | 540 |
| ctcaacttcc | caaacctgcg | acaccagggt | tcctccgtcg | gtggtgattt | cggggagtac | 600 |
| aagcctcttc | attccgctgt | tgacgccaag | cttcaggcca | tttgcgaagg | cctggctgag | 660 |
| ctgcagaaac | aggggaagac | cgagaagcct | ccgaggaagt | cgcgttccaa | actcgcggag | 720 |
| aaggttgttt | ccgacaagga | gaacaacaac | tcttgtaagg | tggaagctgc | gtcctggtcg | 780 |
| tcggaaggtt | cttcgccgct | ttcggatctg | acgtttgctg | acgtgagcga | ggctcagtgg | 840 |
| gaaggtgatt | cggataatta | taatctccag | aagtacccct | cttatgagat | cgattgggat | 900 |
| tctctgtga | | | | | | 909 |

<210> SEQ ID NO 25
<211> LENGTH: 312
<212> TYPE: PRT
<213> ORGANISM: Glycine max

<400> SEQUENCE: 25

```
Met Gly Thr Ala Ile Asp Met Tyr Asn Ser Ser Asn Ile Val Ala Asp
 1               5                  10                  15
Phe Leu Asp Pro Tyr Ser Glu Glu Leu Met Lys Ala Leu Lys Pro Phe
             20                  25                  30
Met Lys Ser Asp Tyr Phe Ser Ala Ser Ser Ser Ser Ser Leu Glu Ser
         35                  40                  45
Gln Pro Cys Ser Phe Ser Ser Asn Ser Leu Pro Thr Ser Tyr Pro Ser
     50                  55                  60
Ser Asn Gln Ile Lys Leu Asn Gln Leu Thr Pro Asp Gln Ile Val Gln
 65                  70                  75                  80
Ile Gln Ala Gln Ile His Ile Gln Gln Gln Gln His Val Ala Gln
                 85                  90                  95
Thr Gln Thr His Leu Gly Pro Lys Arg Val Pro Met Lys His Ala Gly
            100                 105                 110
Thr Ala Ala Lys Pro Thr Lys Leu Tyr Arg Gly Val Arg Gln Arg His
        115                 120                 125
Trp Gly Lys Trp Val Ala Glu Ile Arg Leu Pro Lys Asn Arg Thr Arg
    130                 135                 140
Leu Trp Leu Gly Thr Phe Asp Thr Ala Glu Ala Ala Leu Ala Tyr
145                 150                 155                 160
Asp Asn Ala Ala Phe Lys Leu Arg Gly Glu Phe Ala Arg Leu Asn Phe
                165                 170                 175
Pro His Leu Arg His His Gly Ala Phe Val Phe Gly Glu Phe Gly Asp
            180                 185                 190
Tyr Lys Pro Leu Pro Ser Ser Val Asp Ser Lys Leu Gln Ala Ile Cys
        195                 200                 205
Glu Ser Leu Ala Lys Gln Glu Glu Lys Pro Cys Cys Ser Val Glu Asp
    210                 215                 220
Val Lys Pro Val Ile His Ala Ala Glu Leu Ala Glu Val Glu Ser Asp
225                 230                 235                 240
Val Ala Lys Ser Asn Ala Glu Tyr Val Tyr Pro Glu Phe Gln Asp Phe
                245                 250                 255
Lys Val Glu His Glu Asn Pro Met Phe Ser Gly Glu Ser Ser Ser Pro
            260                 265                 270
Glu Ser Ser Val Thr Phe Leu Asp Phe Ser Asp Phe Ser Asp Ser Asn
        275                 280                 285
Asn Gln Trp Asp Glu Met Glu Asn Phe Gly Leu Glu Lys Phe Pro Ser
    290                 295                 300
Val Glu Ile Asp Trp Glu Ala Ile
305                 310
```

<210> SEQ ID NO 26
<211> LENGTH: 939
<212> TYPE: DNA
<213> ORGANISM: Glycine max

<400> SEQUENCE: 26
atgggaactg ctatagacat gtacaacagc agcaacatcg tagcggattt cctagatccg     60
tatagtgaag agctgatgaa agcacttaag cctttttatga aaagtgatta tttctctgcc    120

-continued

| | |
|---|---:|
| tcttcttctt cttcactcga atcacagcct tgttctttt catctaattc tctccccact | 180 |
| tcgtatccct cttccaacca aatcaagctc aaccaactca ccccagacca aattgttcag | 240 |
| attcaggccc aaatccacat tcagcagcag cagcagcacg tggcccaaac ccaaacccac | 300 |
| ctgggcccaa aacgcgtccc catgaagcac gctggcacgg ccgcgaaacc cacgaagctc | 360 |
| taccgcgggg tgcggcaacg gcattggggc aagtgggtcg ctgaaatcag actcccaaag | 420 |
| aaccgcacgc gcctctggct aggaacattc gacaccgcag aggaagcagc attagcgtac | 480 |
| gacaacgcag cgtttaagct cagaggcgag ttcgcgcgtc tcaatttcc tcatctaaga | 540 |
| caccacggag ccttcgtttt cggcgagttc ggagattaca agcctctacc ttcttccgtg | 600 |
| gattccaaac tgcaagctat ttgcgaaagc ttagcgaaac aagaggaaaa gccgtgttgc | 660 |
| tccgtcgaag acgtgaagcc cgtgatacac gctgctgagc tggcagaggt cgagtctgac | 720 |
| gtggcaaaat cgaacgctga atatgtttat cccgagttcc aggatttaa ggtcgagcac | 780 |
| gagaacccaa tgttttctgg ggaatcttct tcgcctgaat ccagtgttac tttcttggat | 840 |
| ttctcggact ctcggattc taataatcag tgggatgaaa tggagaattt tggttggag | 900 |
| aagttcccctt ctgtggagat tgattgggaa gctatatga | 939 |

<210> SEQ ID NO 27
<211> LENGTH: 366
<212> TYPE: PRT
<213> ORGANISM: Lycopersicon esculentum

<400> SEQUENCE: 27

```
Met Ala Ala Met Asp Phe Trp Asn Ser Thr Cys Val Asp Phe Glu Leu
  1               5                  10                  15

Ser Ser Glu Pro Val Thr Ser Gly Gly Glu Leu Met Glu Ala Leu Glu
             20                  25                  30

Pro Phe Met Lys Ser Ala Ser Ser Pro Ser Pro Pro Ser Thr
         35                  40                  45

Phe Pro Pro Val Phe Pro Ser Ser Ser Ser Thr Phe Pro Ser Ser
     50                  55                  60

Asp Phe Gln Ser Phe Pro Ser Phe Pro Pro Thr Pro Pro Ile Ser
 65                  70                  75                  80

Tyr Pro Tyr Thr Ser Ser Phe Tyr Pro Ser Thr Met Ser Ser Glu Val
                 85                  90                  95

Cys Ser Thr Ser Thr Glu Met Asn Ser Gln Ile Phe Ser Thr Gly Phe
            100                 105                 110

Ser Gly Tyr Gly Met Glu Gln Gln Gly Ser Ile Gly Leu Asn Gln Leu
        115                 120                 125

Thr Pro Ile Gln Ile Gln Gln Ile Gln Ala Gln Ile Asn Phe Gln Asn
    130                 135                 140

Gln Gln Gln Gln Gln Gln Gln Met Met Leu Gln Thr Ala His His
145                 150                 155                 160

Ala Ser Thr Met Asn Phe Leu Ala Pro Lys Pro Val Pro Met Lys Gln
                165                 170                 175

Ser Gly Ser Pro Pro Lys Pro Thr Lys Leu Tyr Arg Gly Val Arg Gln
            180                 185                 190

Arg His Trp Gly Lys Trp Val Ala Glu Ile Arg Leu Pro Lys Asn Arg
        195                 200                 205

Thr Arg Leu Trp Leu Gly Thr Phe Asp Thr Ala Glu Glu Ala Ala Leu
    210                 215                 220
```

```
Ala Tyr Asp Lys Ala Ala Tyr Met Leu Arg Gly Asp Phe Ala Arg Leu
225                 230                 235                 240

Asn Phe Pro Gln Leu Arg His Asn Gly Asn Leu Ile Gly Gly Asp Phe
            245                 250                 255

Gly Glu Tyr Asn Pro Leu His Ser Ser Val Asp Ala Lys Leu Lys Asp
            260                 265                 270

Ile Cys Gln Ser Leu Ala Gln Gly Lys Ser Ile Asp Ser Lys Lys Lys
        275                 280                 285

Lys Thr Lys Gly Leu Ser Ala Glu Lys Ala Ala Val Val Lys Met Glu
    290                 295                 300

Glu Glu Glu Ser Lys Thr Ala Glu Val Gly Ser Glu Ser Asp Gly Ser
305                 310                 315                 320

His Ser Gly Ser Gly Gly Ser Ser Pro Val Thr Glu Leu Ile Phe Pro
            325                 330                 335

Glu Phe Thr Glu Glu Glu Pro Thr Trp Asp Met Ser Glu Asn Phe Leu
            340                 345                 350

Leu Gln Lys Tyr Pro Ser His Glu Ile Asp Trp Ala Ser Leu
        355                 360                 365
```

<210> SEQ ID NO 28
<211> LENGTH: 1101
<212> TYPE: DNA
<213> ORGANISM: Lycopersicon esculentum

<400> SEQUENCE: 28

```
atggcagcta tggattttg gaatagtaca tgtgtagatt ttgaattatc atcagaacct      60
gttacttctg gtggtgaatt aatggaagct cttgaacctt ttatgaaaag tgcttcttct     120
tctccttctc ctccaccttc tactttcct cctgttttcc cttcttcttc ttcttcaact     180
tttccttctt cagattttca atcttttcct tcatttcctc ctccaactcc tcccatttca     240
tatccctaca cttcttcttt ttacccatct actatgagct ctgaggtttg ttccacttcc     300
acagagatga attcccaaat cttttcaact gggttttctg ggtatggaat ggagcaacag     360
ggttcaattg gctgaatca gttaaccca attcagatcc agcaaattca agctcaaatc     420
aactttcaaa accaacaaca acagcagcag cagcagatga tgttacagac tgcccatcat     480
gcttccacca tgaatttctt ggctccaaag ccggttccaa tgaagcaatc tgggtcgcca     540
ccaaaaccca cgaagctcta cagaggtgtt agacaacgcc actgggtaa gtgggtcgct     600
gagatccgtt tgcctaagaa ccgaacccgc ctttggcttg gtacatttga caccgctgaa     660
gaagctgctc tggcttacga caaggcggcg tatatgcttc gtggcgactt tgctcgactg     720
aacttccctc aactccgcca caacggcaac ctaatcggcg cgactttgg tgaatacaat     780
ccattgcatt cctcagttga tgctaagcta aaggacatat gccaaagctt ggcacagggg     840
aagagcattg actctaagaa gaagaaaacc aaagggttgt cggcggagaa agcggcggtg     900
gtgaagatgg aggaagagga gagcaaaaca gcagaagttg gatccgaaag tgacgggtcc     960
cattccggtt ccggtggatc atcgccggtg accgaactga tattcccgga gttcactgag    1020
gaagagccaa cttgggacat gtcagaaaat ttttgttgc agaagtatcc atctcatgaa     1080
attgattggg cctctctata a                                               1101
```

<210> SEQ ID NO 29
<211> LENGTH: 367
<212> TYPE: PRT
<213> ORGANISM: Lycopersicon esculentum

```
<400> SEQUENCE: 29

Met Ala Ala Ile Asp Val Tyr Ser Ser Ser Asn Leu Ser Asp
 1               5                  10                  15

Pro Leu Thr Glu Glu Leu Met Lys Ala Leu Glu Pro Phe Met Lys Gly
            20                  25                  30

Val Ser Tyr Ser Ser Ser Ser Pro Ser Thr Ser Ser Ser Phe
            35                  40                  45

Tyr Thr Phe Gly Glu Pro Asn Leu Tyr Thr Asp Phe Cys Thr Ile Pro
        50                  55                  60

Ser Thr Ala Thr Gln Met Phe Ser Gln Gly Tyr Ser Cys Phe Asp Asn
 65                  70                  75                  80

Met Gly Val Ala Glu Thr Gly Ser Ile Gly Leu Asn His Leu Thr Pro
                85                  90                  95

Ser Gln Ile Leu Gln Ile Gln Ala Gln Ile Gln Phe Gln Asn Gln Gln
            100                 105                 110

Gln Gln Leu Gln Leu Leu His Gln Gln Gln Ser Leu Gly Leu Leu
            115                 120                 125

Thr Pro Thr Ser Thr Tyr Ser Lys Asn Leu Asn Ser Thr Asn Phe Leu
130                 135                 140

Gly Met Lys Pro Val Pro Met Lys Gln Thr Gly Ala Thr Ser Ser Gln
145                 150                 155                 160

Lys Ala Thr Lys Leu Tyr Arg Gly Val Arg Gln Arg His Trp Gly Lys
                165                 170                 175

Trp Val Ala Glu Ile Arg Leu Pro Lys Asn Arg Thr Arg Leu Trp Leu
            180                 185                 190

Gly Thr Phe Asp Thr Ala Glu Glu Ala Ala Leu Ala Tyr Asp Lys Ala
        195                 200                 205

Ala Tyr Lys Leu Arg Gly Glu Phe Ala Arg Leu Asn Phe Pro His Leu
210                 215                 220

Arg His Gln Leu Asn Asn Glu Phe Ser Asp Phe Lys Pro Leu His Ser
225                 230                 235                 240

Ser Val Asp Ala Lys Leu Gln Ala Ile Cys Gln Ser Leu Ala Asn Pro
                245                 250                 255

Lys Ser Asp Asp Ser Cys Ser Lys Ser Asn Ser Lys Pro Arg Lys Ser
            260                 265                 270

Lys Thr Ala Ala Val Ser Val Asp Ser Asn Ser Ala Gln Glu Ser Ser
        275                 280                 285

Ser Lys Ser Glu Ile Thr Thr Asp Asp Ser Leu Lys Glu Glu Phe Ser
290                 295                 300

Tyr Pro Glu Asn Gly Thr Ile Lys Ile Glu Ala Ser Ser Ser Ser
305                 310                 315                 320

Pro Pro Thr Pro Ser Glu Glu Ser Ser Ser Ser Glu Ser Asp Ile
                325                 330                 335

Thr Phe Leu Asp Phe Ala Glu Pro Ser Phe Asp Glu Ser Glu Asn Phe
            340                 345                 350

Phe Leu Pro Lys Tyr Pro Ser Val Glu Ile Asp Trp Ala Ala Leu
            355                 360                 365

<210> SEQ ID NO 30
<211> LENGTH: 1104
<212> TYPE: DNA
<213> ORGANISM: Lycopersicon esculentum

<400> SEQUENCE: 30
```

-continued

```
atggcagcag ctatagatgt atacagcagc agcagtaact tgtcagatcc tttaacagaa      60
gaacttatga aagcacttga acctttatg aaaggtgttt cttattcttc ttcttcttca      120
ccttcaactt cgtcttcttc tttctatact tttggtgagc ctaatttgta tactgatttc      180
tgcacaatcc catcaacggc tacccaaatg ttttctcaag ggtattcgtg ttttgacaat      240
atgggtgtag ctgaaacagg ttcaattggg cttaaccatc taaccccttc tcagatcttg      300
caaatccaag ctcagatcca atttcaaaat caacagcaac aactcaaact attacatcaa      360
caacaacaga gcttaggttt gttaacaccc acttcaacat attctaagaa tctgaattct      420
actaactttc ttggtatgaa accagtccca atgaagcaaa cgggtgctac ttcttcacag      480
aaggctacta agctttatcg tggagttaga caacgccatt ggggcaaatg ggttgctgaa      540
attagacttc taagaacag aactaggctt tggttaggca cttttgatac agctgaagag      600
gctgctttgg cttatgacaa agctgcttat aagctaagag gtgagtttgc taggcttaat      660
tttccacatc taaggcatca attaaacaat gaattctctg atttcaagcc tttgcattcc      720
tctgtggatg ctaaacttca agccatttgc caaagcttgg ctaatcccaa atcagatgac      780
tcgtgttcta atctaattc caagccaaga agtccaaaa ctgcagcagt tcagtggat      840 tcaaattcag ctcaagaatc ttcatcaaag tcagaaatca ccacagatga ttcattgaaa      900
gaagaattca gctatccaga aaatggtact atcaagattg aggcttcatc atcatcatca      960 cccctacac cctctgagga atcatcatct tcgtctgagt ctgatattac tttcttggat     1020
ttcgctgaac catcttttcga tgaatcagaa aacttctttt tacccaagta cccttccgtg     1080
gagattgatt gggcagctct ttga                                           1104
```

<210> SEQ ID NO 31
<211> LENGTH: 226
<212> TYPE: PRT
<213> ORGANISM: Lotus japonicus

<400> SEQUENCE: 31

```
Met Ala Thr Met Met Asp Phe Phe Ser Thr Glu Phe His Ser Asp
  1               5                  10                  15

Pro Phe Arg Gly Glu Leu Met Glu Val Leu Glu Pro Phe Ile Lys Ser
                 20                  25                  30

Ser Ser Pro Thr Pro Thr Ser Thr Ser Thr Phe Ser Pro Ser Ser Ser
             35                  40                  45

Ser Ser Ser Ser Ser Ser Ser Pro Ser Pro Ser Ser Ser Asn Ser
         50                  55                  60

Ser Leu Pro Cys Ser Ser Pro Pro Asn Ser Phe Tyr Ser Ser Pro Ser
 65                  70                  75                  80

Val Thr Pro Phe Phe Ser Asp Gly Cys Ser Thr Ser Met Thr His Val
                 85                  90                  95

Phe Ala Asn Gly Leu Ser Phe Val Gln Pro Ala Thr Ser Pro Pro Leu
                100                 105                 110

Leu Gly Phe Asn His Leu Thr Pro Ser Gln Ile His Gln Ile Gln Ser
            115                 120                 125

Gln Ile Gln Ile Gln Gln Asn Asn His Leu Pro Trp Gln Asn Gln Asn
        130                 135                 140

Gln Asn His His Leu Asn Thr Thr Leu Ser Phe Leu Ser Pro Lys Pro
145                 150                 155                 160

Ile Pro Met Lys His Val Ala Asn Pro Pro Lys Pro Thr Lys Leu Tyr
                165                 170                 175
```

Arg Gly Val Arg Gln Arg His Trp Gly Lys Trp Val Ala Glu Ile Arg
            180                 185                 190

Leu Pro Lys Asn Arg Thr Arg Leu Trp Leu Gly Thr Phe Asp Thr Ala
        195                 200                 205

Glu Glu Ala Ala Leu Ala Tyr Asp Lys Ala Ala Tyr Lys Leu Arg Gly
    210                 215                 220

Asp Phe
225

<210> SEQ ID NO 32
<211> LENGTH: 678
<212> TYPE: DNA
<213> ORGANISM: Lotus japonicus

<400> SEQUENCE: 32

| | |
|---|---|
| atggctacta tgatggactt tttcagcagc acagagtttc actcagatcc attcaggggt | 60 |
| gagttgatgg aagttcttga acctttatc aaaagttctt ccccaacccc aacctcaacc | 120 |
| tcaaccttct ctccttcttc ttcttcttct tcttcttctt cttcttctcc ctctccatct | 180 |
| tcatcaaatt catctctacc ctgttcttct ccccctaatt ccttctactc ttctccttct | 240 |
| gtcactcctt tcttctcaga tggttgctca acatcgatga cccatgtatt tgcaaacggg | 300 |
| ttatcctttg tgcaaccagc aacttctcct cctcttcttg gcttcaacca cctaacccca | 360 |
| tctcagatcc atcagatcca atctcagatc cagatccaac agaacaacca cctcccatgg | 420 |
| cagaatcaga atcagaatca ccatctcaac accacactca gcttccttag tccgaagccg | 480 |
| attccgatga agcacgtggc gaatcctcca aaacccacga agctatacag aggagtgagg | 540 |
| cagaggcact ggggaaaatg ggtcgctgag atcaggcttc caaagaatcg gaccaggctc | 600 |
| tggttgggga catttgacac ggcggaggaa gctgctctgg cgtacgacaa ggctgcgtac | 660 |
| aagctcagag gcgacttt | 678 |

<210> SEQ ID NO 33
<211> LENGTH: 333
<212> TYPE: PRT
<213> ORGANISM: Lactuca sativa

<400> SEQUENCE: 33

Met Ala Ser Thr Ala Met Asp Phe Trp Asn Asn Asn Glu Phe Gln Gln
1               5                   10                  15

Ser Thr Ala Gly Gly Glu Leu Met Glu Ala Leu Glu Pro Phe Tyr Lys
            20                  25                  30

Ser Ala Ser Pro Ser Ser Ser Tyr Ser Gln Met Ala Ser Ser Asn
        35                  40                  45

Tyr Gln Asn Thr Leu Pro Phe Ser Thr Pro Ser Ala Ser Tyr Pro Tyr
    50                  55                  60

Pro Ser Ser Ser Phe Asp Ser Phe Pro Ser Ser Ser Tyr Val Pro
65                  70                  75                  80

Thr Thr His Gln Gln Thr Gly Phe Phe Pro Asp Tyr Ser Ile Gln Asp
                85                  90                  95

Arg Phe Val Tyr Asp Gln Pro Gly Ser Ser Leu Gly Leu Asn Leu Asn
            100                 105                 110

Gln Leu Ser Glu Ser Gln Ile Tyr Gln Ile Gln Thr Gln Met Glu Ile
        115                 120                 125

Pro Thr Gln Trp Pro Gln Thr Asn Leu Asn Phe Met Ala Gln Asp Pro
    130                 135                 140

```
Asp Pro Val Pro Val Lys Gln Ser Gly Ser Pro Lys Pro Pro Lys
145                 150                 155                 160

Leu Tyr Arg Gly Val Arg Gln Arg His Trp Gly Lys Trp Val Ala Glu
            165                 170                 175

Ile Arg Leu Pro Lys Ser Arg Thr Arg Leu Trp Leu Gly Thr Phe Asp
                180                 185                 190

Ser Ala Glu Glu Ala Ala Leu Ala Tyr Asp Lys Ala Ala Tyr Lys Leu
            195                 200                 205

Arg Gly Asp Tyr Ala Arg Leu Asn Phe Pro Gln Leu Arg Gln Asn Gly
        210                 215                 220

Ser Tyr Val Thr Asp Phe Lys Pro Leu His Ser Ser Val Val Ala Lys
225                 230                 235                 240

Leu Gln Thr Ile Cys Gln Cys Leu Ala Glu Gly Arg Ser Val Asp Gly
                245                 250                 255

Thr Lys Lys Ala Gly Ser Arg Arg Ser Ser Gly Lys Thr Ala Thr Ala
            260                 265                 270

Thr Val Leu Ser Gln Glu Ala Val Lys Val Glu Gly Cys Glu Ser Glu
        275                 280                 285

Gly Tyr Ala Gly Ser Gly Asn Ser Ser Pro Ser Asp Leu Thr Phe
290                 295                 300

Pro Glu Phe Thr Glu Asp Asp Asn Ala Trp Ser Glu Asn Phe Ser Leu
305                 310                 315                 320

Glu Lys Tyr Pro Ser Tyr Glu Ile Asp Trp Gly Ser Ile
                325                 330

<210> SEQ ID NO 34
<211> LENGTH: 1002
<212> TYPE: DNA
<213> ORGANISM: Lactuca sativa

<400> SEQUENCE: 34
atggcttcta ctgccatgga tttctggaat aacaatgagt ttcagcaatc aacagctggt      60
ggtgaattaa tggaggcact tgaaccttt tataaaagtg cctcaccttc ctcttcttct     120
tattctcaaa tggcgtcttc taattaccaa aatacccttc ctttctctac accttctgcc     180
tcttatccat acccttcttc atctttcgac tcatttcctt catcttcttc ttacgtcccc     240
accacccatc aacaaaccgg tttcttcccg gattactcaa tccaagaccg gtttgtgtac     300
gaccaacccg gttcttccct cgggttgaac ttgaaccagt tatccgaatc ccagatttac     360
cagatccaaa cccagatgga aatacccaca caatggccac agactaactt gaatttcatg     420
gctcaagatc ctgatcctgt acccgtaaaa caatccgggt cacctccgaa acccccgaag     480
ctttacaggg gtgtgaggca aaggcactgg ggaaaatggg tcgccgagat ccgtttaccc     540
aagagccgga cccggctttg gttgggtaca ttcgactctg cggaggaagc ggcgttggca     600
tatgataaag ccgcgtataa gctccgtgga gactacgccc ggctcaactt ccgcagctt     660 cggcaaaacg gctcttatgt caccgacttt aagccgttgc attcttctgt cgtcgccaag     720
ctacagacga tttgtcagtg tttggcggag ggaggtccg tggacggcac taagaaggcc     780
ggttcacggc ggtcatcggg aagacagca acagcaactg ttttgtcgca agaggctgtg     840
aaggtggaag ttgtgagag cgaagggtac gccggatcgg gaaactcatc gccgtcgtct     900
gatctgacgt tccccggagtt cacggaggac gacaatgctt ggtcggagaa tttctcactg     960
gagaagtatc cgtcgtatga gatcgactgg ggttctatct ag                      1002
```

<210> SEQ ID NO 35
<211> LENGTH: 195
<212> TYPE: PRT
<213> ORGANISM: Populus

<400> SEQUENCE: 35

Met Lys Gln Ile Gly Thr Gln Pro Lys Ala Thr Lys Leu Tyr Arg Gly
1               5                   10                  15

Val Arg Gln Arg His Trp Gly Lys Trp Val Ala Glu Ile Arg Leu Pro
            20                  25                  30

Lys Asn Arg Thr Arg Leu Trp Leu Gly Thr Phe Asp Thr Ala Glu Glu
        35                  40                  45

Ala Ala Leu Ala Tyr Asp Arg Ala Ala Tyr Lys Leu Arg Gly Asp Phe
    50                  55                  60

Ala Arg Leu Asn Phe Pro Asn Leu Ile His Gln Gly Ser Tyr Ile Gly
65                  70                  75                  80

Glu Tyr Lys Pro Leu His Ser Ser Val Asp Ala Lys Leu Lys Ala Ile
                85                  90                  95

Cys Lys Ser Leu Glu Asn Ser Ser Gln Gln Lys Gln Gly Gly Lys Thr
            100                 105                 110

Lys Arg Gln Ser Asn Ser Thr Lys Lys Ala Asn Leu Ala Val Val
        115                 120                 125

Thr Gln Glu Glu Gln Val Val Val Lys Ala Glu Thr Gln Ser Pro
    130                 135                 140

Ala Leu Thr Glu Ser Thr Gly Ser Gly Gly Ser Ser Pro Leu Ser Asp
145                 150                 155                 160

Leu Thr Phe Pro Asp Phe Glu Glu Ala Pro Leu Asp Phe Glu Ser Gly
                165                 170                 175

Asn Phe Met Leu Gln Lys Tyr Pro Ser Tyr Glu Ile Asp Trp Ala Ser
            180                 185                 190

Ile Leu Ser
        195

<210> SEQ ID NO 36
<211> LENGTH: 588
<212> TYPE: DNA
<213> ORGANISM: Populus

<400> SEQUENCE: 36
atgaaacaaa tcggtacaca accaaaagcc acaaaacttt acagaggagt aaggcaaagg      60
cactggggca atgggtcgc tgagatccgt ttgcccaaga accgaacccg actctggctt     120
ggcacattcg acacagctga ggaggcagct ttggcttatg acagagcagc ttataaacta     180
agaggcgact ttgcaagact gaacttccca aacttaatcc accaagggtc ctacatcggc     240
gaatacaagc ctctccattc ctcagtggat gcgaaactta agctatttg taaaagcttg     300
gagaactctt cgcagcagaa acaaggaggg aaaacgaaga gcaaagtaa ctcgacgaag     360
aagaaagcca acttggcagt ggtgacccag gaggaggagc aagtggttgt taaggctgag     420
acacagtctc cggcattgac cgagagtact gggtcgggtg atcttcgcc tttgtcggat     480
ctgacgtttc cggattttga ggaagcaccg ttggattttg aatcgggaa tttcatgttg     540
cagaagtatc cctcttatga gattgattgg gcttcaattt tatcttag               588

<210> SEQ ID NO 37
<211> LENGTH: 232
<212> TYPE: PRT
<213> ORGANISM: Sorghum bicolor

<400> SEQUENCE: 37

| | | | | | | | | | | | | | | |
|---|---|---|---|---|---|---|---|---|---|---|---|---|---|---|
|Met|Ala|Ala|Ala|Ile|Asp|Met|Tyr|Lys|Tyr|Tyr|Asn|Ala|His|Gln|Ile
|1| | | |5| | | | |10| | | | |15|
|Ala|Ser|Ser|Ser|Pro|Ser|Asp|Glu|Glu|Leu|Ala|Lys|Ala|Leu|Glu|Pro
| | | | |20| | | | |25| | | | |30| |
|Phe|Ile|Thr|Ser|Ala|Ser|Ser|Ser|Pro|Tyr|His|Arg|Tyr|Ser|Ser|
| | | |35| | | | |40| | | | |45| | |
|Ser|Pro|Ser|Met|Ser|Gln|Asp|Ser|Tyr|Met|Pro|Thr|Pro|Ser|Tyr|Thr
| |50| | | | |55| | | | |60| | | | |
|Ser|Phe|Ala|Thr|Ser|Pro|Leu|Pro|Thr|Pro|Ala|Ala|Thr|Ser|Ser|Ser
|65| | | | |70| | | | |75| | | | |80|
|Ser|Ser|Pro|Phe|Ser|Gln|Leu|Pro|Pro|Leu|Tyr|Ser|Ser|Pro|Tyr|Ala
| | | | |85| | | | |90| | | | |95| |
|Ala|Pro|Ser|Met|Val|Gly|Gln|Met|Gly|Leu|Asn|Gln|Leu|Gly|Pro|Ala
| | | |100| | | | |105| | | | |110| | |
|Gln|Ile|Gln|Gln|Ile|Gln|Ala|Gln|Phe|Met|Phe|Gln|Gln|Gln|Gln|Gln
| | |115| | | | |120| | | | |125| | | |
|Gln|Gln|Arg|Gly|Leu|His|Ala|Ala|Phe|Leu|Gly|Pro|Arg|Ala|Gln|Pro
| |130| | | | |135| | | | |140| | | | |
|Met|Lys|Gln|Ser|Gly|Ser|Pro|Pro|Leu|Ala|Pro|Ala|Gln|Ser|Lys|Leu
|145| | | | |150| | | | |155| | | | |160|
|Tyr|Arg|Gly|Val|Arg|Gln|Arg|His|Trp|Gly|Lys|Trp|Val|Ala|Glu|Ile
| | | | |165| | | | |170| | | | |175| |
|Arg|Leu|Pro|Lys|Asn|Arg|Thr|Arg|Leu|Trp|Leu|Gly|Thr|Phe|Asp|Thr
| | | |180| | | | |185| | | | |190| | |
|Ala|Glu|Asp|Ala|Ala|Leu|Ala|Tyr|Asp|Lys|Ala|Ala|Phe|Arg|Leu|Arg
| | |195| | | | |200| | | | |205| | | |
|Gly|Asp|Met|Ala|Arg|Leu|Asn|Phe|Pro|Ala|Leu|Arg|Arg|Asp|Gly|Ala
| |210| | | | |215| | | | |220| | | | |
|His|Leu|Ala|Gly|Pro|Leu|His|Ala| | | | | | | | |
|225| | | |230| | | | | | | | | | | |

<210> SEQ ID NO 38
<211> LENGTH: 698
<212> TYPE: DNA
<213> ORGANISM: Sorghum bicolor

<400> SEQUENCE: 38

| | |
|---|---|
|atggccgcag ctatcgacat gtacaagtac tacaacgcac accagatcgc ctcctcctcc|60|
|ccctcggatg aggagctcgc gaaagcactc gagccttta taacgagtgc ttcctcctcc|120|
|tctccctacc atcgctactc gtcttctcca tccatgtccc aagattctta catgcctaca|180|
|ccctcctaca ccagcttcgc cacctcgcct cttcccaccc ccgccgccac ctcctcctcc|240|
|tcctcgcctt tctcgcagct tccgccactc tactcgtcgc ttacgcggc gccgagcatg|300|
|gttgggcaga tgggcctgaa ccagctcggc ccggcccaga tccagcagat ccaggcccag|360|
|ttcatgttcc agcagcagca gcagcagcag agggtctgc acgcggcgtt cctgggcccg|420|
|cgggcgcagc cgatgaagca gtccggatcg ccgccgctgg cgccggcgca gtcgaagctg|480|
|taccgcggcg tccgccagcg ccactgggc aagtgggtgg cagagatccg cctccccaag|540|
|aaccgcaccc ggctgtggct cggcaccttc gacaccgccg aggacgcggc gctcgcctac|600|
|gacaaggccg ccttccgcct ccgcggcgac atggcgcgcc tcaacttccc ggccctccgc|660|
|cgcgacggcg cgcacctcgc cggcccgctc cacgcctc|698|

<210> SEQ ID NO 39
<211> LENGTH: 361
<212> TYPE: PRT
<213> ORGANISM: Solanum tuberosum

<400> SEQUENCE: 39

```
Met Ala Ala Met Asp Phe Trp Asn Ser Thr Ser Ser Val Asp Phe Gln
 1               5                  10                  15

Ser Ser Ser Glu Pro Val Thr Ser Gly Gly Glu Leu Met Glu Ala Leu
             20                  25                  30

Glu Pro Phe Met Lys Ser Ala Ser Ser Pro Ser Pro Pro Thr
         35                  40                  45

Thr Phe Pro Pro Val Phe Pro Ser Ser Ser Asp Phe Gln Ser Phe Pro
     50                  55                  60

Ser Phe Pro Pro Pro Thr Pro Thr Ile Ser Tyr Pro Tyr Thr Ser Ser
 65                  70                  75                  80

Phe Tyr Pro Ser Ser Gln Ser Thr Met Ser Ser Glu Val Cys Ser Thr
                 85                  90                  95

Ser Thr Glu Met Asn Ser Gln Ile Phe Ser Thr Arg Phe Ser Gly Tyr
            100                 105                 110

Gly Met Glu Gln Gln Gly Ser Ile Gly Leu Asn Gln Leu Thr Pro Ile
        115                 120                 125

Gln Ile Gln Gln Ile Gln Ala Gln Ile Asn Phe Gln Asn Gln Gln Gln
    130                 135                 140

Gln Gln Gln Met Met Leu Gln Thr Ala His His Ala Ser Thr Met Asn
145                 150                 155                 160

Phe Leu Ala Pro Lys Pro Val Pro Met Lys Gln Ser Gly Ser Pro Pro
                165                 170                 175

Lys Pro Ser Lys Leu Tyr Arg Gly Val Arg Gln Arg His Trp Gly Lys
            180                 185                 190

Trp Val Ala Glu Ile Arg Leu Pro Lys Asn Arg Thr Arg Leu Trp Leu
        195                 200                 205

Gly Thr Phe Asp Thr Ala Glu Ala Ala Leu Ala Tyr Asp Lys Ala
    210                 215                 220

Ala Tyr Met Leu Arg Gly Asp Phe Ala Arg Leu Asn Phe Pro Gln Leu
225                 230                 235                 240

Arg His Asn Gly Asn Leu Ile Gly Gly Asp Phe Gly Glu Tyr Asn Pro
                245                 250                 255

Leu His Ser Ser Val Asp Ala Lys Leu Lys Asp Ile Cys Gln Ser Leu
            260                 265                 270

Ala Gln Gly Lys Ser Ile Asp Ser Lys Lys Lys Thr Lys Gly Ser
        275                 280                 285

Ser Ala Glu Lys Ala Ala Val Val Lys Met Glu Glu Glu Ser Lys
    290                 295                 300

Thr Val Glu Val Gly Ser Glu Ser Asp Gly Ser Gly Ser Gly
305                 310                 315                 320

Gly Ser Ser Pro Val Thr Glu Leu Ile Phe Pro Glu Phe Thr Glu Glu
                325                 330                 335

Glu Thr Thr Trp Asp Met Ser Glu Asn Phe Leu Leu Gln Lys Tyr Pro
            340                 345                 350

Ser His Glu Ile Asp Trp Ala Ser Leu
        355                 360
```

<210> SEQ ID NO 40
<211> LENGTH: 1086
<212> TYPE: DNA
<213> ORGANISM: Solanum tuberosum

<400> SEQUENCE: 40

```
atggcagcta tggatttttg aatagtaca tcttctgtag attttcaatc atcatcagaa      60
cctgttactt ctggtggtga attaatggaa gctcttgaac cttttatgaa aagtgcttct     120
tcttctcctt ctcctccccc tactactttt cctcctgttt tcccttcttc ttcagatttc     180
caatcttttc cttcatttcc tcctccaact cctaccattt catatcccta cacttcttct     240
ttttacccat cttctcaatc tactatgagc tctgaggttt gttccacttc cacagagatg     300
aattcccaaa tcttttcaac tcggttttct gggtatggaa tggagcaaca gggttcaatt     360
gggttgaatc agttaacccc aatccagatc cagcaaattc aagcccaaat caacttccaa     420
aaccaacaac aacagcagca gatgatgtta cagactgcgc atcatgcttc caccatgaat     480
ttcttggcac caaagccggt tccaatgaag caatctgggt cgccaccaaa accctctaaa     540
ctctacagag gtgttagaca acgccactgg ggaaagtggg tcgctgagat ccgtttgcct     600
aagaatcgaa cccggctttg gcttggtaca tttgacaccg ctgaagaagc tgctttggct     660
tacgacaagg cggcgtatat gcttcgaggt gactttgctc gactgaactt cccccaactc     720
cgccacaacg gcaacctaat cggcggcgac tttggtgaat acaatccatt gcattcctct     780
gttgatgcta agctaaagga catatgccaa agcttggcac aggggaagag cattgactct     840
aagaagaaga aaaccaaagg gtcgtcggcg gagaaagcgg cggtggtgaa gatggaggaa     900
gaggagagca aaacggtaga agttggatcc gaaagtgacg gtcgggttc cgggtccggt     960
ggatcatcgc cggtaactga actgatattc ccggagttca ctgaggaaga gacaacttgg    1020
gacatgtcag aaaatttctt gttgcagaag tatccatctc atgaaattga ttgggcgtct    1080
ctataa                                                              1086
```

<210> SEQ ID NO 41
<211> LENGTH: 299
<212> TYPE: PRT
<213> ORGANISM: Solanum tuberosum

<400> SEQUENCE: 41

```
Met Phe Ser Gln Gly Tyr Ser Cys Phe Asn Asn Met Gly Val Ala Glu
  1               5                  10                  15

Thr Gly Ser Ile Gly Leu Asn His Leu Thr Pro Ser Gln Ile Leu Gln
             20                  25                  30

Ile Gln Ala Gln Ile Gln Phe Gln Asn Gln Gln Leu Leu Gln Leu
         35                  40                  45

His Gln Gln Gln Ser Leu Gly Leu Leu Thr Pro Thr Ser Thr Tyr
     50                  55                  60

Ser Lys Asn Leu Asn Ser Thr Asn Phe Leu Gly Met Lys Pro Val Pro
 65                  70                  75                  80

Met Lys Gln Thr Gly Gly Ala Ser Ser Gln Lys Ala Thr Lys Leu Tyr
                 85                  90                  95

Arg Gly Val Arg Gln Arg His Trp Gly Lys Trp Val Ala Glu Ile Arg
            100                 105                 110

Leu Pro Lys Asn Arg Thr Arg Leu Trp Leu Gly Thr Phe Asp Thr Ala
        115                 120                 125

Glu Glu Ala Ala Leu Ala Tyr Asp Lys Ala Ala Tyr Lys Leu Arg Gly
    130                 135                 140
```

```
Glu Phe Ala Arg Leu Asn Phe Pro His Leu Arg His Gln Leu Asn Asn
145                 150                 155                 160

Glu Phe Ser Pro Leu His Ser Ser Val Asp Ala Lys Leu Gln Ala Ile
            165                 170                 175

Cys Gln Ser Leu Ala Asn Pro Lys Ser Asp Leu Cys Ser Lys Ser
        180                 185                 190

Asn Ser Lys Pro Arg Lys Ser Lys Thr Ala Ala Ala Val Pro Val
        195                 200                 205

Asp Ser Asn Ser Ala Gln Glu Ser Ser Lys Ser Glu Ile Thr Ile
        210                 215                 220

Asp Asp Ser Leu Lys Gly Glu Phe Ser Tyr Pro Glu Asn Ala Asn Ile
225                 230                 235                 240

Lys Ile Glu Ala Ser Ser Ser Pro Ala Pro Ser Glu Glu Ser Ser
            245                 250                 255

Ser Ser Pro Glu Ser Asp Ile Thr Phe Leu Asp Phe Ala Glu Pro Pro
            260                 265                 270

Ser Phe Asp Glu Ser Glu Asn Phe Phe Leu Pro Lys Tyr Pro Ser Val
        275                 280                 285

Glu Ile Asp Trp Ala Ala Leu Cys Asn Leu Leu
        290                 295
```

<210> SEQ ID NO 42
<211> LENGTH: 900
<212> TYPE: DNA
<213> ORGANISM: Solanum tuberosum

<400> SEQUENCE: 42

```
atgttttctc aagggtattc atgttttaac aatatgggtg tagctgaaac aggttcaatt      60
gggcttaacc atctaacccc ttctcagata ttgcaaatcc aagctcagat ccaattccag     120
aatcaacagc aactactaca actgcatcaa caacaacaga gcttaggttt gttaacacct     180
acttcaacat attctaagaa tctgaattct acgaactttc ttggtatgaa accagtcccg     240
atgaagcaaa ctggtggtgc ttcttcacag aaggctacta agctttatcg tggagttaga     300
caacgccatt ggggtaaatg ggttgctgaa attagacttc taagaacag aaccaggctt      360
tggttaggca cttttgatac agctgaagaa gctgctttgg cttatgacaa agctgcttat     420
aagctaagag gagagtttgc tagacttaat tttccacatc taagacatca attaaataat     480
gaattctcgc ctttacattc ctccgttgat gctaaacttc aagccatttg ccaaagcttg     540
gctaatccca aatcagatga cttgtgttct aaatctaatt ccaagccaag aaagtccaaa     600
accgcagcag cagcagttcc agtggattca aattcagctc aagaatcttc atcaaagtcc     660
gaaatcacca tagatgattc attgaaagga gaattcagct atccagaaaa tgctaatatc     720
aagattgagg catcatcatc atctcctgca ccatctgagg aatcatcatc ttcgcctgag     780
tctgatatta cttttcttgga tttcgctgaa ccaccatctt tcgatgaatc agaaaatttc     840
ttcttaccca gtacccttc agtggagatt gattgggcag ctctttgtaa cttattgtag     900
```

<210> SEQ ID NO 43
<211> LENGTH: 374
<212> TYPE: PRT
<213> ORGANISM: Vitis vinifera

<400> SEQUENCE: 43

```
Met Ala Ala Ala Ile Asp Ile Tyr Ser Ser Ser Arg Thr Val Phe Ser
1               5                   10                  15
```

```
Glu Arg Glu Glu Leu Met Lys Ala Leu Glu Pro Phe Met Lys Gly Ala
            20                  25                  30

Ser Ser Thr Ser Ser Leu Thr Ser Pro Tyr Pro Tyr Pro Ser Thr Ser
        35                  40                  45

Ser Leu Ser Pro Pro Ser Thr Ser Ser Ser Ser Leu Pro Phe Phe Ser
    50                  55                  60

Tyr Pro Pro Asp Ser Thr Gln Pro Asn Met Tyr Pro Asp Phe Cys Ser
65                  70                  75                  80

Thr Ser Thr Thr His Met Phe Ser Gln Gly Phe Ser Gly Tyr Asp Gln
                85                  90                  95

Met Gly Leu Glu Gln Thr Arg Ser Ile Gly Leu Asn His Ile Thr Pro
            100                 105                 110

Ala Gln Ile Leu Gln Ile Gln Ala Gln Ile Gln Phe Gln Gln Gln Gln
        115                 120                 125

Gln Gln Arg Met Ala Ala Val Ala Thr Ala Ser Ser Ile Gln Asn Gln
130                 135                 140

Arg Leu Ser Gln Trp Gln Gln Gln His Thr Leu Asn Phe Leu Gly Pro
145                 150                 155                 160

Lys Ala Ile Pro Met Lys Gln Val Gly Thr Pro Lys Pro Ala Lys
                165                 170                 175

Leu Tyr Arg Gly Val Arg Gln Arg His Trp Gly Lys Trp Val Ala Glu
            180                 185                 190

Ile Arg Leu Pro Lys Asn Arg Thr Arg Leu Trp Leu Gly Thr Phe Asp
        195                 200                 205

Thr Ala Glu Glu Ala Ala Leu Ala Tyr Asp Lys Ala Ala Phe Lys Leu
    210                 215                 220

Arg Gly Glu Phe Ala Arg Leu Asn Phe Pro Asn Leu Arg His Gln Gly
225                 230                 235                 240

Ser Leu Val Ala Gly Glu Phe Gly Asp Tyr Lys Pro Leu His Ser Ser
                245                 250                 255

Val Asp Ala Lys Leu Gln Ala Ile Cys Gln Asn Leu Ala Ile Ser Gln
            260                 265                 270

Lys Gln Gly Asn Ser Gly Lys Pro Gly Leu Val Ala Asp Ala Lys Ile
        275                 280                 285

Glu Ser Ser Thr His Gln Ala Glu Met Val Leu Asp Asn Ser Ser Asp
    290                 295                 300

Pro Glu Ser Gly Phe Leu Gly Leu Glu Asp Cys Lys Val Glu Ile Ser
305                 310                 315                 320

Ser Ser Ser Ser Pro Ser Pro Ser Asp Glu Ser Ser Ala Gly Ser
                325                 330                 335

Ser Ser Pro Glu Ser Asp Ile Ser Phe Leu Asp Phe Thr Asp Ser Gln
            340                 345                 350

Trp Asn Asp Ser Glu Cys Leu Thr Leu Glu Lys Phe Pro Ser Val Glu
        355                 360                 365

Ile Asp Trp Ala Ser Ile
    370

<210> SEQ ID NO 44
<211> LENGTH: 1125
<212> TYPE: DNA
<213> ORGANISM: Vitis vinifera

<400> SEQUENCE: 44
atggcagcgg caatagatat atacagtagc agcaggacag tcttctcaga aagagaagaa    60
```

```
cttatgaaag cacttgaacc ttttatgaaa ggtgcttcat caacctcttc tttaacttct      120
ccttatccct atccctctac ttcatctctc tctcctcctt ctacttcttc ttcttctctt      180
cccttcttct cttatcctcc agactctaca cagcccaaca tgtaccctga tttttgctcg      240
acatcgacaa cccacatgtt ttctcaaggg ttctcaggtt acgaccaaat gggtcttgag      300
caaacacgtt caatcgggct aaaccacatc accccagctc agattctcca aattcaagcc      360
caaattcagt tccaacagca gcagcagcaa cgcatggctg ccgtggctac agcttcatct      420
atccagaacc agaggctaag ccaatggcag cagcaacata ccctaaactt cctcggcccc      480
aaagccatcc ccatgaagca ggttggaact ccccgaaac cagctaagct ctatcgagga       540
gtgagacagc ggcattgggg aaaatgggtt gcggagatca gacttcctaa gaaccgtacc      600
cgcctgtggc ttggcacttt cgatactgca gaagaagcgg ctttggccta tgataaggcc      660
gcttttaagc tcaggggaga gttcgccagg ctcaatttcc caaatctccg gcaccaaggg      720
tcacttgttg caggcgaatt cggggactac aagcctctcc actcctcagt ggatgcgaag      780
cttcaagcca tttgccaaaa cttggctatt tcgcagaaac aggggaattc agggaagcct      840
ggcctagtcg ccgatgcaaa gattgaaagt tccacccatc aggcggaaat ggtcttggat      900
aattcatcgg atcccgaatc ggggtttctg ggtttggagg attgtaaggt ggagatctca      960
tcatcatcgt catcccttc tccatccgac gaatcatctg cgggttcatc atcgcctgaa      1020
tcagatattt ccttcttgga tttcactgat tcacagtgga atgactcgga gtgcttgacg     1080
ttggagaagt ttccttctgt ggagattgat tgggcatcca tctag                     1125
```

<210> SEQ ID NO 45
<211> LENGTH: 221
<212> TYPE: PRT
<213> ORGANISM: Zea mays

<400> SEQUENCE: 45

```
Met Gln Tyr Ile Gln Ala Arg Leu His Leu Gln Arg Arg Gln Ala Gln
  1               5                  10                  15

Thr Ser Val Leu Gly Pro Arg Ala Gln Pro Met Lys Ala Ser Ala Ser
             20                  25                  30

Ala Ala Pro Ala Pro Ala Arg Pro Gln Lys Leu Tyr Arg Gly Val Arg
         35                  40                  45

Gln Arg His Trp Gly Lys Trp Val Ala Glu Ile Arg Leu Pro Arg Asn
     50                  55                  60

Arg Thr Arg Leu Trp Leu Gly Thr Phe Asp Thr Ala Glu Glu Ala Ala
 65                  70                  75                  80

Leu Ala Tyr Asp Gln Ala Ala Tyr Arg Leu Arg Gly Asp Ala Ala Arg
                 85                  90                  95

Leu Asn Phe Pro Asp Asn Ala Ala Ser Arg Gly Pro Leu His Ala Ser
            100                 105                 110

Val Asp Ala Lys Leu Gln Ser Leu Cys Gln Ser Ile Ala Ala Ser Lys
        115                 120                 125

Lys Gly Ala Lys Lys Pro Ala Ser Ala Ala Ala Ala Ser Ser
    130                 135                 140

Ala Pro Thr Ser Asn Cys Ser Ser Pro Ser Ser Asp Asp Ala Thr Ser
145                 150                 155                 160

Ser Cys Leu Glu Ser Ala Thr Glu Ser Ser Cys Pro Ser Pro Ser Pro
                165                 170                 175
```

```
Ser Ala Ser Pro Gly Pro Thr Val Pro Glu Met Gln Gln Leu Asp Phe
            180                 185                 190

Ser Glu Ala Pro Trp Asp Glu Ala Ala Gly Phe Ala Leu Thr Lys Tyr
        195                 200                 205

Pro Ser Tyr Glu Ile Asp Trp Asp Ser Leu Leu Ala Asn
    210                 215                 220

<210> SEQ ID NO 46
<211> LENGTH: 666
<212> TYPE: DNA
<213> ORGANISM: Zea mays

<400> SEQUENCE: 46
atgcagtaca tccaggcccg cctccacctg cagcgtcgcc aggcgcagac ctccgtgctg      60
ggcccgcgtg cccagcccat gaaggcgtcg gcgtccgcgg ccccgcccc ggcgcggccg     120 cagaagctgt accgcggcgt gcggcagcgg cactggggca agtgggtggc ggagatccgg     180
ctcccgcgca accgcacccg gctctggctc ggcaccttcg acaccgccga ggaggcggcg     240
ctggcctacg accaggccgc ctaccgcctg cgcggcgacg cggcgcgcct caacttcccc     300
gacaacgccg cctcccgcgg cccgctccac gcctccgtcg acgccaagct ccagagcctg     360
tgccagagca tcgccgcgtc caagaagggc gccaagaagc cggcctccgc cgcagctgcc     420
gcgtcgtcgt ccgcccccac cagcaactgc tcctcgccgt cgtccgacga cgcgacctcg     480
tcctgcctcg agtccgccac cgagtcctcg tgcccgtccc cgtcgccgtc cgcctcgcca     540
gggccgacgg tgccggagat gcagcagctg gacttcagcg aggcgccgtg ggacgaggcc     600
gccggcttcg cgctcaccaa gtacccgtcg tacgagatcg actgggactc cctcctcgcc     660
aattaa                                                              666
```

INCREASED WAX PRODUCTION IN PLANTS

CROSS REFERENCE TO RELATED APPLICATIONS

This application claims the benefit of U. S. Provisional Patent Application Ser. No. 60/619,801, filed Oct. 18, 2004, the entire contents of which are herein specifically incorporated by reference.

INCORPORATION BY REFERENCE OF SEQUENCE LISTING SUBMITTED ON A COMPACT DISC

The Sequence Listing is submitted on one compact disc (Copy 1), together with a duplicate thereof (Copy 2), each created on Oct. 18, 2005, and each containing one 87.0 kb file entitled "NBLE045US.APP.txt." The material contained on the compact disc is specifically incorporated herein by reference.

BACKGROUND OF THE INVENTION

1. Field of the Invention

The present invention relates generally to the field of molecular biology. More specifically, the invention relates to plant genes that activate wax biosynthesis and methods of use thereof.

2. Description of the Related Art

A cuticle layer covers most primary aerial organs of vascular plants and forms the contact zone between the plant and the environment (Kerstiens, 1996). Cuticular waxes are the major constituents of plant cuticle and play an important role in protecting aerial organs from damage caused by environmental stresses. Cuticular waxes are complex mixtures of very long chain fatty acids, alkanes, primary and/or secondary alcohols, aldehydes, ketones, esters, triterpenes, sterols, and flavonoids. Wax compounds can be embedded within the cutin polymer framework and form intracuticular wax. In many plants, however, more waxes are loaded outside of the cuticle membrane and form an epicuticular wax layer that give the plant surface a glaucous or grey appearance (Jenks and Ashworth, 1999; Post-Beittenmiller, 1996).

Plant cuticular wax biosynthesis and its loading to the plant surface is a complicated but actively regulated process (Broun et al., 2004; Jenks et al., 2002). Mutant analysis has contributed to the identification of some of the components and genes involved in wax deposition. Mutants with reduced wax accumulation or altered wax composition are in general characterized by a bright green phenotype which can be detected visually (Aarts et al., 1995). In *Arabidopsis*, 120 cuticular wax mutants representing a total of 31 recessive mutant loci have been identified, although dominant wax gene mutations have not been reported (Jenks et al., 2002). Wax-deficient mutants have also been identified in other species, including maize, sorghum, barley and rape (Kunst and Samuels, 2003).

Studies on the *eceriferum* (cer) mutants and T-DNA insertional mutants in *Arabidopsis* and glossy (gl) mutants in maize led to the identification and isolation of a number of wax-related genes. To date, 12 genes associated with wax production or regulation have been identified by molecular-genetic approaches. Among these genes, CER1, CER2, CER6/CUT1, 3-ketoacyl-CoA synthase (KCS1), FIDDLE-HEAD (FDH), GL1, GL8 and WAX2, may encode metabolic enzymes or be involved in transport of wax compounds (Aarts et al., 1995; Chen et al., 2003; Fiebig et al., 2000; Hansen et al., 1997; Millar et al., 1999; Negruk et al., 1996; Pruitt et al., 2000; St-Pierre et al., 1998; Todd et al., 1999; Xia et al., 1996, 1997; Xu et al., 1997), while CER3, GL2, GL15 and WIN1/SHINE1 appear to encode regulatory proteins (Aharoni et al., 2004; Broun et al., 2004; Hannoufa et al., 1996; Moose and Sisco, 1996; Tacke et al., 1995). Mutations in most of these genes showed altered wax accumulation (Jenks et al., 2002), cosuppression of some of the genes resulted in waxless stems in *Arabidopsis* (Millar et al., 1999; Todd et al., 1999), and overexpression of some of the genes in *Arabidopsis* mutant background complemented corresponding mutant phenotypes (Fiebig et al., 2000; Hannoufa et al., 1996). However, only limited information is available on the effects of overexpression of these genes in a wild-type background.

Overexpression of the condensing enzyme gene CER6/CUT1 under the control of CaMV35S promoter failed to promote wax deposition (Millar et al., 1999), while under the control of epidermis-specific CER6 promoter, CER6/CUT1 overexpression led to increased wax load in stems of *Arabidopsis* (Hooker et al., 2002). The only report of increased wax accumulation in leaf tissues of *Arabidopsis* was by the overexpression of a transcriptional activator (Broun et al., 2004; Aharoni et al., 2004).

Transcription factors are regulatory proteins that modulate gene expression through sequence-specific DNA binding and/or protein-protein interactions. They are capable of activating or repressing transcription of target genes as switches of the regulatory cascade. Most of the transcription factors are grouped into gene families according to their well-conserved DNA-binding domains.

APETALA 2 (AP2)/Ethylene-responsive element binding factors (ERF or EREBP) domain-containing transcription factor is a group of transcriptional regulators that are specifically found in plants (Okamuro et al., 1997; Riechmann et al., 2000). The AP2 domains in these proteins play a major role in specific promoter DNA sequence/element binding and transcriptional activation (Okamuro et al., 1997; Sakuma et al., 2002). This gene family has been further grouped into three major subfamilies and some smaller groups based on their functions and sequence similarities (Dubouzet et al., 2003; Riechmann et al., 2000). The AP2 subfamily genes (containing double AP2 domains) were thought to developmentally control flowering time in plants (Jofuku et al., 1994; Schultz and Haughn, 1991). The genes in ERF subfamily have been found to be involved in plant response to pathogen infection and mediate disease resistance (Chakravarthy et al., 2003; Gutterson and Reuber, 2004; Onate-Sanchez and Singh, 2002).

Recently, a new group of AP2 domain-containing transcription factors, dehydration-response element binding protein (DREB)/C-repeat binding factor (CBF), have been identified and characterized (Novillo et al., 2004; Shinozaki et al., 2003; Thomashow, 1999). They are mainly involved in the regulation of abiotic stress inducible genes; overexpression of some members from this subfamily in transgenic *Arabidopsis* induced a host of genes and conferred stress tolerance (Gilmour et al., 2000; Haake et al., 2002; Jaglo-Ottosen et al., 1998; Kasuga et al., 1999; Stockinger et al., 1997).

While the foregoing studies have provided a further understanding of the metabolism of wax in plants, the prior art has generally failed to provide wax biosynthesis activating genes, for example, that would yield drought tolerance. The identification of such genes would allow the creation of novel plants with improved phenotypes and methods for use thereof. There is, therefore, a great need in the art for the identification of plant genes that activate wax biosynthesis and methods for their use.

SUMMARY OF THE INVENTION

In one aspect, the invention provides an isolated nucleic acid sequence that activates wax biosynthesis. In certain embodiments, the nucleic acid sequence is operably linked to a heterologous promoter. In one embodiment, the nucleic acid sequence is further defined as selected from the group consisting of: (a) a nucleic acid sequence encoding the polypeptide of SEQ ID NO:1; (b) a nucleic acid sequence comprising the sequence of SEQ ID NO:2; (c) a nucleic acid sequence hybridizing to SEQ ID NO:2 under conditions of 5×SSC, 50% formamide and 42° C.; and (d) a nucleic acid sequence encoding a polypeptide with at least 65% amino acid identity to SEQ ID NO:1.

In another aspect, the invention provides an isolated nucleic acid sequence that activates wax biosynthesis. In certain embodiments, the nucleic acid sequence is operably linked to a heterologous promoter. In one embodiment, the nucleic acid is selected from the group consisting of: (a) a nucleic acid sequence encoding the polypeptide of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, and/or SEQ ID NO:45; (b) a nucleic acid sequence comprising the sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:33, SEQ ID NO:36, SEQ ID NO:38, SEQ ID NO:40, SEQ ID NO:42, SEQ ID NO:44, and/or SEQ ID NO:46; (c) a nucleic acid sequence hybridizing to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:33, SEQ ID NO:36, SEQ ID NO:38, SEQ ID NO:40, SEQ ID NO:42, SEQ ID NO:44, and/or SEQ ID NO:46 under conditions of 5×SSC, 50% formamide and 42° C.; and (d) a nucleic acid sequence encoding a polypeptide with at least 65% amino acid identity to SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, and/or SEQ ID NO:45.

In still yet another aspect, the invention provides a recombinant vector comprising an isolated nucleic acid sequence provided herein. The recombinant vector may comprise at least one additional sequence chosen from the group consisting of: a regulatory sequence, a selectable marker, a leader sequence and a terminator. The additional sequence may be a heterologous sequence. The promoter may be an epidermis specific promoter, developmentally-regulated, organelle-specific, inducible, tissue-specific, constitutive, cell-specific, seed-specific or germination-specific promoter. Such an epidermis-specific promoter directs expression preferentially to the plant surface, for example, to leaves or the leaf surface. The promoter may also be drought-inducible promoter. The recombinant vector may be defined as an isolated expression cassette.

Yet another aspect of the invention is an isolated polypeptide having at least 65% amino acid identity to the amino acid sequence of SEQ ID NO:1 or a fragment thereof having wax biosynthesis activity. Also provided is an isolated polypeptide comprising the amino acid sequence of SEQ ID NO:1 or a fragment thereof having wax biosynthesis activity.

In still yet another aspect, the invention provides a transgenic plant transformed with a selected DNA comprising a nucleic acid sequence provided by the invention. The plant may be a dicotyledonous or monocotyledonous plant, and may be an R0 transgenic plant and/or further defined as a progeny plant of any generation of an R0 transgenic plant that has inherited the selected DNA from the R0 transgenic plant. Seed of such a transgenic plant comprising the selected DNA are also provided, as are cells of such a plant. Such a cell may express a protein encoded by the selected DNA and may have inherited the selected DNA from a progenitor of the cell and/or been transformed with the selected DNA. The host cell may be a plant cell.

In still yet another aspect, a method of increasing drought tolerance in a plant is provided comprising increasing leaf wax production in the plant. The method may comprise altering the wax content or composition of a plant by introducing into the plant a recombinant vector provided herein, wherein the nucleic acid is expressed in the plant. The coding sequence may be operably linked to a heterologous promoter functional in the plant and may be in sense orientation. Wax biosynthesis may be up-regulated in the plant and the plant may exhibit increased tolerance to water deficit relative to a plant of the same genotype lacking the coding sequence. Introducing the coding sequence may comprise plant breeding and/or genetic transformation.

In still yet another aspect, the invention provides a method of making food for human or animal consumption comprising: (a) obtaining the plant of claim 13; (b) growing the plant under plant growth conditions to produce plant tissue from the plant; and (c) preparing food for human or animal consumption from the plant tissue. Preparing food may comprise harvesting the plant tissue. The food may be starch, protein, meal, flour or grain.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1. Alignment of *Medicago truncatula* WXP1, Mt77128 (WXP2 thereafter) and 11 other AP2 domain-containing transcription factors that either have been characterized or are related (SEQ ID NOS:47-51; SEQ ID NO:5, SEQ ID NO:7, SEQ ID NO:1; SEQ ID NOS:52-55). The alignment consists of the following predicted protein sequences: *Arabidopsis* WIN1/SHINE1 and At5g11190 (Aharoni et al., 2004; Broun et al., 2004), *Arabidopsis ERF*1 (Fujimoto et al., 2000), tomato ERF-like gene LePti4 (Gu et al., 2002), tobacco ERF-like gene NtERF1 (Ohme-Takagi and Shinshi, 1995), WXP1 and its parolog, Mt77128 (WXP2, deduced amino acid sequence based on TIGR sequence TC77128), most similar WXP1 sequence found in *Arabidopsis* AtRAP2.4 (At1g78080), and characterized sequences *Arabidopsis* CBF1 (Stockinger et al., 1997), CBF2 (Novillo et al., 2004), CBF3 (Gilmour et al., 2000), and CBF4 (Haake et al., 2002). Sequences were aligned with CLUSTAL W using default parameters. Identical and similar amino acid residues are shown on black and gray background, respectively. Gaps required for optimal alignment are indicated by dashes. AP2 domains aligned with the Pfam seed sequences (//pfam.wustl.edu/cgi-bin/getdesc?name=AP2) are indicated by stars under the sequences.

DETAILED DESCRIPTION OF THE INVENTION

Figure 2:
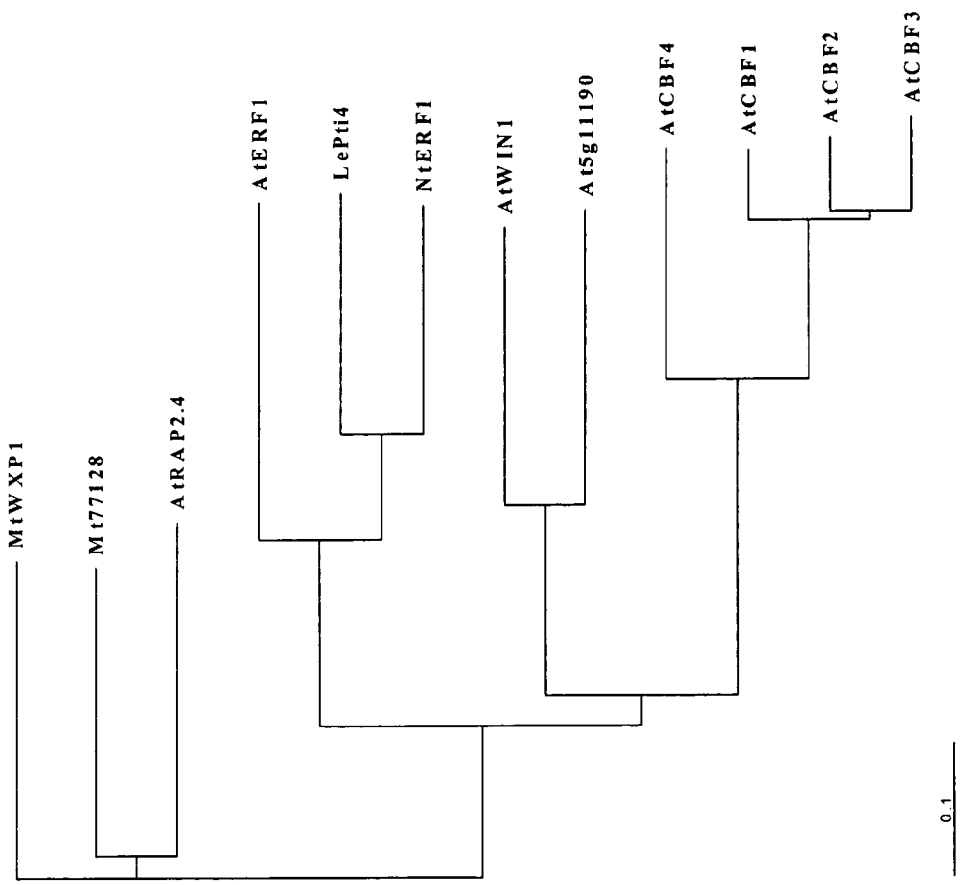
FIG. 2. Phylogenetic analysis of WXP1 and 11 other AP2 domain-containing transcription factors that either have been characterized or are related. The root tree was constructed using CLUSTAL W and showed in TreeView.

The invention overcomes the limitations of the prior art by providing coding sequences that activate wax biosynthesis. As very limited information is available on plant genes conferring increased wax production, the invention represents a major advance and allows the creation of transgenic plants modified for increased plant wax accumulation. By introduction of one or more heterologous wax biosynthesis activating nucleic acid sequences into a plant, wax biosynthesis and environmental stress tolerance may be up-regulated in accordance with the invention.

Drought tolerance in particular is an important target for improvement in plants and for the implementation of sustainable farming techniques. Since cuticular waxes play a pivotal role in limiting transpirational water loss across the plant surface, genetic engineering of plant waxes represents a significant advance for increasing tolerance to environmental stresses in crops of agronomic importance (Millar et al., 1999; Vogg et al., 2004).

The inventors report the characterization and transgenic expression of novel genes that activate wax production. Overexpression of a gene designated WXP1 under the control of CaMV35S promoter in particular was shown to increase cuticular wax loading on leaf surfaces of transgenic alfalfa. Furthermore, it was demonstrated that the transgenic plants had reduced water loss, enhanced drought tolerance and reduced chlorophyll leaching. The plants with increased cuticular waxes showed delayed wilting after watering was ceased and better recovery when re-watered. To the inventors' knowledge, this is the first report of improved drought tolerance by genetic manipulation of wax biosynthesis in an agronomically important species.

Scanning electron microscopy on transgenic alfalfa plant tissues revealed earlier accumulation of wax crystals on the adaxial surface of newly expanded leaves and higher densities of wax crystalline structures on both the adaxial and abaxial surfaces of mature leaves. GC-MS analysis revealed that total leaf wax accumulation per surface area increased 29.6-37.7% in the transgenic alfalfa lines, and the increase was mainly contributed by C30 primary alcohol.

It was further demonstrated that overexpression of WXP1 and a second gene designated WXP2 under the control of a strong constitutive promoter led increased cuticular wax loading on leaf surfaces of transgenic Arabidopsis. Total leaf wax content per gram of fresh weight in 3-week-old transgenic Arabidopsis plants expressing WXP1 and WXP2 increased by 32.36% and 16.96%, respectively. In 6-week-old transgenic Arabidopsis plants expressing WXP1 and WXP2, leaf wax accumulation per surface area averagely increased by 27.51% and 23.61%, respectively.

I. Plant Transformation Constructs and Nucleic Acids

In one aspect of the invention, plant transformation vectors comprising one or more coding sequences that activate wax biosynthesis are provided. Two exemplary coding sequences for use with the invention are the *Medicago truncatula* wax biosynthesis activating sequences of SEQ ID NO:2 and SEQ ID NO:6. Such coding sequences may encode polypeptides having the amino acid sequences of SEQ ID NO:1 and SEQ ID NO:5. Sequences that hybridize to this coding sequence under stringent conditions are also provided by the invention. An example of such conditions include a wash of 5×SSC, 50% formamide and 42° C. for 10 minutes. It will be understood by those of skill in the art that stringency conditions may be increased by increasing temperature, such as to about 60° C. or decreasing salt, such as to about 1×SSC, or may be decreased by increasing salt, for example to about 10×SSC, or decreasing temperature, such as to about 25° C.

Further provided by the invention are polypeptides encoded by coding sequences that activate wax biosynthesis. In specific embodiments, such polypeptides may be defined as having at least 45%, 60%, 70, 80%, 90%, 95%, 98% or 99% sequence identity to a polypeptide sequence of SEQ ID NO:1 and SEQ ID NO:5. In further embodiments, the invention provides nucleic acids encoding these polypeptides.

Still further contemplated for use with the invention for modification of plant wax biosynthesis are additional sequences from species including *Medicago truncatula* (WXP2; SEQ ID NO:5 and SEQ ID NO:6), *Arabidopsis thaliana* (AtTC261112; SEQ ID NO:7 and SEQ ID NO:8) (AtTC262267; SEQ ID NO:9 and SEQ ID NO:10), cotton (CTC28125; SEQ ID NO:11 and SEQ ID NO:12) (CTC37888; SEQ ID NO:13 and SEQ ID NO:14) (CTC38239; SEQ ID NO:15 and SEQ ID NO:16), soybean (GmTC215663; SEQ ID NO:17 and SEQ ID NO:18) (GmTC215664; SEQ ID NO:19 and SEQ ID NO:20) (GmTC225042; SEQ ID NO:21 and SEQ ID NO:22) (GmTC225047; SEQ ID NO:23 and SEQ ID NO:24) (GmTC228532; SEQ ID NO:25 and SEQ ID NO:26), tomato (LeTC137279; SEQ ID NO:27 and SEQ ID NO:28) (LeTC148534; SEQ ID NO:29 and SEQ ID NO:30), *Lotus japonicus* (Partial, LjTC16026; SEQ ID NO:31 and SEQ ID NO:32), lettuce (LsTC8978; SEQ ID NO:33 and SEQ ID NO:34), poplar (PplTC2364; SEQ ID NO:35 and SEQ ID NO:36), sorghum (SbTC103215; SEQ ID NO:37 and SEQ ID NO:38), potato (StTC102572; SEQ ID NO:39 and SEQ ID NO:40) (StTC104330; SEQ ID NO:41 and SEQ ID NO:42), grape (VvTC45892; SEQ ID NO:43 and SEQ ID NO:44) and maize (ZmTC270551; SEQ ID NO:45 and SEQ ID NO:46).

In certain embodiments, the invention therefore provides an isolated polypeptide comprising the amino acid sequence of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, and/or SEQ ID NO:45 and biologically active fragments thereof. Also provided polypeptides having at least about 45, 55, 65, 70, 80, 90, 95 98 and about 99% amino acid identity to these sequences are provided. Still further provided are nucleic acids encoding any of these polypeptides.

In one embodiment of the invention, such a nucleic acid sequence may comprise the nucleic acid sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:33, SEQ ID NO:36, SEQ ID NO:38, SEQ ID NO:40, SEQ ID NO:42, SEQ ID NO:44, and/or SEQ ID NO:46. The invention also provides nucleic acids hybridizing to these nucleic acid sequences under wash conditions of 5×SSC, 50% formamide and 42° C. for 10 minutes.

Nucleic acids provided by the invention include those encoding active wax biosynthesis fragments. Those of skill in the art will immediately understand in view of the disclosure that such fragments may be prepared by placing fragments of wax biosynthesis activating sequences in frame in an appropriate expression vector, for example, comprising a plant promoter. Using the assays described in the working examples, wax biosynthesis activity can be confirmed for any given fragment. Fragments of nucleic acids may be prepared according to any of the well known techniques including partial or complete restriction digests and manual shearing.

Sequences provided by the invention may be defined as encoding a transcription factor that increases wax biosynthesis. In certain further aspects of the invention, a plant wax biosynthesis gene may be characterized as from a monocotyledonous or dicotyledonous plant. Coding sequences may be provided operably linked to a heterologous promoter, in either sense or antisense orientation. Expression constructs are also provided comprising these sequences, including antisense oligonucleotides thereof, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with coding sequences that activate wax biosynthesis. The wax biosynthesis activating sequence may be provided with other sequences and may be in sense or antisense orientation with respect to a promoter sequence. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with a wax biosynthesis activating sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise coding sequence which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components that may be included with plant transformation vectors are as follows.

A. Regulatory Elements

Exemplary promoters for expression of a nucleic acid sequence in plants include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a wax biosynthesis activating sequence is used. In certain aspects of the invention, it may be beneficial to use an epidermis-specific promoter or a promoter inducible by environmental stress, such as water deficit.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that wax biosynthesis activating sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of sense or antisense wax biosynthesis coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al, 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

II. Methods of Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al, 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually will grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations.

These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected wax biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

Wax Biosynthesis Gene: A nucleic acid sequence that confers wax biosynthesis when expressed in a plant.

Wax Biosynthesis Activating Sequences: A nucleic acid sequence that confers activation of wax biosynthesis when expressed in a plant.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Sequence Analysis and Expression Pattern of WXP1 and WXP2

Figure 1:
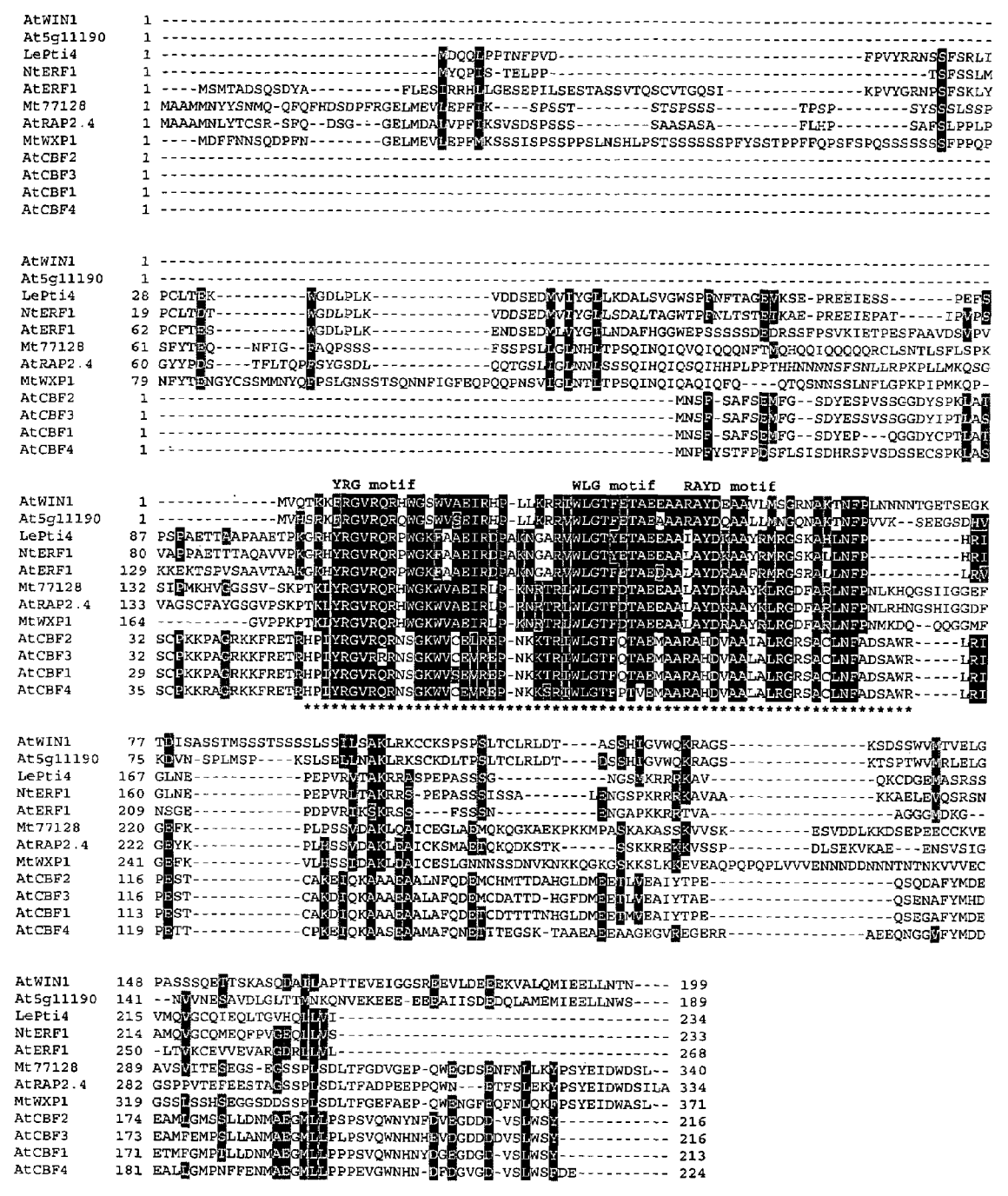

A number of AP2 domain-containing transcription factor genes were identified from *M. truncatula* and characterized by sequence alignment, northern hybridization analysis and transgenic overexpression. One of the genes, WXP1, has an open reading frame (ORF) encoding 371 aa with an estimated molecular mass of 41.3 kD and a theoretical pI of 5.55. It is one of the longest peptides among 80 AP2 domain-containing transcription factors identified in *M. truncatula*. Another gene, WXP2, has an open reading frame (ORF) encoding 340 aa with an estimated molecular mass of 37.8 kD and a theoretical pI of 5.36. The deduced amino acid sequences of these genes contain one conserved AP2 domain when analyzed by Pfam (Bateman et al., 2002). When aligned with well-characterized AP2 domain-containing transcription factors from *Arabidopsis* (At), tomato (Le) and tobacco (Nt), the AP2 domain of WXP1 and WXP2 shared high similarity to that of the other proteins (FIG. 1). All these AP2 domains have a 100% identical WLG motif in the middle and an extremely conserved YRG motif in the front. But they are clearly divided into three groups by the diversification of the RAYD, LAYD and RAHD motifs. WXP1 and WXP2 contain LAYD motifs that are found in three ERFs (LePti4, NtERF1, AtERF1), and AtRAP2.4 (At1g78080) (FIG. 1).

Comparison of WXP1 to predicted protein sequences of AP2 domain-containing transcription factors from different species revealed that Mt77128 (WXP2) from *M. truncatula* is the closest homolog with 53.4% identity to WXP1, and AtRAP2.4 from *Arabidopsis* is the closest ortholog with 48.8% identity to WXP1. When compared with amino acid sequences of other stress or wax inducing genes, WXP1 is only 19.4-22.8% identical to AtCBFs, 16.7% to AtDREB2A, 20.6% to AtDREB2B, 22.8-25.3% to the three ERFs, 28.6% to AtWIN1 and 14.0% to ZmGlossy15. Phylogenetic analysis showed that WXP1 and WXP2 are distinct from most of the known AP2 domain transcription factors based on analysis of their complete protein sequences (FIG. 2).

Figure 3:
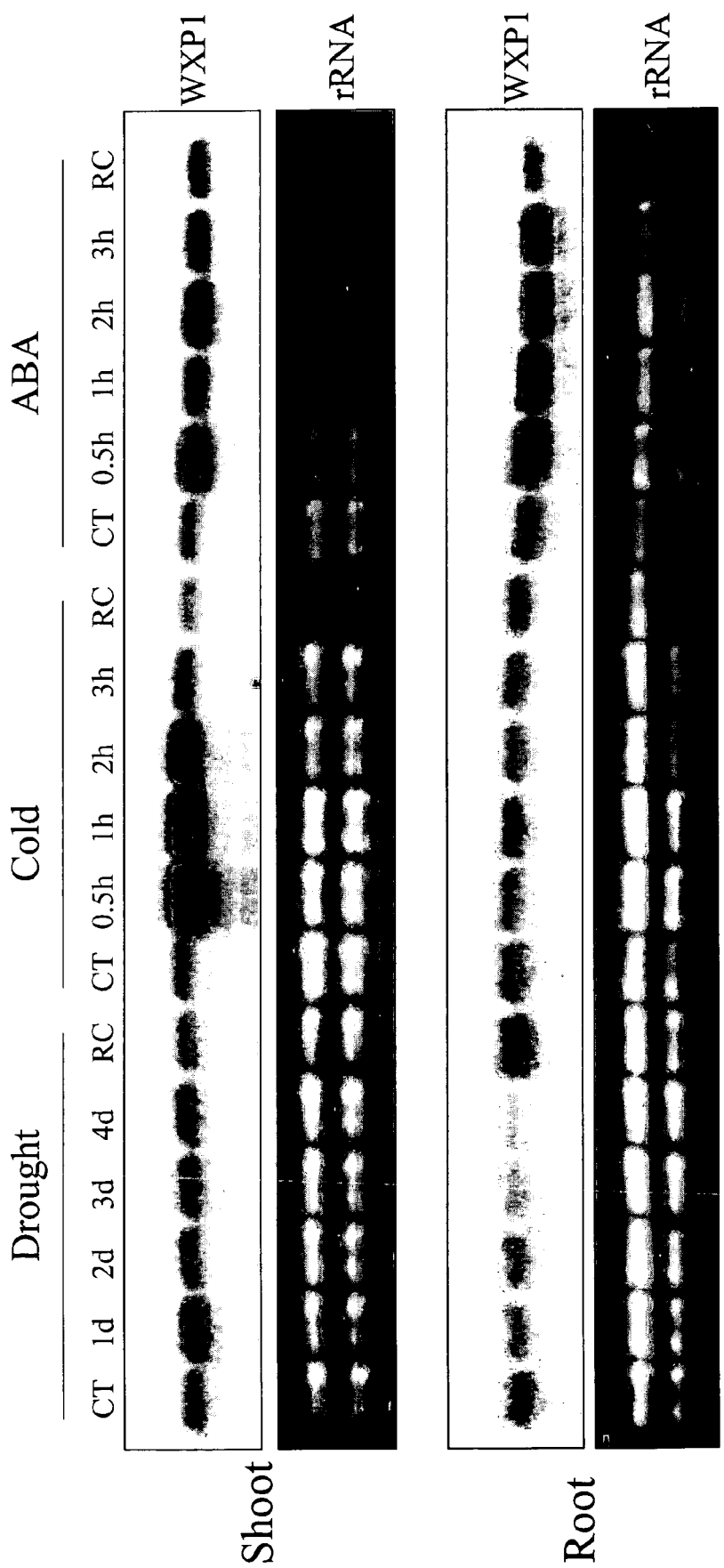
FIG. 3. Changes of WXP1 transcript level in *Medicago truncatula* in response to drought, cold and ABA treatment. CT, control; RC, recovered 24 hrs after transferring the plants back to normal growth conditions; d, days after watering was ceased; h, hours after treatment was applied.

The expression pattern of the WXP1 gene in *M. truncatula* may also be detected by northern hybridization analysis. Drought treatment slightly induced its expression in shoot tissues but suppressed its expression in root tissues (FIG. 3). WXP1 transcript in shoot was quickly induced to a high level after transferring plants to 4° C., however, no such change was observed in root after the same cold treatment (FIG. 3). Abscisic acid (ABA) treatment induced WXP1 expression in both shoot and root in a relatively short time (FIG. 3). The induction or suppression of WXP1 in *M. truncatula* was reversible, as transcription would go back to normal levels when the stimuli were withdrawn.

Example 2

Growth and Development of Transgenic Alfalfa Plants Overexpressing WXP1

The ORF of WXP1 was placed under the control of CaMV 35S promoter by replacing the gusA gene of the binary vector pCAMBIA3301. The resulting vector pC35S-WXP1 was introduced into alfalfa by *Agrobacterium*-mediated transformation and 60 independent transgenic plants were produced. PCR screening indicated that more than 98% of the regenerated plants contained the target gene, and northern hybridization analysis revealed that 60% of the plants expressed the transgene with various mRNA levels. To facilitate the analysis, three transgenic lines (18, 41, 47) were focused on for agronomic and biochemical analysis and five lines for gene regulation assay. These lines were selected because they showed different transgene expression levels. Lines 4, 18, 41, 47 and 45 showed very low, low, medium, high, and extremely high levels of WXP1 expression, respectively (see FIG. 15). All the lines were vegetatively propagated by cuttings of young shoots.

Figure 4:
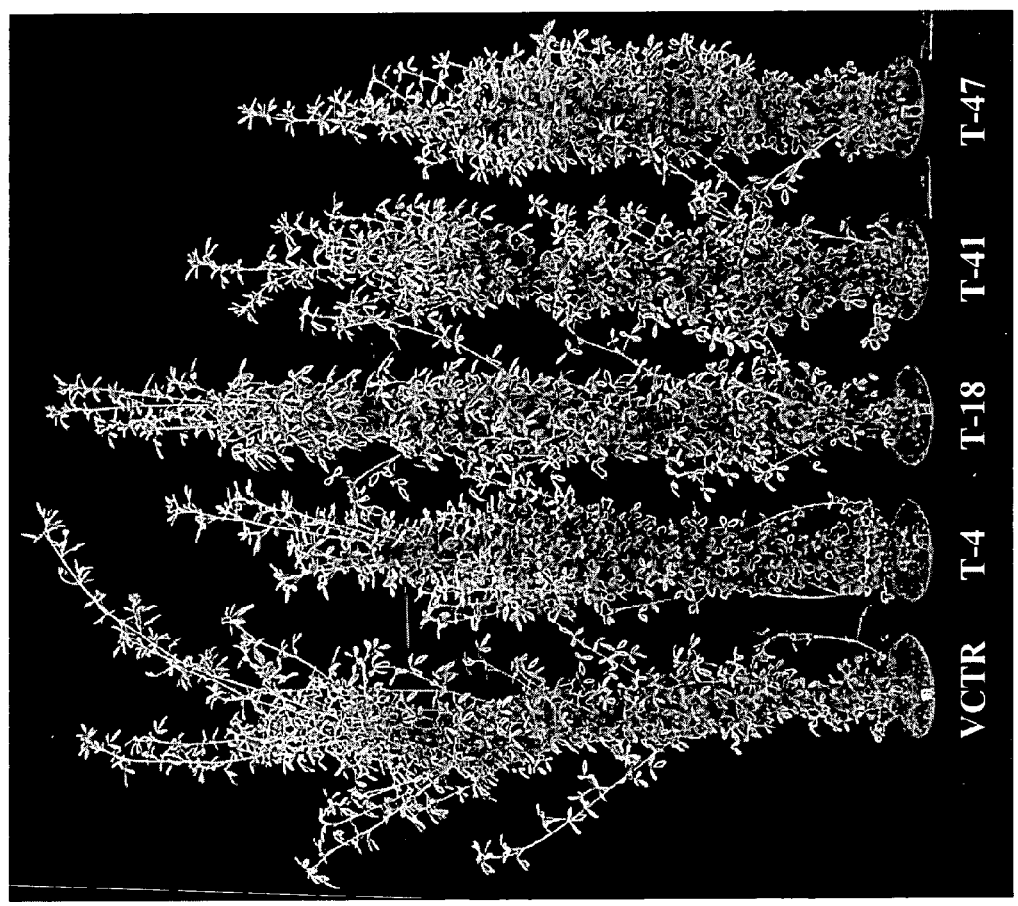
FIG. 4. Phenotype of WXP1 transgenic alfalfa lines after 60 days of growth in the greenhouse. VCTR, empty vector control; T, transgenic lines overexpressing WXP1.
Figure 5:
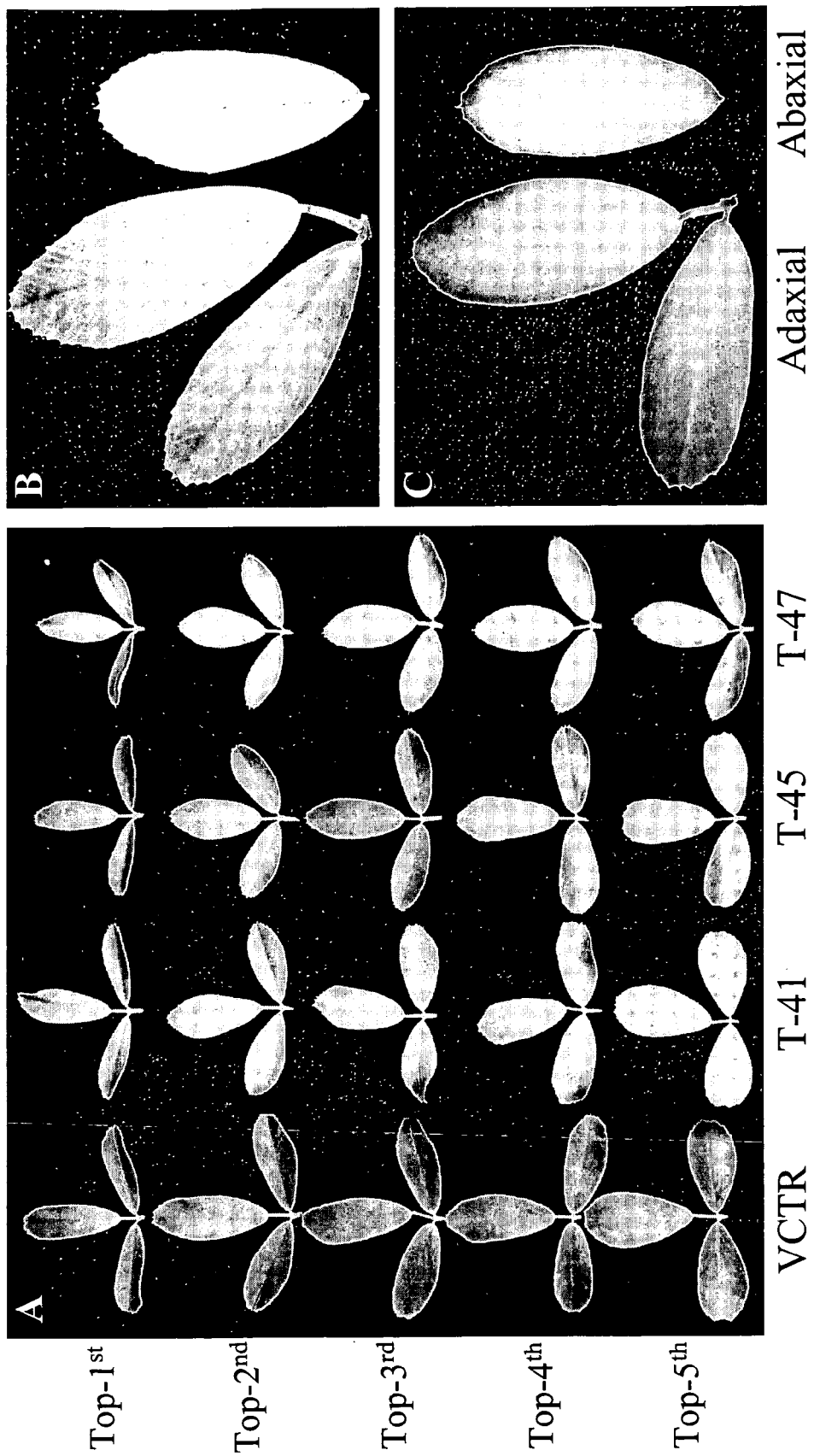
FIG. 5. Leaf surfaces of transgenic alfalfa plants overexpressing WXP1. (A) Adaxial surface of transgenic and control plants. (B) Adaxial and abaxial sides of the same trifoliate from control plant. (C) Adaxial and abaxial sides of the same trifoliate from transgenic line 47. VCTR, empty vector control; T, transgenic lines overexpressing WXP1.
Figure 11:
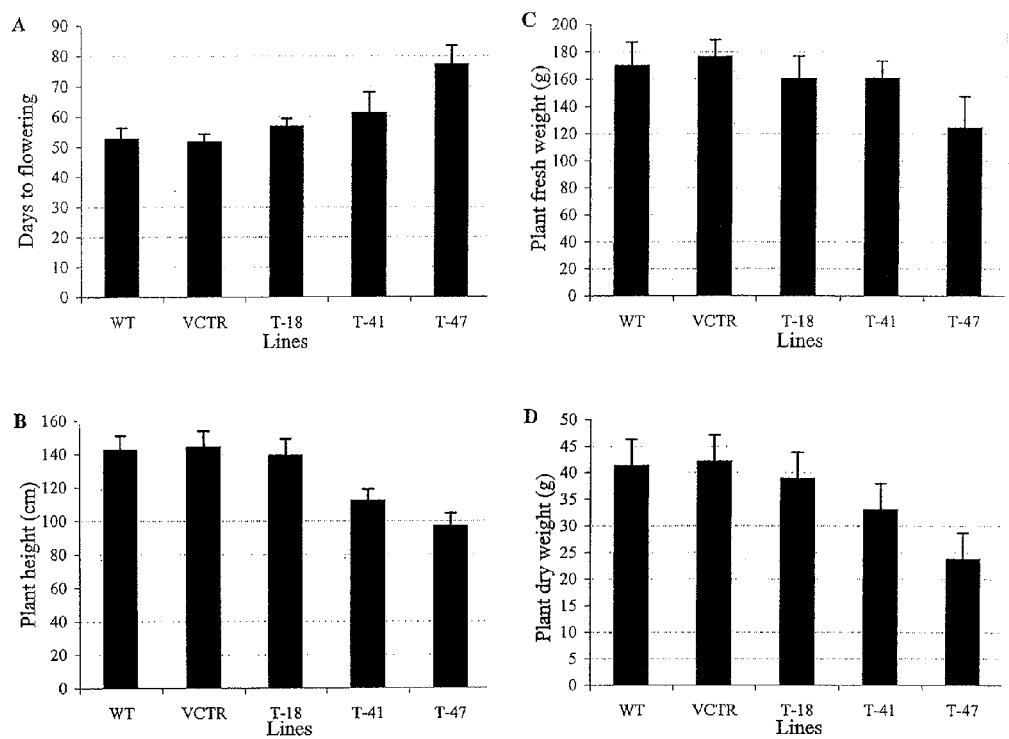
FIG. 11. Growth and development of transgenic alfalfa plants overexpressing WXP1. (A) Days to flowering after transplanting. (B) Plant height. (C) Plant fresh weight. (D) Plant dry weight. WT, wild type; VCTR, empty vector control.

Even though the overexpression of WXP1 did not result in severe growth retardation, which was typical in AP2 domain-containing gene overexpressed *Arabidopsis* (Broun et al., 2004; Gilmour et al., 2000; Jaglo-Ottosen et al., 1998; Liu et al., 1998), the alfalfa transgenic lines tended to grow relatively slowly (FIG. 4). When compared with wild-type and empty vector control plants, flowering time of the transgenic plants was delayed 5-28 d (FIG. 11A), height of the transgenic lines were 2-32% shorter at flowering time (FIG. 11B), and trifoliates of the transgenic lines were smaller (FIG. 5A). Even though the transgenic lines produced more branches, fresh and dry matter production of the transgenic lines decreased 5.6-26.8% and 6.7-42.7%, respectively (FIGS. 11C and 11D).

The most striking phenotypic change in the WXP1 overexpressed alfalfa plants was the more glaucous appearance in the leaves (FIG. 5A). The increased glaucousness occurred in most of the transgenic lines with low to extremely high WXP1 overexpression levels, represented by line 18, 27, 41, 47, 33, and 45.

Observation of leaf surfaces under a stereomicroscope with strong light indicated that glaucousness was added to both sides of the WXP1 overexpressed alfalfa leaves; however, the change of glaucous appearance on the adaxial and abaxial surfaces of the transgenic lines was not equal. By observing leaflets excised from the same trifoliate, the adaxial side showed less light refraction and thus less glaucous than the abaxial side in control leaflets (FIG. 5B), however, the difference between the two sides was drastically reduced in transgenic leaflets (FIGS. 5C). Compared with control leaflets, the transgenic leaflets showed more obvious increase of glaucousness in the adaxial surface than the abaxial side (FIGS. 5B and 5C). The results indicate that the difference in glaucousness between transgenic and control lines was more prominent on the adaxial side than that on the abaxial side.

Example 3

Impact of WXP1 Overexpression on Cuticular Wax Production in Transgenic Alfalfa

To confirm the increased glaucous appearance on leaves was caused by alteration of epicuticular wax production, WXP1 transgenic alfalfa lines and empty vector control plants were examined by scanning electron microscopy (SEM). When the adaxial and abaxial surfaces of the same leaflet from a control plant were compared, the time of epicuticular wax loading, wax crystal type, crystal size, and crystal density was different between the two sides (FIGS. 6A, 6C, 6E and 6G). It was evident that the abaxial surface started loading epicuticular wax earlier than the adaxial surface (FIGS. 6A and 6C). Comparison of leaf epicuticular wax crystalline pattern between control and transgenic lines showed that overexpression of WXP1 in alfalfa resulted in increased wax loading on both sides and earlier accumulation of epicuticular waxes on the adaxial surface. When the new leaf became fully expanded (top-$1^{st}$), there were no visible wax crystals on the adaxial leaf surface of control plants (FIG. 6A), in contrast, wax crystal structures were already developed on the adaxial leaf surface of transgenic plants (FIG. 6B).

Figure 6:
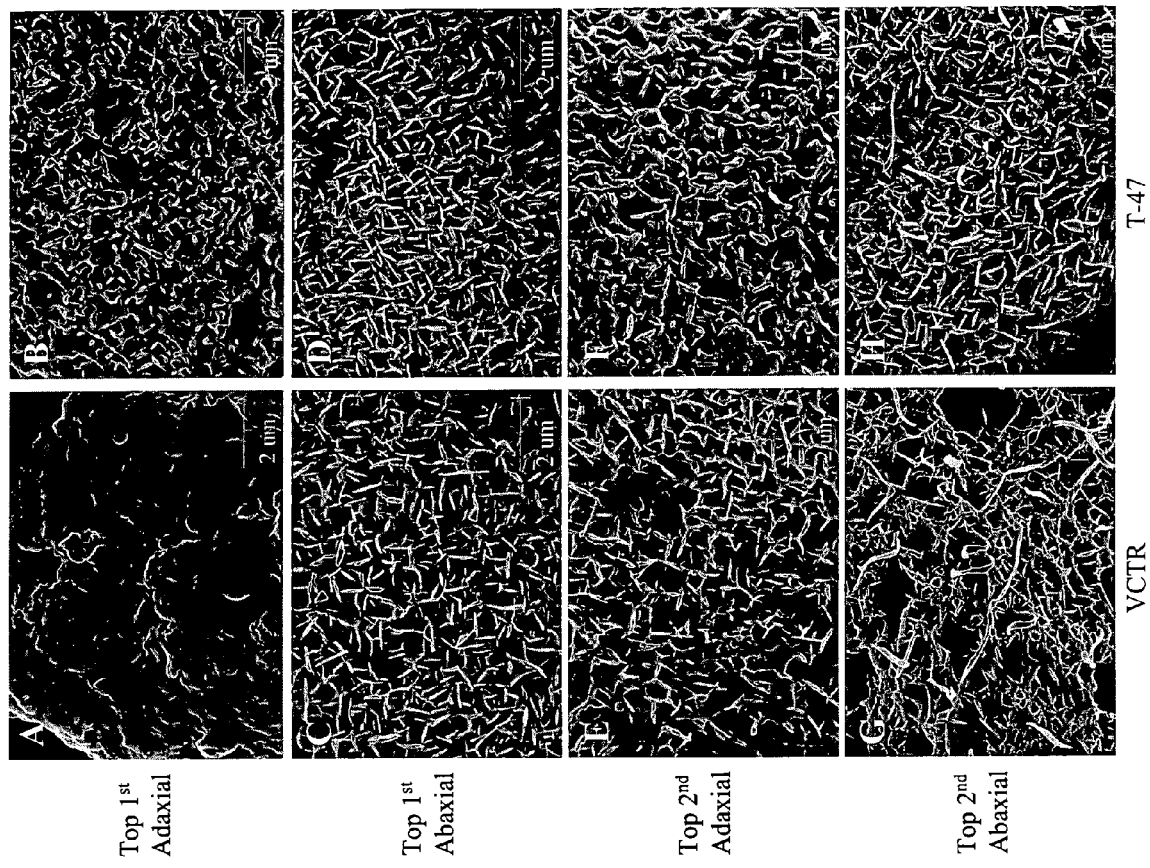
FIG. 6. Epicuticular wax crystallization patterns on adaxial and abaxial leaf surfaces of transgenic and control alfalfa plants viewed by scanning electron microscope. (A,C,E,G) empty vector control (VCTR). (B, D, F, H) Transgenic line 47. Images were taken at ×8,000 magnification.
Figure 12:
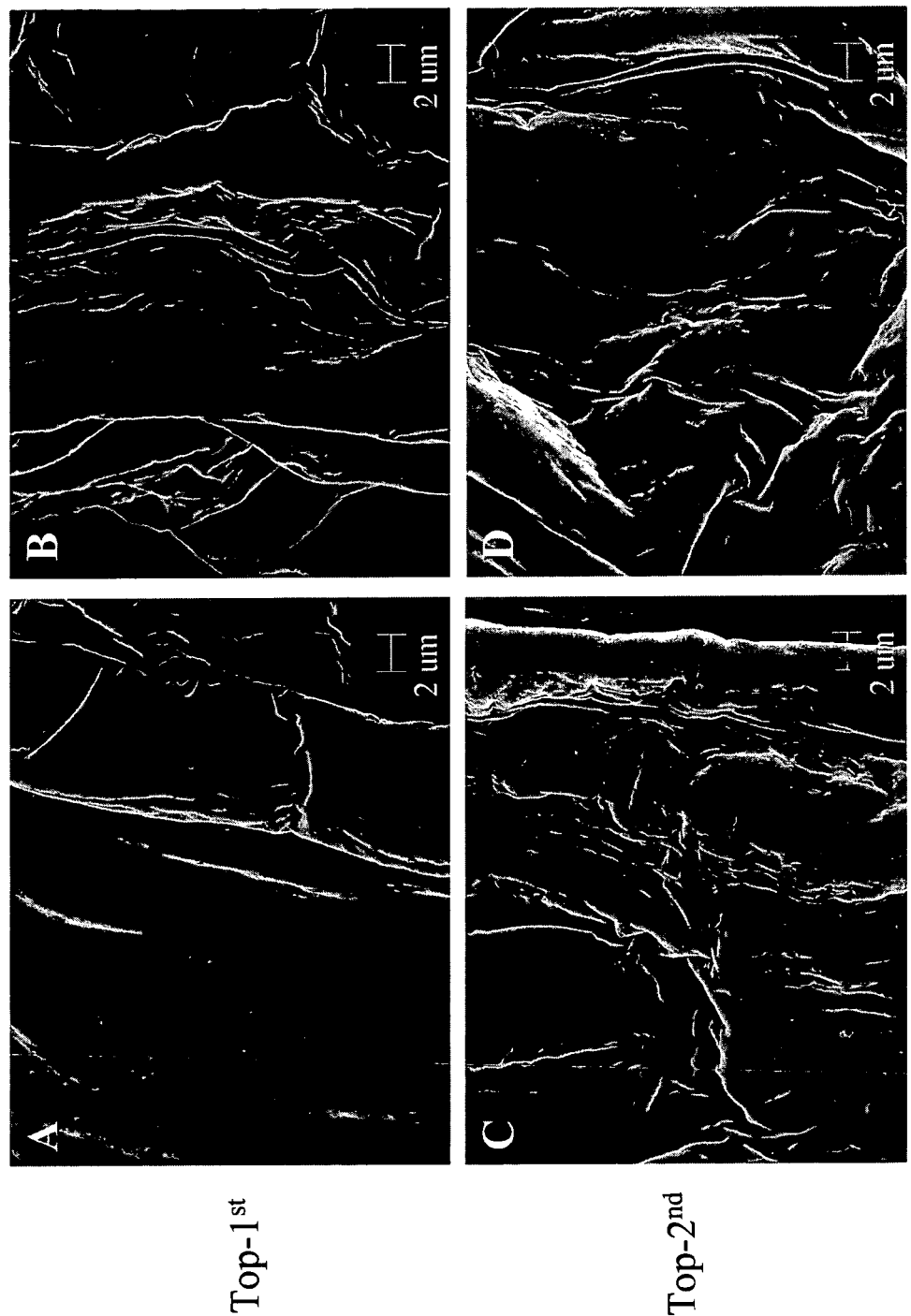
FIG. 12. Scanning electron microscopy of stem surfaces of top-1st and top-2nd internodes of vector control (A, C) and transgenic line T-47 (B, D). Images were taken at ×8,000 magnification.

Wax crystal density of newly expanded leaf showed some difference on the abaxial side, with a better coverage of wax crystals in transgenics than in the control plant (FIGS. 6C and 6D). For the top-$2^{nd}$ trifoliate, differences in wax crystal density on the adaxial leaf surfaces were apparent between the transgenic and control plants, with much more wax crystals present in the transgenic plant (FIGS. 6E and 6F). On the abaxial surface of the top-$2^{nd}$ trifoliate, the long coiled crystalline structure in transgenic line was reduced, but the loss of the long coiled crystals was complemented by the increase in density of tubular and plate-like wax crystals (FIGS. 6G and 6H). Thus the SEM examination is in agreement with the increased leaf surface glaucous appearance observed under light microscope. Stem surfaces of both control and transgenic alfalfa lines did not show visible wax crystalline structure (FIG. 12).

Figure 7:
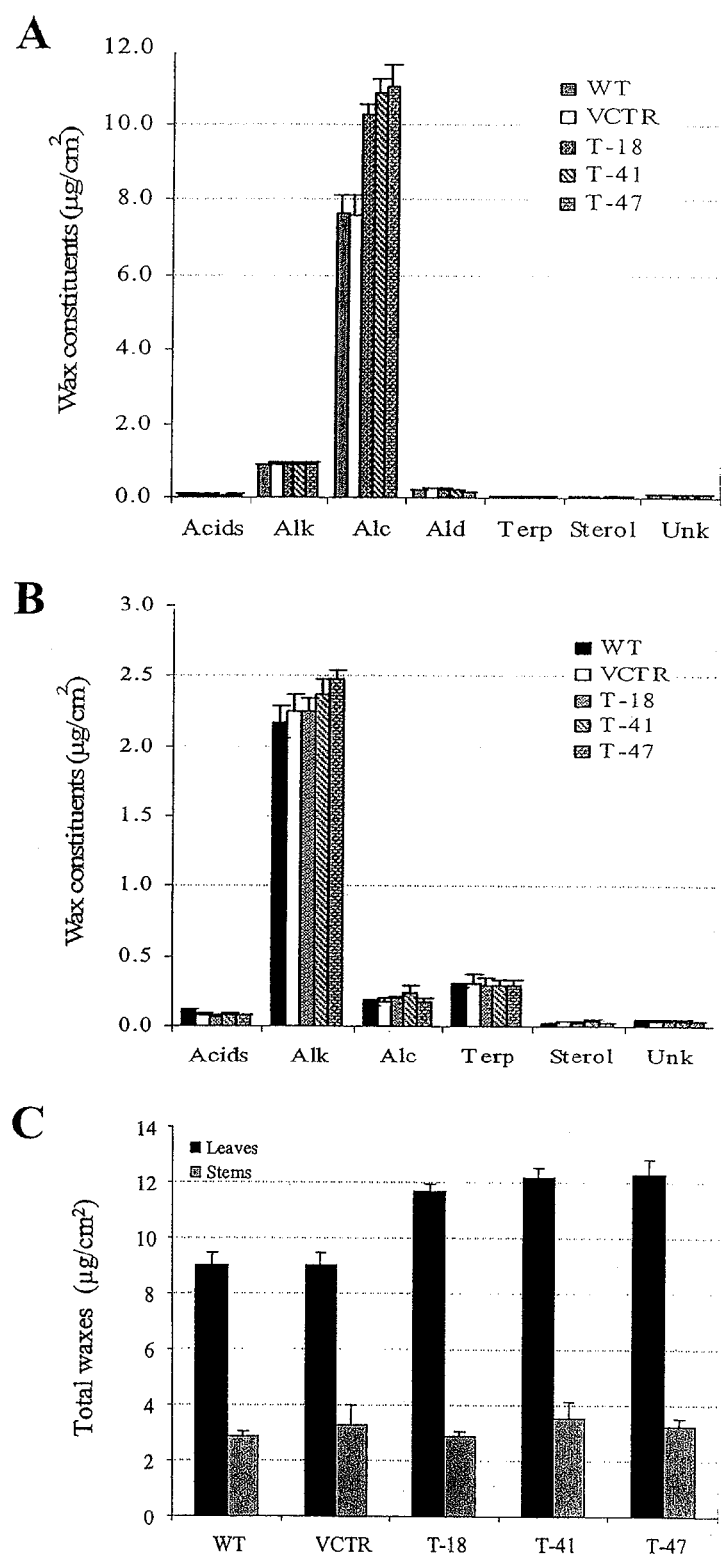
FIG. 7. Cuticular wax accumulation in transgenic and control alfalfa plants. (A) Wax constituents in leaves. (B) Wax constituents in stems. (C) Total wax accumulated on leaves and stems. Acids, long-chain fatty acids; Alk, Alkanes; Alc, primary alcohols; Ald, aldehydes; Terp, terpenoids; Unk, Unknown compounds; WT, wild type; VCTR, empty vector control; T, transgenic lines overexpressing WXP1.

To further determine whether the crystal pattern alteration in transgenic alfalfa was the result of qualitative or quantitative changes in wax loading, leaf samples from the top four fully expanded trifoliates and stem samples from the top four internodes of wild-type, empty vector control and WXP1 transgenic plants were subjected to gas chromatography (GC)-mass spectrometry (MS) analysis. As shown in FIGS. 7A and 7B, primary alcohol is the major constituent of alfalfa leaf wax while alkane is the most abundant wax compound in stem. Total primary alcohol content per leaf area dramatically increased in the WXP1 overexpressed lines (FIG. 7A), while only a slight increase in alkane content was observed in stems of the transgenics (FIG. 7B). No new compound was identified in the transgenic lines.

Figure 8:
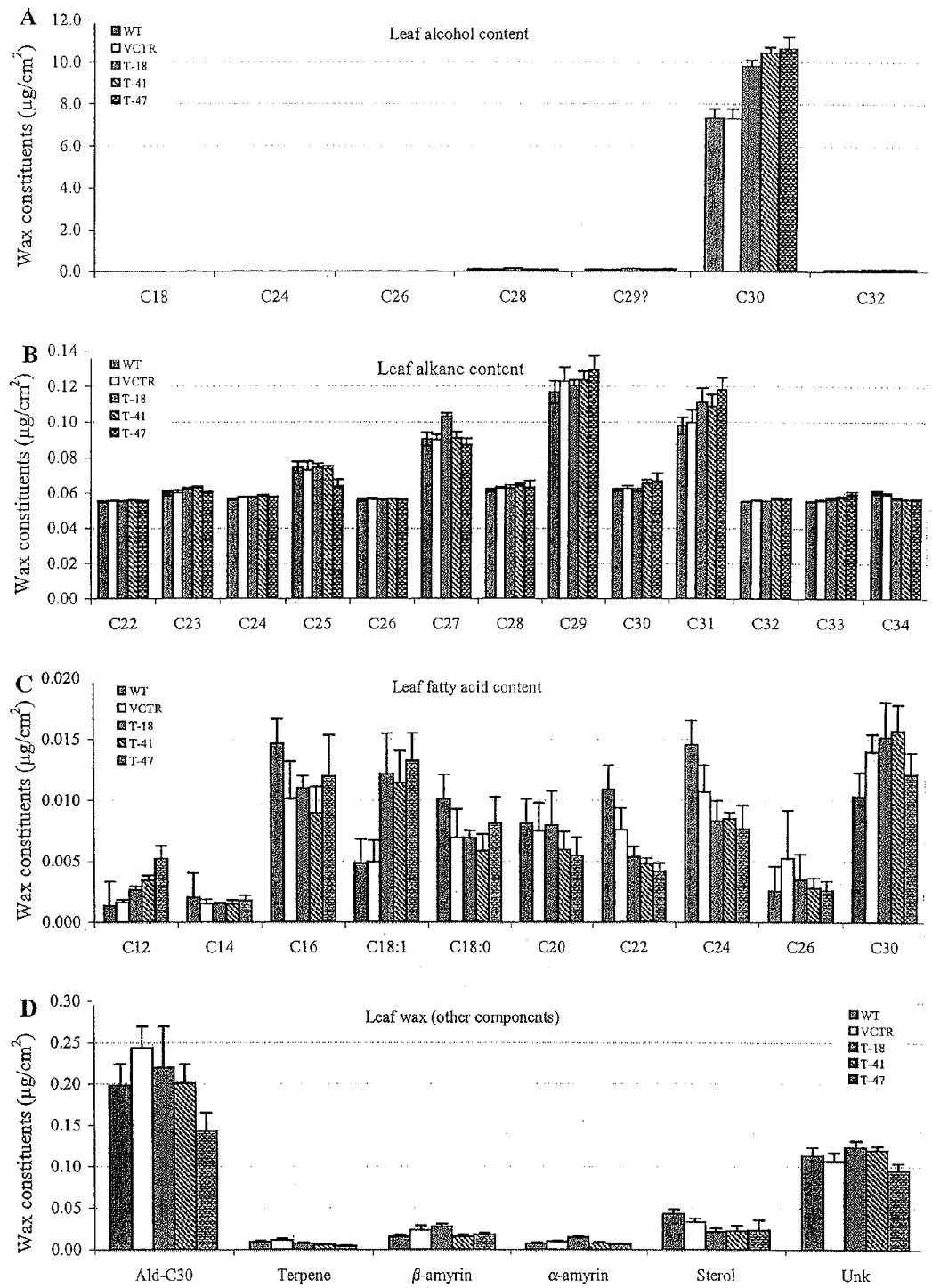
FIG. 8. Leaf cuticular wax profile of transgenic alfalfa plants overexpressing WXP1.

Total wax accumulation per leaf area was significantly higher in the transgenic lines than that in the control plants (FIG. 7C). The biggest change of cuticular wax deposition was in transgenic line 47, which had an increase of 37.7% in its wax load. Lines 18 and 41 showed increases in their total wax load by 29.6% and 35.3%, respectively. The increase was mainly contributed by C30 primary alcohol, which is the major component of alfalfa leaf wax (FIG. 8A). C30 alcohol in transgenic lines 18, 41 and 47 was 34.5%, 43.0% and 45.3% more than that of the control plants, respectively. Other carbon length alcohols did not show significant changes (FIG. 8A). Alkanes were not significantly affected by the overexpression of WXP1, even though C31 alkane had minor increase in the transgenic lines (FIG. 8B). The total amount of long chain fatty acids did not show significant change. The abundance of unsaturated octadecenoic acid (C18:1) was apparently increased in the transgenic lines, while saturated fatty acid (C18:0) remained essentially the same, and the amount of C22 and C24 fatty acids slightly decreased (FIG. 8C). In leaf cuticular wax extracts, C30 aldehyde was the only aldehyde component detected. The amount of this compound decreased in line 47, but no significant change was found in other transgenic lines (FIG. 8D).

Figure 13:
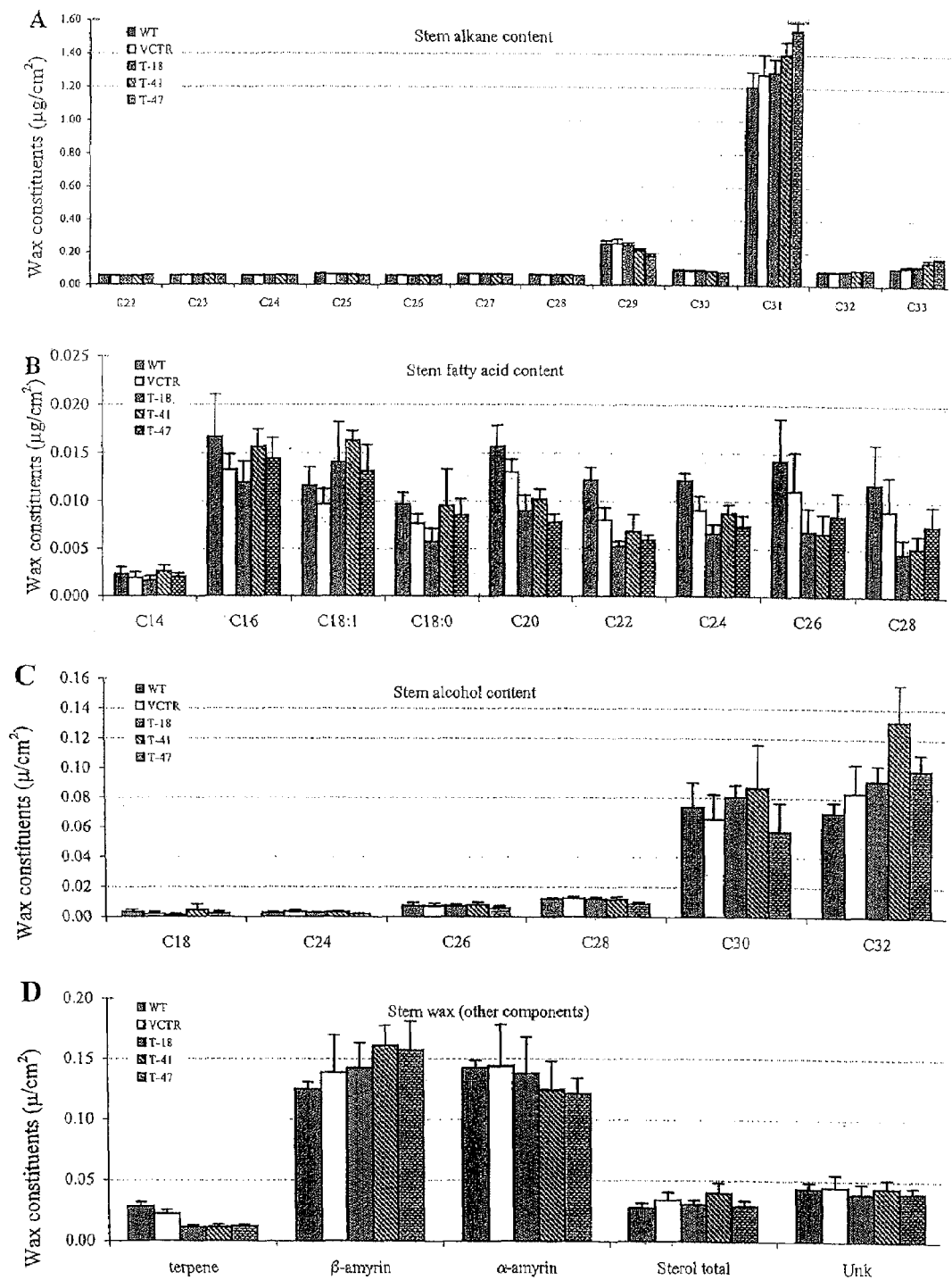
FIG. 13. Stem cuticular wax profile of transgenic alfalfa plants overexpressing WXP1.

In contrast to leaves, cuticular wax accumulation in stems was not significantly altered in the transgenic alfalfa plants (FIG. 7C). The most abundant stem wax component, C31 alkane, increased gradually with the increased transgene expression level from transgenic line 18 to line 47. However, C29 alkane, the second important stem wax component, was negatively affected by the level of transgene expression (FIG. 13A). For the minor components of alfalfa stem wax, only C20 fatty acid and triterpenoids were reduced in the transgenics. No consistent and significant changes were observed for the other components (FIG. 13B-D).

Example 4

Water Loss Rate, Chlorophyll Extraction Rate and Drought Tolerance of Transgenic Alfalfa Overexpressing WXP1

Figure 14:
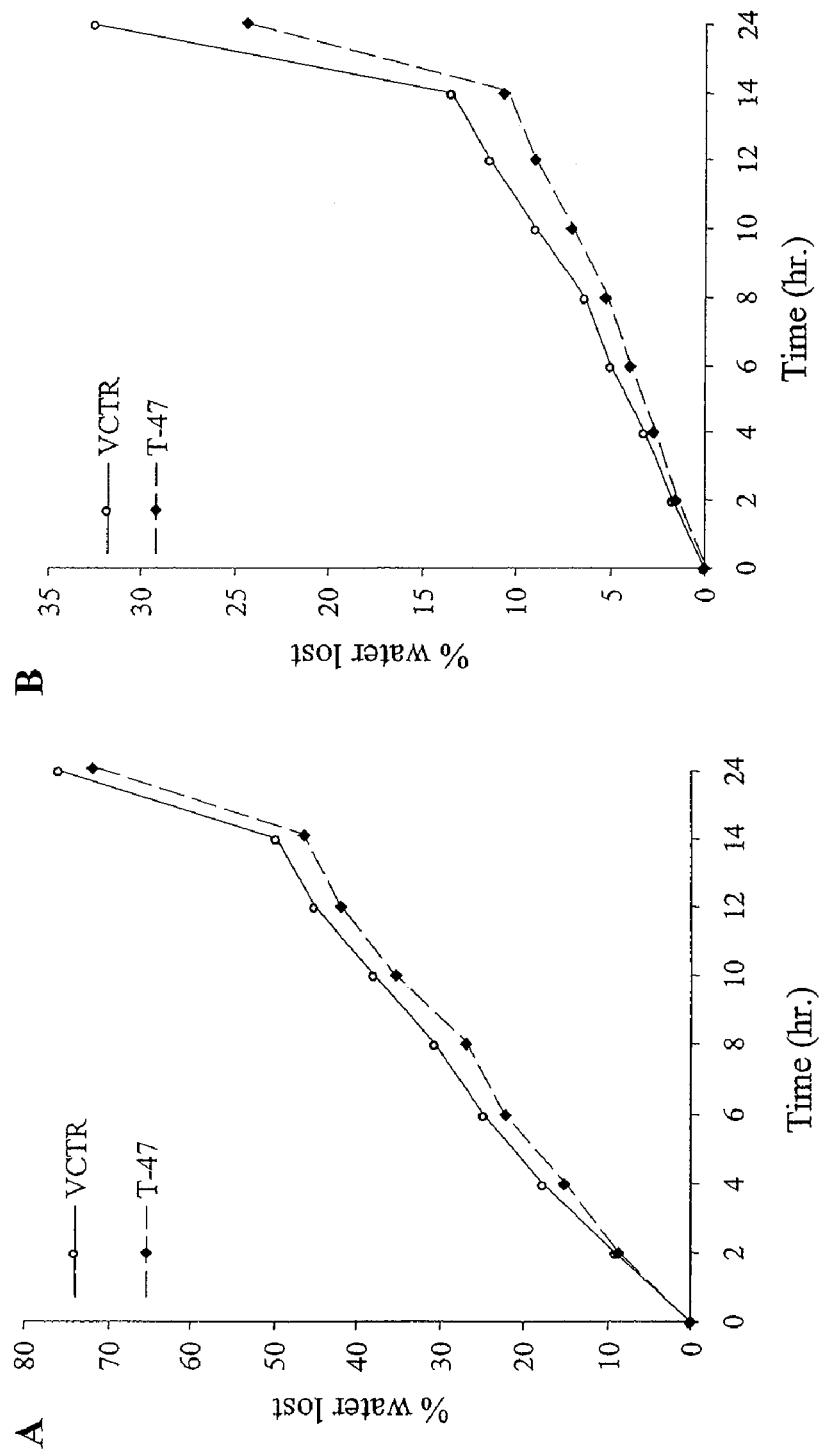
FIG. 14. Water loss rate (±SD) of detached leaves from transgenic and control alfalfa plants. (A) Top-2nd trifoliates. (B) Top-3rd trifoliates. VCTR, empty vector control. T-47, transgenic line overexpressing WXP1.

Detached alfalfa trifoliates were subjected to leaf water loss rate assay. Both top-$2^{nd}$ and top-$3^{rd}$ trifoliates from the transgenic lines showed lower water evaporation rate than that from the vector control (FIG. 14).

Figure 9:
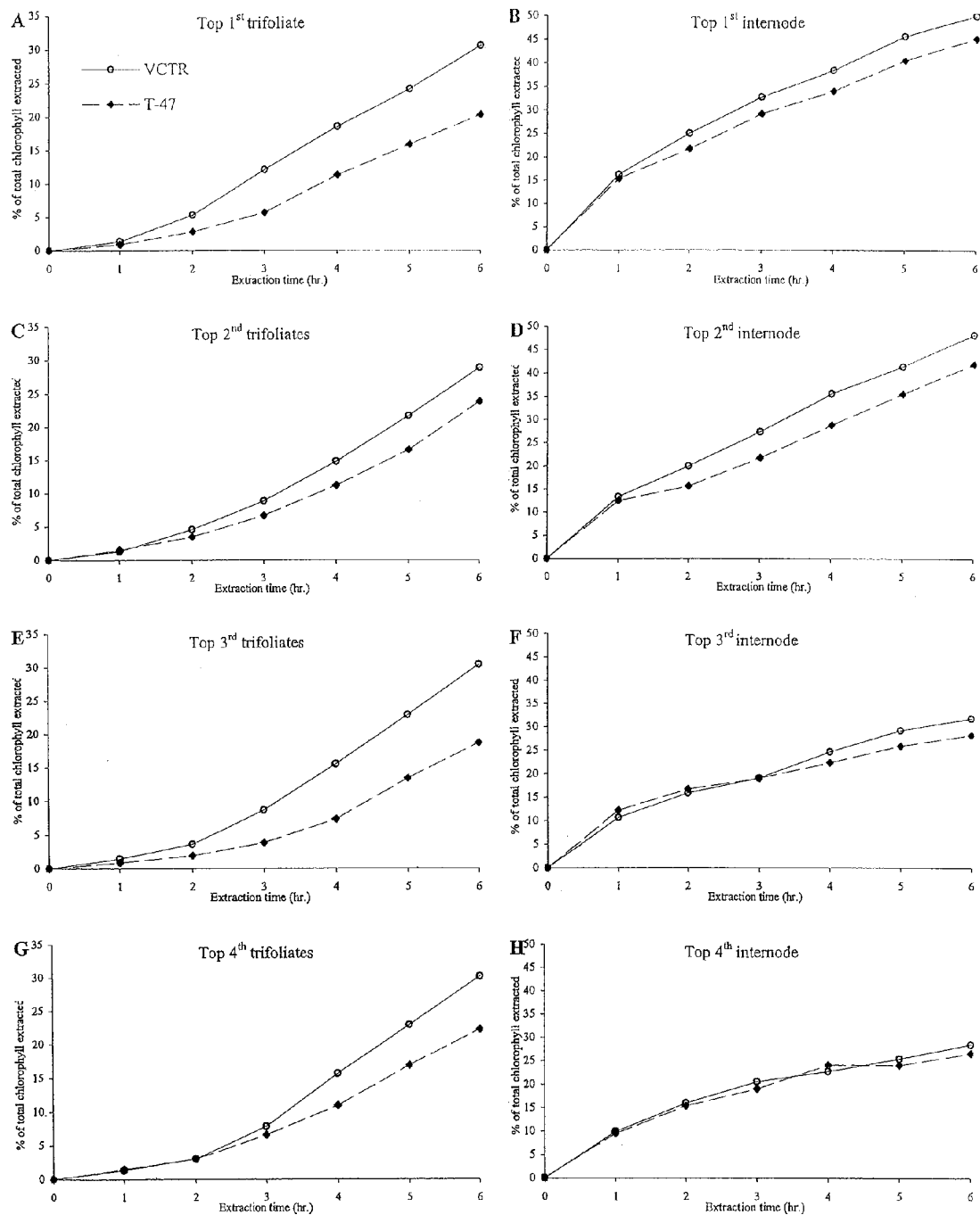
FIG. 9. Chlorophyll leaching from leaves and stems of transgenic and control alfalfa plants. VCTR, empty vector control; T-47, transgenic line overexpressing WXP1.

Chlorophyll efflux analysis revealed that rates of chlorophyll extraction from the top-$1^{st}$ through top-$4^{th}$ leaves during a 6 h period were much slower in the transgenic plants than in the control plants (FIGS. 9A, 9C, 9E and 9G), indicating reduced epidermal permeability in transgenic leaves. In stems, the difference on chlorophyll extraction rate between transgenic and control plants was relatively small, with no difference in the $4^{th}$ internode (FIGS. 9B, 9D, 9F and 9H). In addition, little difference in epidermal permeability was observed between leaves at different positions in the stem, although they represented different developmental stages. However, different internodes showed substantial differences, with older internodes having much less chlorophyll efflux than younger internodes (FIG. 9).

Figure 10:
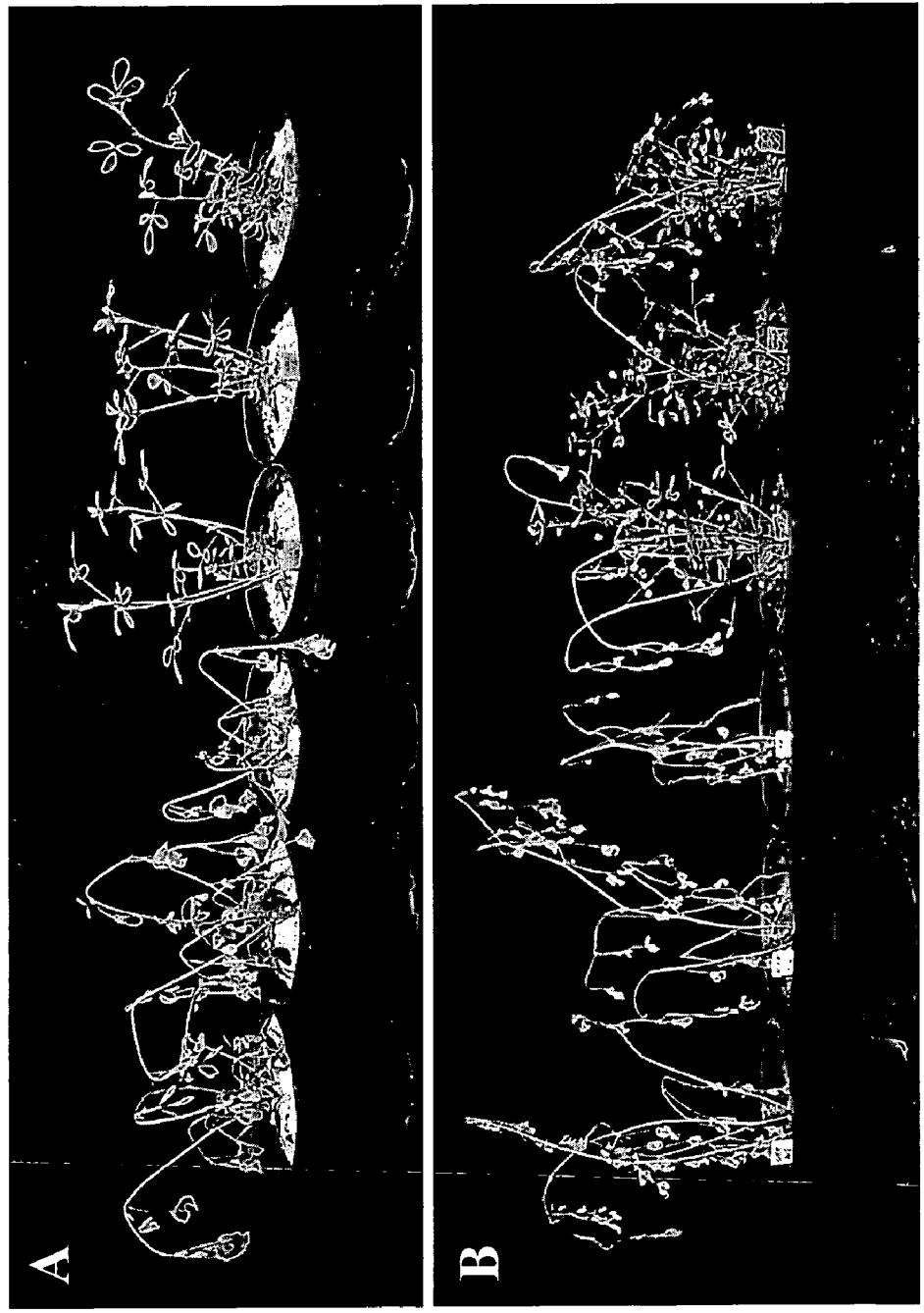
FIG. 10. Effects of drought stress on transgenic and control alfalfa plants. (A) Three days of no-watering in growth chamber. Control plants (left three plants) wilted while transgenics (right three plants) still look normal. (B) After 10 days of no-watering, normal watering scheme was resumed, and the dried plants started recovering. Transgenic plants (right three) recovered much better and quicker than the control plants (left thee).

Transgenic lines and control plants were subjected to drought stress in growth chambers and greenhouse. In the growth chamber experiments, watering was ceased for three replicates of 20-day-old alfalfa plants and the chambers were dehumidified. Three days after watering was stopped, all the control plants became wilted while all the transgenic plants still kept their whole plant turgor (FIG. 10A). The transgenics began to wilt one day later than the control plants. After one more week in the same chambers without watering, all the plants became dehydrated and dead-like. Upon resumption of the normal watering scheme, the transgenic plants recovered much faster and better than the control plants (FIG. 10B). In the greenhouse experiments, it took longer time to completely dehydrate the plants because of the fluctuations in relative humidity. Nevertheless, after three cycles of drought stress-rewatering in a period of four weeks, most of the transgenic plants survived while the control plants failed to recover.

Example 5

Figure 15:
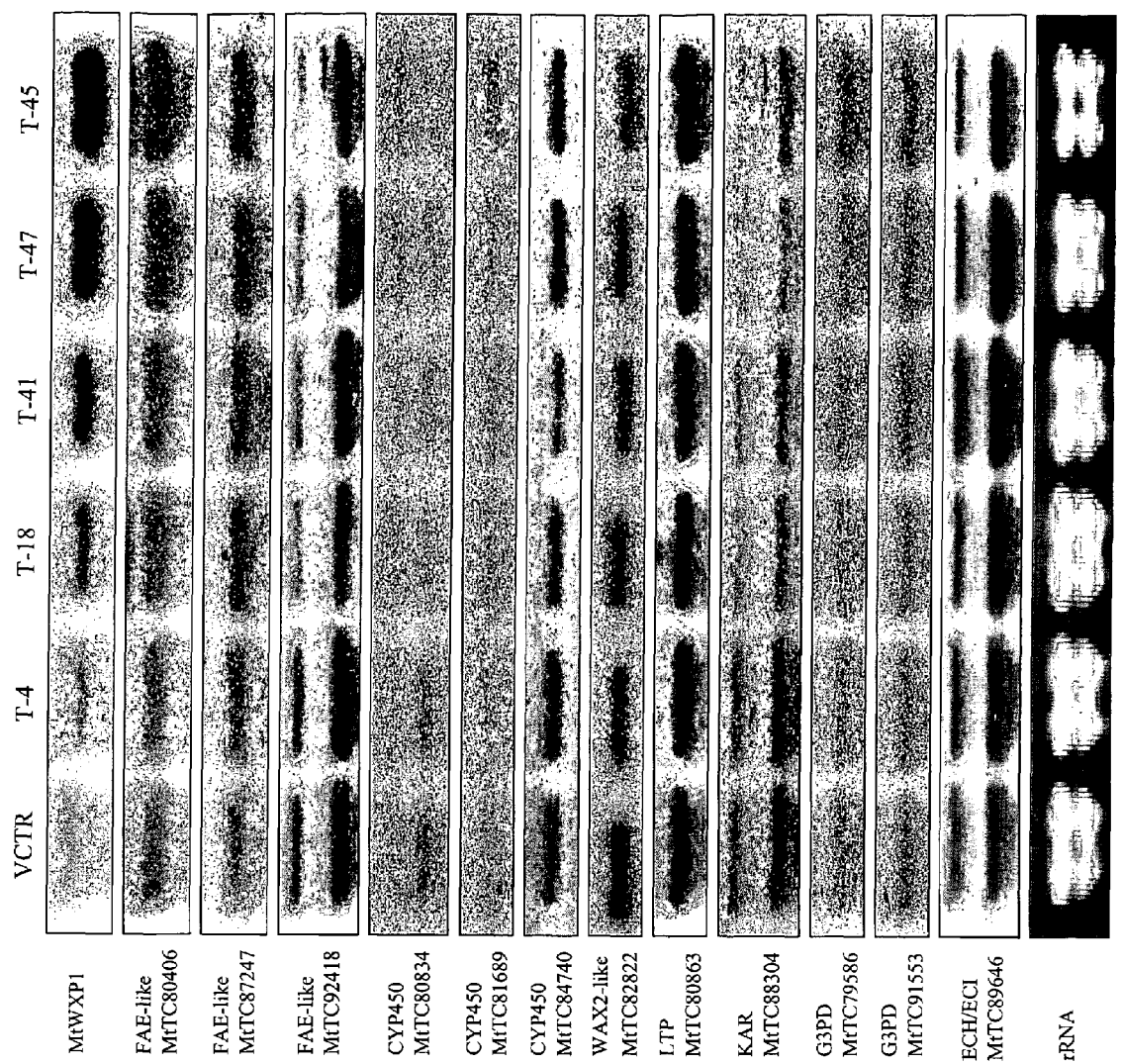
FIG. 15. Northern hybridization analysis of the expression of wax related genes in WXP1 transgenic alfalfa plants. FAE, fatty acid elongase; CYP450, cytochrome P450 monooxygenase; LTP, lipid transfer protein; G3PD, glycerol-3-phosphate dehydrogenase; KAR, β-keto acyl reductase; ECH/ECI, Enoyl-CoA hydratase/isomerase. VCTR, empty vector control; T, transgenic lines overexpressing WXP1.

Overexpression of WXP1 Induced/Suppressed a Number of Genes Related to Wax Biosynthesis Northern hybridization analysis was used to characterize the expression of a number of wax related genes in the transgenic plants. Total RNA was isolated from leaves of transgenic lines 4, 18, 41, 47, and 45; these lines had increasing levels of WXP1 expression (FIG. 15). A list of candidate genes (Table 1) were selected based on TBLASTN search against TIGR *Medicago truncatula* Gene Index database (Quackenbush et al., 2000) with a set of query genes that were implicated in cuticular wax loading or cutin biosynthesis in *Arabidopsis* and maize. All the DNA probes used for hybridization were selected from *M. truncatula* cDNA libraries.

Because of the potential role of fatty acid elongase (FAE) in wax production, and the fact that a putative fatty acid elongase gene was strongly down-regulated by WIN1 overexpression in *Arabidopsis* (Broun et al., 2004), five *M. truncatula* cDNA clones predicted to encode different FAE-like proteins were tested. Totally seven bands were revealed by northern hybridization with these five FAE-like genes. Transcript levels in three of the FAE-like genes, MtTC79579, MtTC80406 and MtTC87247, were enhanced in the transgenic lines with increasing levels of WXP1 expression (Table1, FIG. 15). This is opposite to the effect of WIN1 overexpression. No obvious changes were detected for the other FAE-like genes in the transgenic lines (Table 1).

KCS and CER6 have been implicated in the synthesis of very-long-chain fatty acids (VLCFA) precursors for wax production (Kunst and Samuels, 2003). No change in the expression level of KCS- or CER6-like genes (TC78487, TC82553 and TC81348) was observed in the alfalfa transgenic plants (Table 1).

The LACERATA (LCR) gene encodes cytochrome P450 monooxygenase, which catalyzes ω-hydroxylation of fatty acids ranging from C12 to C18:1 (Wellesen et al., 2001). Overexpression of WXP1 in alfalfa up-regulated two LCR-like genes, TC81689 and TC84740. Two bands showed up when another LCR-like gene (TC80834) was used as probe, the intensity of the upper band was increased, while the intensity of the lower band was decreased with the expression of WXP1 (Table 1, FIG. 15).

*Arabidopsis* WAX2 is predicted to have a metabolic function associated with both cuticle membrane and wax synthesis. Transcript level of one WAX2-like gene (TC82822) was negatively affected by the overexpression of the WXP1, while the mRNA level of the other WAX2-like gene (TC87337) did not change (Table 1, FIG. 15). Maize GL8 functions as a β-ketoacyl-reductase (KAR) in wax production (Kunst and Samuels, 2003). The intensity of the KAR bands showed a negative correlation with expression of WXP1 (Table 1, FIG. 15).

The expression pattern of a number of other genes that were up-regulated by WIN1 in *Arabidopsis* was also analyzed. Among these genes, the expression of the two glycerol-3-phosphate dehydrogenase genes was positively correlated with WXP1 expression, while the phospholipid/glycerol acyltransferase gene was negatively correlated with WXP1 expression. The transcript levels of enoyl-CoA hydratase/isomerase and long-chain acyl-CoA synthase (LACS) were not affected by the overexpression of WXP1 in alfalfa (Table 1, FIG. 15).

TABLE 1

Expression of wax related genes in transgenic alfalfa plants overexpressing WXP1

| MtGI # | Putative protein function/annotation | *Arabidopsis*/maize ortholog | Transcript level |
|---|---|---|---|
| TC79579 | Fatty acid elongase (FAE) | CER2 | Up |
| TC80406 | Fatty acid elongase (FAE) | CER2 | Up |
| TC87247 | Fatty acid elongase (FAE) | CER2 | Up |
| TC88787 | Fatty acid elongase (FAE) | CER2 | None/None |
| TC92418 | Fatty acid elongase (FAE) | CER2 | None/None |
| TC78487 | β-ketoacyl-CoA synthase | KCS1 | None |
| TC82553 | β-ketoacyl-CoA synthase very-long-chain fatty acid | KCS1 | None |
| TC81348 | condensing enzyme | CER6/CUT1 | None |
| TC77258 | Cytochrome P450 monooxygenase | LCR | None |

TABLE 1-continued

Expression of wax related genes in transgenic alfalfa plants overexpressing WXP1

| MtGI # | Putative protein function/annotation | Arabidopsis/maize ortholog | Transcript level |
|---|---|---|---|
| TC80834 | Cytochrome P450 monooxygenase | LCR | Up/Down |
| TC81689 | Cytochrome P450 monooxygenase | LCR | Up |
| TC84740 | Cytochrome P450 monooxygenase | LCR | Up |
| TC82822 | Sterol desaturase | WAX2/CER1 | Down |
| TC87337 | Sterol desaturase | WAX2/CER1 | None |
| TC80863 | Lipid transfer protein | GL1 | None |
| TC88304 | β-keto acyl reductase | GL8 | Down/Down |
| TC79586 | Glycerol-3-phosphate dehydrogenase | At2G41540 | Up |
| TC91553 | Glycerol-3-phosphate dehydrogenase | At2G41540 | Up |
| BI271665 | Phospholipid/glycerol acyltransferase | At 2G38110 | Down |
| TC89646 | Enoyl-CoA hydratase/isomerase | At4G14440 | None/None |
| TC86198 | Long-chain acyl-CoA synthase (LACS) | At3g16170 | None |

Example 6

WXP1 is a Novel Transcription Factor Gene that Activates Wax Production in Leaves of Transgenic Alfalfa Plants The WXP1 gene cloned from *M. truncatula* encodes one of the longest peptides of all the predicted AP2 domain-containing transcription factors in *M. truncatula*. Sequence analysis revealed WXP1 is very different from other well-characterized transcription factors related to abiotic stress or wax accumulation, e.g. DREB/CBF from *Arabidopsis* (Jaglo-Ottosen et al., 1998; Liu et al., 1998), WIN1 from *Arabidopsis* (Broun et al., 2004) and GL15 from maize (Moose and Sisco, 1996). Northern hybridization analysis showed that the expression of WXP1 is inducible by cold or drought stress, which is similar to some members of the DREB/CBF family. The response to environmental stress has not been reported for WIN1 and GL15. As discussed below, functional characterization of WXP1 in transgenic alfalfa plants further proved its novelty.

Because of the unique characteristics and modes of action of transcription factors, it has been realized that the overexpression strategy is particularly effective in revealing transcription factor function (Zhang, 2003). Different from DREB/CBF genes, constitutive expression of the WXP1 gene in alfalfa resulted in a significant increase in wax accumulation on the leaf surfaces. Wax crystals were produced earlier on the adaxial side of newly expanded transgenic leaves, and higher density of wax crystals were found on both adaxial and abaxial sides of mature transgenic leaves. It is important to be able to alter wax accumulation in leaf tissues of crops, because leaves are the primary photosynthetic organs, comprise the primary biomass of most agronomic crops, and are often severely affected by environmental stresses (Jenks et al., 2002). Most of the *Arabidopsis* mutants have alterations in their stem waxes (Jenks et al., 1995; Koornneef et al., 1989). Visual screening of mutagenesis populations of *Arabidopsis* to find mutants having increased leaf glaucousness due to changes in cuticular waxes have had limited success (Jenks et al., 2002). Thus, overexpression of transcription factor genes is indicated to be an effective approach to turn on the wax biosynthetic pathway and lead to increased wax production in leaves.

Example 7

WXP1 Overexpression Affected the Expression of Genes that are Potentially Related to Wax or Cutin Biosynthesis Among the candidate enzymatic genes analyzed, several of them seemed to correlate their expression with the expression of WXP1. In contrast to *Arabidopsis* WIN1, which down-regulated the expression of a fatty acid elongase gene, WXP1 up-regulated three fatty acid elongase genes. It is known that acyl chain extensions are carried out by several distinct elongases with unique substrate chain specificities (Kunst and Samuels, 2003). Thus WXP1 may positively impact the fatty acid elongation process for the production of VLCFA chains that are used for the production of aliphatic wax components. The transcript levels of genes coding for cytochrome P450 monooxygenase and glycerol-3-phosphate dehydrogenase were also up-regulated in the WXP1 transgenics. Glycerol-3-phosphate dehydrogenase is essential for phospholipid synthesis through both the prokaryotic and the eukaryotic glycerolipid pathway (Wei et al., 2001). Cytochrome P450 monooxygenase functions as a fatty acid ω-hydroxylase that is required in the formation of cutin monomers (Wellesen et al., 2001). The results indicate that besides its function in wax biosynthesis, WXP1 may also play a role in the biosynthesis of cutin, which may acts as a barrier that mechanically isolates epidermis cells of adjoining organs.

Fatty acids produced in the plastid from de novo synthesis are directed to at least three biosynthetic pathways that lead to the production of waxes, cutin/suberin, and glycerolipids respectively (Post-Beittenmiller, 1996). This is accomplished by a partition occurred after their biosynthesis, which delivers C16:0 and unsaturated C18:1 fatty acids as precursors to produce glycerolipids or cutin/suberin and saturated C18:0 fatty acid as precursor to produce waxes (Post-Beittenmiller, 1996). In our transgenic WXP1 plants, no significant change was observed for the amount of saturated C18:0 fatty acid and total fatty acids, indicating the increase of wax accumulation, particularly the increase of primary alcohols in leaves, is most probably due to the regulation of genes that control fatty acid elongation and the acyl-reduction pathway. On the other hand, the amount of unsaturated C18:1 fatty acid in leaves was more than double that of controls. The increase of C18:1 fatty acid is consistent with the up-regulation of cytochrome P450 monooxygenase, because the enzyme is directly involved in the biosynthesis of cutin (Wellesen et al., 2001). Further research with respect to WXP1 expression and cuticle composition is required to elucidate the potential role of WXP1 on cutin biosynthesis.

Example 8

Overexpression of WXP1 Confers Drought Tolerance in Transgenic Plants

Overexpression of transcription factor genes DREB/CBF in *Arabidopsis* activated C-repeat/DRE containing down-stream genes that are involved in cold acclimation and drought adaptation. Although the transgenic *Arabidopsis* showed increased stress tolerance, no additional waxes were produced (Jaglo-Ottosen et al., 1998; Kasuga et al., 1999). Thus, the mechanism of DREB/CBF genes on drought tolerance improvement is different from that of WXP1. Overexpression of WXP1 activated wax production and led to the glaucousness appearance in leaves of transgenic alfalfa. Glaucousness resulting from wax accumulation has been considered a beneficial trait for the adaptation of plants to water-limited environments (Jefferson, 1994). Under severe water deficient conditions, plant stomata normally close. The survival of a plant will then depend largely on its ability to restrict water loss through leaf epidermis (Rawson and Clarke, 1988). The transgenic alfalfa plants showed reduced water loss and decreased epidermal permeability, therefore the transgenic plants were much more drought tolerant than the control plants. Genetic and mutant studies have suggested that wax accumulation is a potential drought adaptation trait (Jefferson, 1994). The studies here using isogenic lines (wild type control, empty vector control and transgenic plants) clearly demonstrate the positive effects of cuticular waxes on drought tolerance. Despite the fact that both drought tolerance and wax accumulation are complicated traits that are under the control of multiple genes. The results demonstrated for the first time that overexpression of a single transcription factor gene, WXP1, could increase wax production and improve plant drought tolerance.

Alfalfa is the fourth most widely grown crop in the United States behind only corn, wheat and soybeans. It contributes enormously to world's dairy, beef and wool production, although the contribution often goes unrecognized. As a perennial forage crop, alfalfa is a fairly hardy species and has a relative high level of drought tolerance compared to many food crops. Even so, increased wax loading by overexpression of WXP1 on alfalfa leaves further enhances its drought and dehydration tolerance. Thus, manipulation of wax production by transgenic expression of WXP1 or its orthologs has significant potential for the genetic improvement of other forage, food or horticultural crops. Although transgenic alfalfa plants showed moderate slow growth due to increased wax accumulation, the problem may be overcome by the use of epidermis-specific promoter (Hooker et al., 2002) or drought inducible promoter (Kasuga et al., 1999; Kasuga et al., 2004). The use of stress-inducible promoter has been shown to minimize the negative effects of DREB/CBF overexpression on plant growth (Kasuga et al., 1999; Kasuga et al., 2004).

Example 9

Growth and Development of *Arabidopsis* Plants Overexpressing WXP1 and WXP2

Figure 16:
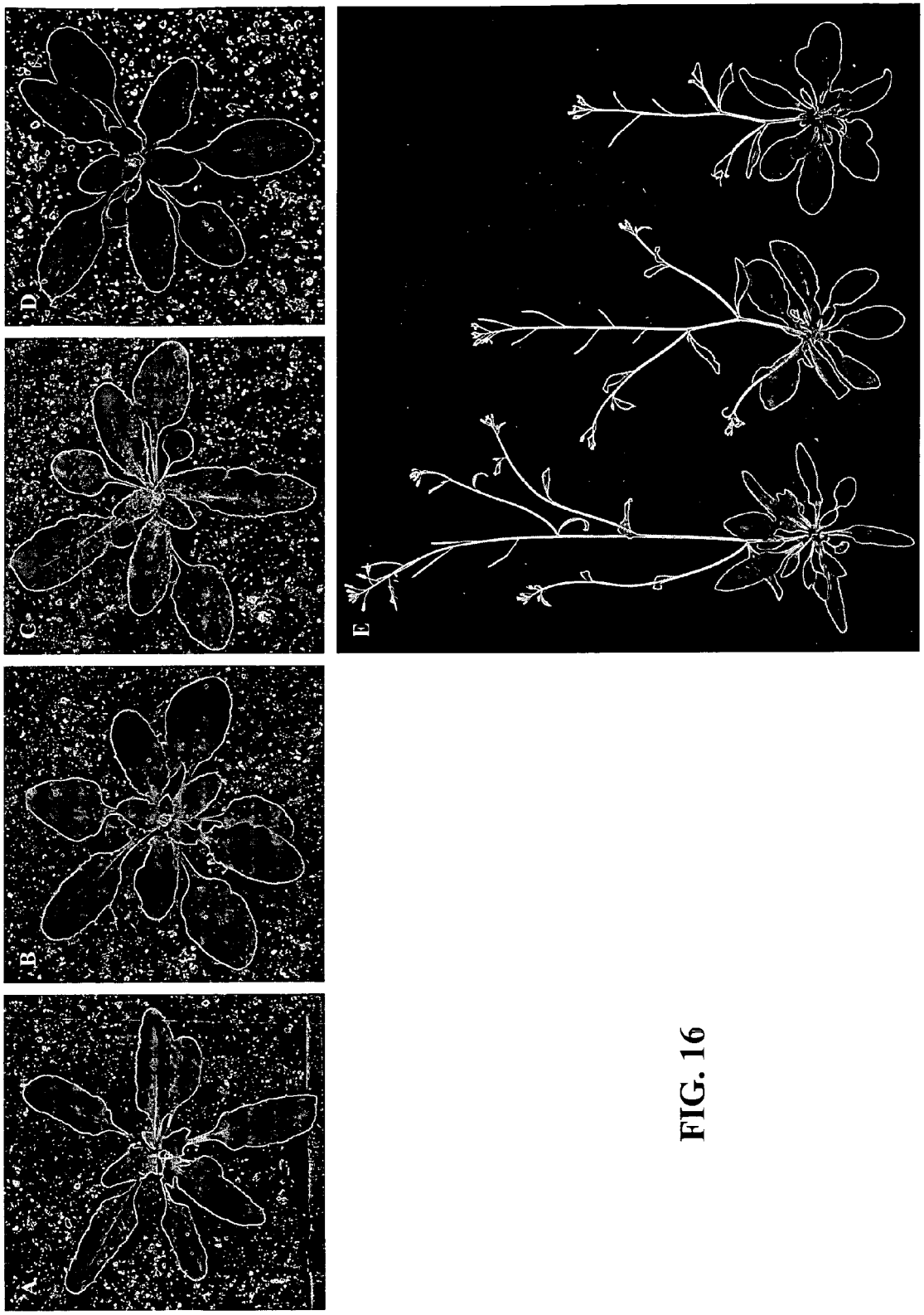
FIG. 16. Morphological changes induced by transgenic expression of WXP1 and WXP2 in *Arabidopsis*. A, 4-week-old vector control plants; B, C, D, 4-week-old plants from line 4, 55, and 57 overexpressing WXP1; E, 6-week-old plants of vector control (left) and transgenic plants from line 4 (middle) and line 14 (right) overexpressing WXP2.

Expression of WXP1 and WXP2 did not lead to severe growth retardation of transgenic *Arabidopsis* as AtWIN1/AtSHINE1 (Aharoni et al., 2004; Broun et al., 2004), AtCBF1/DREB1b (Jaglo-Ottosen et al., 1998), AtCBF3/DREB1a (Kasuga et al., 1999; Gilmour et al., 2000) and AtCBF4 (Haake et al., 2002) did. The transgenic plants with WXP1 gene overexpression did not show a significant change in plant growth rate and flowering date. Nevertheless, the plants have broader leaves with more glaucous leaf surfaces compared with the control plant (FIG. 16A-16D). The transgenic plants with WXP2 overexpression showed more morphological changes. The plants were shorter and flowered one week later than the control (FIG. 16E).

Example 10

WXP1 and WXP2 Overexpression in *Arabidopsis* Resulted in Leaf Cuticular Wax Alteration WXP1 and WXP2 conferred cuticular wax alteration in rosette leaves when overexpressed in *Arabidopsis* (Tables 2 and 3). The total wax for the 3-week-old plants increased 32.36% with WXP1 overexpression and 16.96% with WXP2 overexpression. For the 6-week-old plants, total leaf wax increased 27.51% and 23.61% with the overexpression of WXP1 and WXP2, respectively.

The wax increase in both cases was contributed by the increase of alkanes that are the major cuticular wax components of *Arabidopsis*. For the 3-week-old plants, the total alkanes accumulation in leaves changed from 52.95±3.11 micrograms per gram fresh weight (µg/g FW) in the vector control plants to 77.14±2.11 µg/g FW in the WXP1 overexpresors and 72.38±2.78 µg/g FW in the WXP2 overexpressors, increased by 45.68% and 36.71%, respectively (Table 2). For the rosette leaves from the 6-week-old *Arabidopsis* plants, the total alkanes changed from 0.391±0.0319 micrograms per square centimeter leaf surface (including both adaxial and abaxial sides, µg/cM$^2$) in the vector control plants to 0.543±0.0393 µg/cM$^2$ in the WXP1 overexpresors and 0.541±0.0259 µg/cM$^2$ in the WXP2 overexpresors, increase by 36.38% and 38.19%, respectively (Table 3).

TABLE 2

Cuticular Wax Composition Change of Rosette Leaves from 3-week-old Transgenic *Arabidopsis* Plants

| Compound Class | VC[a] (µg/g FW) n = 6 | MtWXP1 (µg/g FW) n = 5 × 4[b] | Average percent increase | MtWXP2 (µg/g FW) n = 5 × 4[b] | Average percent increase |
|---|---|---|---|---|---|
| Fatty acids | 11.85 ± 0.41 | 15.54 ± 0.38 | 31.14** | 11.88 ± 0.73 | 0.22 |
| Aldehydes | 8.82 ± 0.78 | 9.45 ± 0.30 | 7.14 | 9.53 ± 0.58 | 8.01 |
| Prim. alcohols | 23.18 ± 1.01 | 24.80 ± 0.82 | 6.99 | 19.73 ± 1.03 | −14.88* |
| Sec. alcohols | 4.96 ± 0.17 | 7.75 ± 0.20 | 56.40** | 5.49 ± 0.37 | 10.81 |
| Alkanes | 52.95 ± 3.11 | 77.14 ± 2.11 | 45.68** | 72.38 ± 2.78 | 36.71** |
| Cholesterol | 2.21 ± 0.09 | 1.68 ± 0.06 | −24.00** | 1.28 ± 0.05 | −42.36** |
| Sterols | 4.65 ± 0.24 | 4.02 ± 0.13 | −13.72 | 3.52 ± 0.14 | −24.33* |
| Sitosterol | 9.60 ± 0.31 | 12.67 ± 0.53 | 31.91** | 13.63 ± 0.79 | 41.90** |
| Unidentified | 3.40 ± 0.14 | 3.25 ± 0.20 | −4.43 | 3.52 ± 0.18 | 3.48 |

TABLE 2-continued

Cuticular Wax Composition Change of Rosette Leaves from 3-week-old Transgenic *Arabidopsis* Plants

| Compound Class | VC[a] (μg/g FW) n = 6 | MtWXP1 (μg/g FW) n = 5 × 4[b] | Average percent increase | MtWXP2 (μg/g FW) n = 5 × 4[b] | Average percent increase |
|---|---|---|---|---|---|
| Total | 121.64 ± 3.47 | 156.30 ± 3.23 | 28.50** | 140.96 ± 5.23 | 15.89* |
| Total Wax | 101.76 ± 3.40 | 134.69 ± 2.67 | 32.36** | 119.02 ± 4.44 | 16.96* |

[a]Empty vector control.
[b]Data from five independent transgenic lines, which had four replicates for each line.

TABLE 3

Cuticular Wax Composition Change of Rosette Leaves from 6-week-old Transgenic *Arabidopsis* Plants

| Compound Class | VC[a] (μg/cM$^2$) n = 6 | MtWXP1 (μg/cM$^2$) n = 5 × 4[b] | Average percent increase | MtWXP2 (μg/cM$^2$) n = 5 × 4[b] | Average percent increase |
|---|---|---|---|---|---|
| Fatty acids | 0.116 ± 0.0047 | 0.120 ± 0.0105 | 3.35 | 0.133 ± 0.0051 | 14.83* |
| Aldehydes | 0.021 ± 0.0032 | 0.017 ± 0.0022 | −18.46** | 0.038 ± 0.0033 | 80.33** |
| Prim. alcohols | 0.092 ± 0.0108 | 0.120 ± 0.0113 | 30.70** | 0.055 ± 0.0033 | −40.24** |
| Alkanes | 0.391 ± 0.0319 | 0.534 ± 0.0393 | 36.38** | 0.541 ± 0.0259 | 38.19** |
| Cholesterol | 0.032 ± 0.0038 | 0.020 ± 0.0017 | −36.61** | 0.023 ± 0.0014 | −28.29** |
| Unidentified | 0.037 ± 0.0034 | 0.033 ± 0.0032 | −12.18* | 0.044 ± 0.0032 | 18.35** |
| Total | 0.689 ± 0.0352 | 0.844 ± 0.0605 | 22.43** | 0.834 ± 0.0338 | 20.95** |
| Total Wax | 0.620 ± 0.0395 | 0.791 ± 0.0576 | 27.51** | 0.767 ± 0.0311 | 23.61** |

[a]Empty vector control.
[b]Data from five independent transgenic lines, which had four replicates for each line.

Example 11

Arabidopsis Plants Overexpressing WXP1 and WXP2 were More Drought Tolerant

Figure 17:
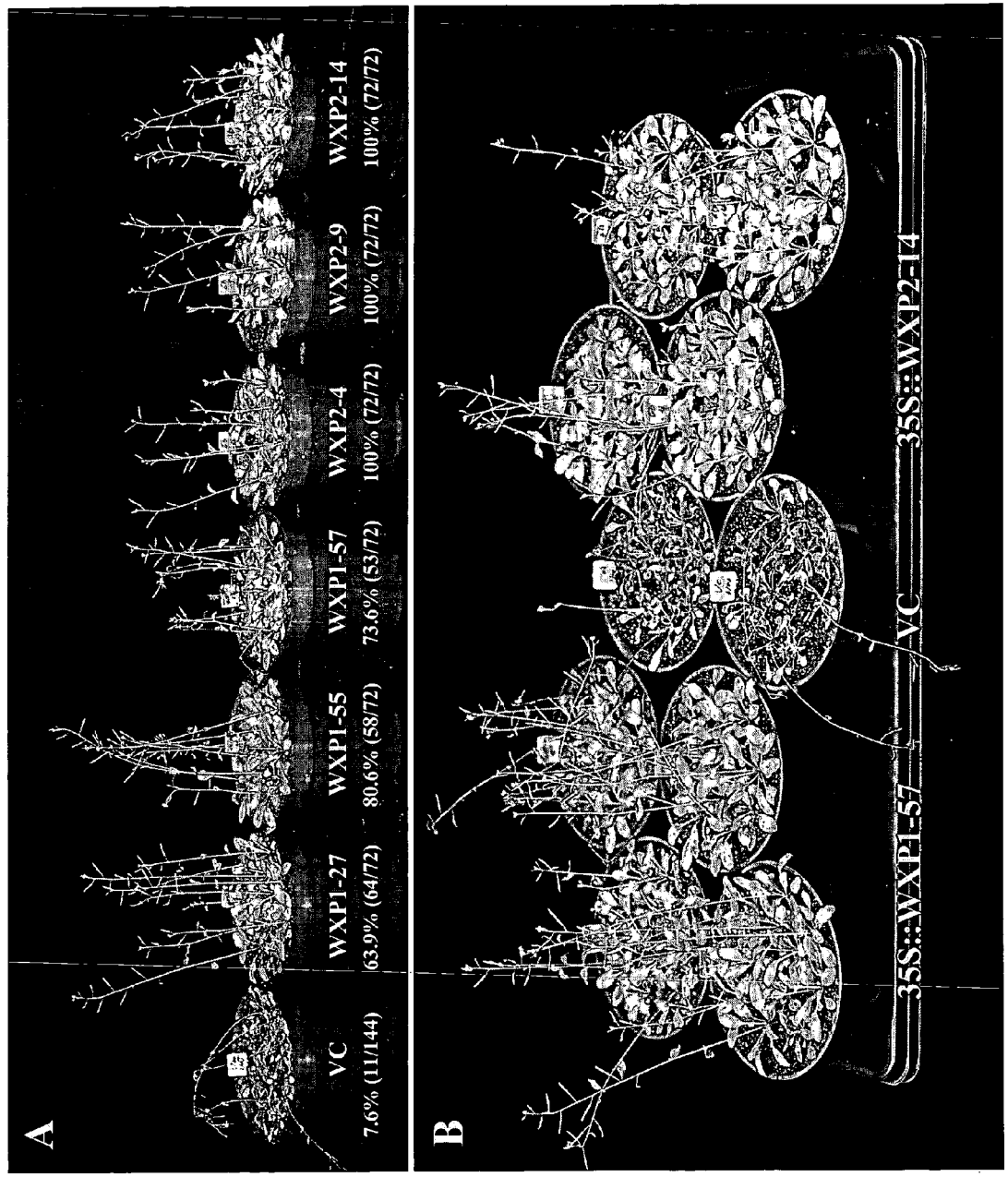
FIG. 17. Whole plant drought tolerance of 35S::WXP1 and 35S::WXP2 transgenic *Arabidopsis* plants. (A) Phenotype and survival rate (%) of different transgenic lines. (B) Transgenic lines that harbored either WXP1 or WXP2 from different replicates.

Overexpression of both WXP1 and WXP2 in *Arabidopsis* lead to increased drought tolerance as demonstrated by whole plant drought tolerance assays and the fresh weigh loss of detached leaves (FWLDL). When compared with the vector controls, the transgenic lines survived a two week drought stress much better (FIG. 17). From two independent studies that had three replicates each, only 7.6% of control plants survived. However, the survival rate for the WXP1 transgenic lines were from 63.9% to 80.6%, and the survival rate for the WXP2 transgenic lines were 100%.

Figure 18:
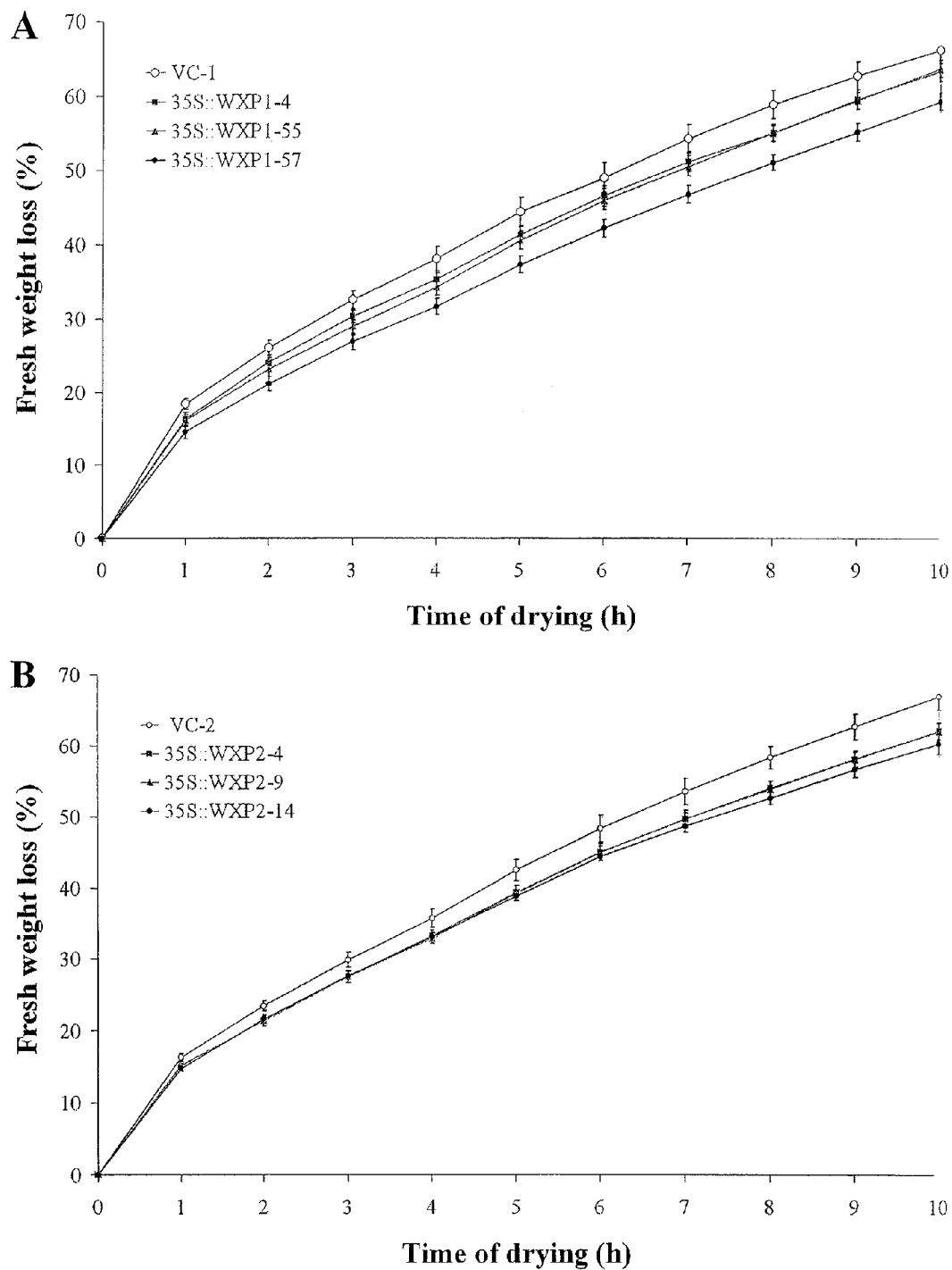
FIG. 18. Assay for fresh weight loss of detached leaves (FWLDL) for transgenic *Arabidopsis* plants overexpressing WXP1 (A) and WXP2 (B).

The assay for fresh weight loss of detached leaves may partially explain the results from the whole plant drought tolerance assay. The fresh weight loss from both WXP1 and WXP2 transgenic lines were significantly lower than that of controls at most of the timepoints (FIGS. 18A and 18B).

Example 12

Materials and Methods

A. Construction of pC35S-WXP1 Vector and Alfalfa Transformation

The coding sequence of WXP1 from *Medicago truncatula* (genotype Jemalong A17) was PCR amplified using primers 5'-GGTACCATGGATTTCTTCAACA-3' (forward) (SEQ ID NO:3) and 5'-AACCGGTCACCAAATTCATCCA-3' (reverse) (SEQ ID NO:4) and digested by Nco I and BstE II. The fragment was inserted into pCAMBIA 3301 vector by replacing the gusA gene. The resulting binary vector pC35S-WXP1 was transferred into *Agrobacterium tumefaciens* stain C58C1 using freezing/heat shock method.

An alfalfa genotype, Regen SY-4D, was used for *Agrobacterium*-mediated transformation to generate transgenic plants (Austin et al., 1995). Vegetatively propagated plants from the original Regen SY-4D clone were used as wild type control. Alfalfa lines transformed with the original pCAM-BIA3301 vector were used as vector control.

B. Growth and Treatments of *Medicago Truncatula*

*Medicago truncatula* (genotype Jemalong A17) seeds were pre-germinated and planted in 4.5-inch pots filled with Turface MVP clay (Profile Products LLC, Buffalo Grove, Ill.). Plants were grown in greenhouse at 24/22° C. with 16 h/8 h photoperiod and a relative humidity at ~70-80%. Four-week-old plants were used for drought, cold and ABA treatment. For drought stress treatment, watering was ceased for one to four days, which represented very mild, mild, moderate, and severe drought stresses, respectively. Additional severely stressed plants were re-watered and tissue was sampled 24 hours later as recovering treatment. Cold treatment was preformed by transferring plants to a 4° C. cold room, and leaf tissues were collected at different timepoints. Samples from recovered tissues were also collected 24 h after transferring the plants back to greenhouse. For ABA treatment, 100 μM ABA (mixed isomers) in 0.02% Tween-20 water solution was sprayed on leaves and also poured into the pots. Controls were sprayed and watered with the same solution without ABA. Leaf tissues were sampled at different timepoints.

C. Growth and Treatments of Alfalfa

The transgenic or control plants were propagated using shoot cuttings. Root system was developed and seedlings established 2-3 weeks after transferring the shoot cuttings to Oasis® Rootcubes® Growing Medium (Smithers-Oasis U.S.A., Kent, Ohio). Seedlings were transplanted to 4.5-inch pots filled with BM-7 bark mix (Berger, Saint-Modeste, Quebec, Canada). For the analysis of wax content, chlorophyll leaching and leaf water loss rate, samples were taken from plants with 6-7 fully expanded trifoliates on the major stem and 4-6 trifoliates on the branches. All the plants were grown in a greenhouse at 23/19° C. with 14h/10h photoperiod and relative humidity at ~50%. Flowering time was measured as the days from transplanting to the emergence of first flower. Plant height and fresh weight was measured when all the plants flowered after 80 days of growth. Dry matter data was obtained by drying individual plants for 48 hours at 60° C.

For THE drought tolerance study, seedlings were transplanted to 4.5-inch pots and grown in growth chamber at 23/19° C. with 16 h/8 h photoperiod and relative humidity at 60%. After twenty days of growth, plants (in three replicates) were drought stressed by stopping watering. In the mean time, humidity was re-set to 20% and photoperiod was re-set to 8 h/16 h in order to keep the stomata closed most of the time. Drought tolerance phenotype was recorded 3-4 days later. When the control plants became totally dried or dead-like (~10 days after watering was withheld), all the pots were re-watered and humidity was re-set to 60%. Plant recovery was scored two weeks later. In the greenhouse experiment, the plants were subjected to three cycles of drought-recovery treatment. During each cycle of drought-recovery treatment, plants were drought stressed for 7 days and watering resumed for 2 days.

D. Growth and Treatments of *Arabidopsis*

*Arabidopsis thaliana* ecotype Colombia was used to generate transgenic plants. All genes, including the GusA (as empty vector control (VC)) and WXP1 and WXP2 were driven by a CaMV 35S promoter.

T2 and T3 seeds were sterilized with 20% bleach (with 0.1% SDS) and rinsed three times in sterile water. The re-suspended seeds in 0.1% agarose solution were uniformly spread on MS medium with appropriate selection. Plates were put under 4° C. for 48-72 h before growing the plants under 22° C. with 16/8 h light/dark. One week old seedlings were transferred to appropriate medium or to soil.

For normal growth and detached leaf sampling, Sunshine Professional Mix 350 soil (Sun Gro Horticulture Distribution Inc., Bellevue, Wash.) was used. For whole plant drought and freezing tolerance assay, a customized soil mixture comprised five parts (in volume) of Sunshine Professional Growth Mix #4, four parts of medium size vermiculite (both from Sun Gro Horticulture Distribution Inc., Bellevue, Wash.) and one part of washed medium sand (No. 1962, The Quikrete Companies, Inc., Atlanta, Ga.) was used. Before and after stress treatment and for leaf sampling, all the plants were grown in growth chamber under long-day conditions (16 h light/8 h dark) with cool-white light (125 $\mu$mol m$^{-2}$ s$^{-1}$), consistent temperature (22° C.) and relative humidity (80%) except for during the period of whole plant drought stress treatment.

E. Whole Plant Drought Tolerance Assay of Transgenic *Arabidopsis*

One week after transplanting, transgenic *Arabidopsis* plants (12 individuals/4.5-inch-pot) were subjected to drought stress by stopping watering. Three days later, the growth chamber was re-set to short-day condition (8 h light/16 h dark) and a relative humidity of 20%. Plants were rehydrated and observed for recovery after 1 week. The study was repeated twice.

F. Assay for Fresh Weight Loss from Detached Leaves of Transgenic *Arabidopsis* Plants For water loss measurements, leaves of 4-week-old plants were detached and weighed immediately in a plastic weighing boat (pre-dried overnight at 65° C. and pre-weighted). The weighing boats with the leaves then were placed on a laboratory bench in a dark room (room temperature was at 22±1° C. and relative humidity at 23±1%) and weighed at designated time intervals. The percentage loss of fresh weight was calculated based on the initial weight of the samples. There were three replicates for each line. The same design repeated twice in similar conditions.

G. RNA Gel Blotting and Hybridization

Total RNA was extracted with MRC Tri-Reagent® (Molecular Research Center, Inc., Cincinnati, Ohio). Twenty micro-grams of RNA were loaded in each lane of 1.2% agarose gels with formaldehyde. WXP1 cDNA and other wax biosynthesis related genes from *M. truncatula* was $^{32}$P labeled using the RanPrime DNA Labeling System (Invitrogen, Carlsbad, Calif.) as instructed by the manufacturer. Northern hybridization was conducted using High Efficiency Hybridization System and Washing/Pre-Hyb solution (Molecular Research Center) following manufacturer's instructions.

H. Bioinformatics

Multiple sequence alignment was performed with Clustal W (Thompson et al., 1994) version 1.82 through EMBL-EBI Sequence Analysis launcher using default parameters (www.ebi.ac.uk/clustalw/). Rooted phylogenetic tree was displayed by TreeView program with PHYLIP method. Sequence similarity was calculated with MegAlign program of DNASTAR (Madison, Wis.). The box-shade in sequence alignment was created using BOXSHADE 3.21 (www.ch.embnet.org/software/BOX-form.html).

I. Scanning Electron Microscopy (SEM)

The top-first and the second trifoliates and the top two internodes from the major stem were harvested and air-dried at room temperature. The middle section between the leaf edge and the major vein of the leaflets or the middle of the internodes were mounted on stubs and coated with ~20 nm of 60/40 Gold-Palladium particles using a Hummer VI sputtering system (Anatech LTD, Springfield, Va.). Coated surfaces were viewed using a JEOL JSM-840 scanning electron microscope at 15 kV (Peabody, Mass.).

J. GC-MS Analysis of Cuticular Wax Composition

Leaf cuticular wax samples were collected from top four fully expanded trifoliates excised from the major stems. The stem cuticular wax samples were collected from the top four internodes. One leaflet was excised from each trifoliate and the four leaflets were combined as one leaf sample. Four internodes were combined as one stem sample. Each sample was inserted into a 20-mL glass tube, and 10-mL (for leaves) or 5-mL (for stem) of hexane (Sigma-Aldrich, Inc., St. Louis, Mo.) was added. Tissues were agitated for 2 min on a rotator at 50 rpm, and the solvent was decanted into new glass tubes. Tissues and tubes were given a 10-s rinse with the same amount of hexane, and the solution was combined in the new tubes. The hexane-soluble wax extracts were evaporated to a small volume (~1 mL) under a nitrogen stream and then transferred into 2-mL auto-sampler vials. After complete evaporation in the 2-mL vials, the extracts were resuspended/derivatized in 15.0 µL of 70% Pyridine and 30% MSTFA (with 0.01 µg/µl of cholesterol as internal standard) for every one cm$^2$ leaf section or one cm$^2$ stem surface area. Derivatization was performed for 60 min at 50° C. One microliter of the solution was injected onto an Agilent 6890 gas chromatograph in splitless mode. The injector was held at 280° C., the oven programmed from 120° C. (2 min) to 315° C. (8 min) at 5° C./min, and the transfer arm held at 250° C. The GC was coupled to an Agilent 5973 MSD using electron impact ionization with scanning masses 50-650. Duplicate injections were performed for each sample, and the average value of the two injections was used for statistical analysis. The peak value was extracted using Agilent Chemstation integration of the total ion chromatogram.

Quantification was based on peak areas and the variation in MS sensitivity was adjusted based on the internal standard as described by Jenks et al (1995) and Bergman et al (1991) with modifications. Dose responsive curve for correction were developed for each class of wax components: heptadecanoic acid for free fatty acids, tridecanal for adehydes, hentriacontane for alkanes, docosanol for primary alcohols, and cholesterol for sterols, triterpenes and other unknown peaks. The amount of each cuticular wax component and total wax composition was expressed per unit of leaf or stem surface area. Leaf areas were determined using computer digitization of the leaf images by scanning (NIH ImageJ 1.31t). Stem surface areas were calculated as the surfaces of right circular cylinders for every internodes (Chen et al., 2003). All values represent averages of six replicate plant samples±SD.

K. Quantification of Epidermal Traits

To quantify leaf water loss rate, the top-$2^{nd}$ and top-$3^{rd}$ trifoliates were detached from 20-d old alfalfa after the plants were kept in constant dark for 10 hours. Dehydration and measurement was performed in a dark room at 23° C. Humidity was around 50% in the room.

Epidermis permeability was measured using chlorophyll extraction assay. Three trifoliates or stem internode segments from the same stem position were collected from 20-d old alfalfa plants, and immersed in 50-mL tubes with 15 mL (for trifoliates) or 10 mL (for internodes) of 80% ethanol. Tubes were agitated gently on a rotator platform at 50 rpm. Aliquots of 1000 µL were taken out for chlorophyll quantification and poured back to the same tube at every timepoint. The amount of chlorophyll extracted into the solution was quantified using a U-60 spectrophotometer (Beckman, Fullerton, Calif.) and calculated from light absorption at wavelength of 647 and 664 nm as described by Lolle et al. (1997). Chlorophyll extracted at each time point was expressed as a percentage of total chlorophyll extracted after 48 hours of immersion.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,508,468; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042

Aarts et al., *Plant Cell*, 7, 2115-2127, 1995.
Abdullah et al., *Biotechnology*, 4:1087, 1986.
Aharoni et al., *Plant Cell*, 16: 2463-2480, 2004.
Austin et al., *Euphytica*, 85, 381-393, 195.
Bateman et al., *Nucl. Acids. Res.*, 30, 276-280, 2002.
Bates, *Mol. Biotechnol.*, 2(2):135-145, 1994.
Battraw and Hall, *Theor. App. Genet.*, 82(2):161-168, 1991.
Bergman et al., *Environ. Entomol.*, 20, 781-785, 1991.
Bevan et al., *Nucleic Acids Research*, 11(2):369-385, 1983.
Bhattacharjee et al., *J. Plant Bioch. and Biotech.* 6, (2):69-73. 1997.
Bower et al., *Plant J.*, 2:409-416. 1992.
Broun et al., *Proc. Natl. Acad. Sci. USA*, 101:4706-4711, 2004.
Buchanan-Wollaston et al., *Plant Cell Reports*, 11:627-631, 1992
Buising and Benbow, *Mol Gen Genet*, 243(1):71-81, 1994.
Callis et al., *Genes Dev.*, 1:1183-1200, 1987.
Casa et al., *Proc. Natl. Acad. Sci. USA*, 90(23):11212-11216, 1993.
Chakravarthy et al., *Plant Cell*, 15:3033-3050, 2003.
Chandler et al., *Plant Cell*, 1:1175-1183, 1989.
Chen et al., *Plant Cell*, 15, 1170-1185, 2003.
Christou; et al., *Proc. Natl. Acad. Sci. USA*, 84(12):3962-3966, 1987.
Chu et al., *Scientia Sinica*, 18:659-668, 1975.
Conkling et al., *Plant Physiol.*, 93:1203-1211, 1990.
DE 3642 829 A
De Block et al., *EMBO J.*, 6(9):2513-2518, 1987.
De Block et al., *Plant Physiol.*, 91:694-701, 1989.
Dellaporta et al., *In: Chromosome Structure and Function: Impact of New Concepts*, 18th Stadler Genetics Symposium, 11:263-282, 1988.
D'Halluin et al., *Plant Cell*, 4(12):1495-1505, 1992.
Dubouzet et al., *Plant J.*, 33, 751-763, 2003.
Ebert et al., *Proc. Natl. Acad. Sci. USA*, 84:5745-5749, 1987.
Fiebig et al., *Plant Cell*, 12:2001-2008, 2000.
Fraley et al., *Bio/Technology*, 3:629-635, 1985.
Fromm et al., *Nature*, 319:791-793, 1986.
Gallie et al., *Plant Cell*, 1:301-311, 1989.
Gelvin et al., *In: Plant Molecular Biology Manual*, 1990.
Ghosh-Biswas et al., *J. Biotechnol.*, 32(1):1-10, 1994.
Gilmour et al., *Plant Physiol.*, 124, 1854-1865, 2000.
Gutterson and Reuber, *Curr. Opin. Plant Biol.*, 7, 465-471, 2004.
Haake et al., *Plant Physiol.*, 130, 639-648, 2002.
Hagio et al., *Plant Cell Rep.*, 10(5):260-264, 1991.
Hamilton et al., *Proc. Natl. Acad. Sci. USA*, 93(18):9975-9979, 1996.
Hannoufa et al., *Plant J*, 10, 459-467, 1996.
Hansen et al., *Plant Physiol.*, 113, 1091-1100, 1997.
Haseloff et al., *Proc. Natl. Acad. Sci. USA*, 94(6):2122-2127, 1997.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218, 1997.
Hinchee et al., *Bio/technol.*, 6:915-922, 1988.
Hooker et al., *Plant Physiol.*, 129, 1568-1580, 2002.

Hou and Lin, *Plant Physiology,* 111:166, 1996.
Hudspeth and Grula, *Plant Mol. Biol.,* 12:579-589, 1989.
Ikuta et al., *Bio/technol.,* 8:241-242, 1990.
Ishidia et al., *Nat. Biotechnol.,* 14(6):745-750, 1996.
Jaglo-Ottosen et al., *Science,* 280, 104-106, 1998.
Jefferson, *Crop Sci.,* 34, 367-371, 1994.
Jenks and Ashworth, In: *Horticultural Reviews,* Janick (Ed.), 1-68. John Wiley & Sons, Inc., NY, 1999.
Jenks et al., *Plant Physiol.,* 108:369-377, 1995.
JenksIn: *The Arabidopsis Book,* Somerville and Meyerowitz (Eds.), American Society of Plant Biologists, Rockville, Md., 2002.
Jofuku et al., *Plant Cell,* 6:1211-1225, 1994.
Kaeppler et al., *Plant Cell Reports,* 9:415-418, 1990.
Kaeppler et al., *Theor. Appl. Genet.,* 84(5-6):560-566, 1992.
Kasuga et al., *Nat. Biotechnol.,* 17:287-291, 1999.
Kasuga et al., *Plant Cell Physiol.,* 45, 346-350, 2004.
Katz et al., *J. Gen. Microbiol.,* 129:2703-2714, 1983.
Kerstiens, *Trends Plant Sci.,* 1, 125-129, 1996.
Klee et al., *Bio-Technology,* 3(7):637-642, 1985.
Knittel et al., *Plant Cell Reports,* 14(2-3):81-86, 1994.
Koorneef et al., *J. Hered.,* 80, 118-122, 1989.
Kunst and Samuels, *Prog. Lipid Res.,* 42, 51-80, 2003.
Lawton et al., *Plant Mol. Biol.* 9:315-324, 1987.
Lazzeri, *Methods Mol. Biol.,* 49:95-106, 1995.
Lee et al., *Korean J. Genet.,* 11(2):65-72, 1989.
Liu et al., *Plant Cell,* 10, 1391-1406, 1998.
Lolle et al., *Dev Biol.,* 189, 311-321, 1997.
Lolle et al., *Dev. Biol.,* 189,311-321, 1997.
Lorz et al., *Mol Gen Genet,* 199:178-182, 1985.
Marcotte et al., *Nature,* 335:454, 1988.
McCabe and Martinell, *Bio-Technology,* 11(5):596-598, 1993.
McCormac et al., *Euphytica,* 99(1):17-25, 1998.
Millar et al., *Plant Cell,* 11, 825-838, 1999.
Moose and Sisco, *Genes Dev.,* 10:3018-3027, 1996.
Murakami et al., *Mol. Gen. Genet.,* 205:42-50, 1986.
Murashige and Skoog, *Physiol. Plant.,* 15:473-497, 1962.
Nagatani et al., *Biotech. Tech.,* 11(7):471-473, 1997.
Negruk et al., *Plant J.,* 9:137-145, 1996.
Novillo et al., *Proc. Natl. Acad. Sci. USA,* 101:3985-3990, 2004.
Odell et al., *Nature,* 313:810-812, 1985.
Ogawa et al., *Sci. Rep.,* 13:42-48, 1973.
Okamuroet al., *Proc. Natl. Acad. Sci. USA,* 94:7076-7081, 1997.
Omirulleh et al., *Plant Mol. Biol.,* 21(3):415-428, 1993.
Onate-Sanchez and Singh, *Plant Physiol.,* 128, 1313-1322, 2002.
Ow et al., *Science,* 234:856-859, 1986.
PCT App. WO 9217598
PCT App. WO 94/09699
PCT App. WO 95/06128
PCT App. WO 97/4103
PCT App. WO 97/41228
Post-Beittenmiller, *Annu. Rev. Plant Physiol. Plant Mol. Biol.,* 47, 405-430, 1996.
Potrykus et al., *Mol. Gen. Genet.,* 199:183-188, 1985.
Prasher et al., *Biochem. Biophys. Res. Commun.,* 126(3): 1259-1268, 1985.
Pruitt et al., *Proc. Natl. Acad. Sci. USA,* 97:1311-1316, 2000.
Quackenbush et al., *Nucl. Acids. Res.,* 28, 141-145, 2000.
Rawson and Clarke, *Aust. J. Plant Physiol.,* 15, 397-406, 1988.
Reichel et al., *Proc. Natl. Acad. Sci. USA,* 93 (12) p. 5888-5893. 1996.
Rhodes et al., *Methods Mol. Biol.,* 55:121-131, 1995.
Riechmann et al., *Science,* 290, 2105-2110, 2000.
Ritala et al., *Plant Mol. Biol.,* 24(2):317-325, 1994.
Rogers et al., *Methods Enzymol.,* 153:253-277, 1987.
Sakuma et al., *Biochem. Biophys. Res. Comm.,* 290:998-1009, 2002.
Sambrook et al., *In: Molecular Cloning—A Laboratory Manual* (second edition), Cold Spring Harbour Laboratory Press, 1989.
Schultz and Haughn, *Plant Cell,* 3:771-781, 1991.
Sheen et al., *Plant Journal,* 8(5):777-784, 1995.
Shinozaki et al., *Curr. Opin. Plant Biol.,* 6:410-417, 2003.
Singsit et al., *Transgenic Res.,* 6(2):169-176, 1997.
Spencer et al., *Plant Molecular Biology,* 18:201-210, 1992.
Stalker et al., *Science,* 242:419-422, 1988.
Stockinger et al., *Proc. Natl. Acad. Sci. USA,* 94:1035-1040, 1997.
St-Pierre et al., *Plant J.,* 14:703-713, 1998.
Sullivan et al., *Mol. Gen. Genet.,* 215(3):431-440, 1989.
Sutcliffe, *Proc. Natl. Acad. Sci. USA,* 75:3737-3741, 1978.
Tacke et al., *Plant J.,* 8:907-917, 1995.
Thillet et al., *J. Biol. Chem.,* 263:12500-12508, 1988.
Thomas et al., *Plant Sci.* 69:189-198, 1990.
Thomashow, *Annu. Rev. Plant Physiol. Plant Mol. Biol.,* 50, 571-599, 1999.
Thompson et al., *EMBO J.,* 6(9):2519-2523, 1987.
Thompson et al., *Euphytica,* 85(1-3):75-80, 1995.
Thompson et al., *Nucl. Acids. Res.,* 22:4673-4680, 1994.
Tian et al., *Plant Cell Rep.,* 16:267-271, 1997.
Tingay et al., *Plant J.,* 11(6):1369-1376. 1997.
Todd et al., *Plant J.,* 17:119-130, 1999.
Tomes et al., *Plant. Mol. Biol.* 14(2):261-268, 1990.
Torbet et al., *Crop Science,* 38(1):226-231, 1998.
Torbet et al., *Plant Cell Reports,* 14(10):635-640, 1995.
Toriyama et al., *Theor Appl. Genet.,* 73:16, 1986.
Tsuchiya et al., *J. Bacteriol.,* 171:3187-3191, 1989.
Tsukada et al., *Plant Cell Physiol.,* 30(4)599-604, 1989.
Uchimiya et al., *Mol. Gen. Genet.,* 204:204, 1986.
Van Eck et al., *Plant Cell Reports,* 14(5):299-304, 1995.
Vasil et al., *Plant Physiol.,* 91:1575-1579, 1989.
Vogg et al., *J. Exp. Bot.,* 149, 2004.
Walker et al., *Proc. Natl. Acad. Sci. USA,* 84:6624-6628, 1987.
Wang et al., *Molecular Cell. Biol.,* 12(8):3399-3406, 1992.
Wei et al., *Plant Physiol. Biochem.,* 39, 841-848, 2001.
Wellesen et al., *Proc. Natl. Acad. Sci. USA,* 98:9694-9699, 2001.
Xia et al., *Plant Cell,* 8, 1291-1304, 1996.
Xia et al., *Plant Physiol.,* 115, 925-937, 1997.
Xu et al., *Plant Physiol.,* 115, 501-510, 1997.
Yamada et al., *Plant Cell Rep.,* 4:85, 1986.
Yang and Russell, *Proc. Natl. Acad. Sci. USA,* 87:4144-4148, 1990.
Zhang, *Curr. Opin. Plant Biol.,* 6, 430-440, 2003.
Zheng and Edwards, *J. Gen. Virol.,* 71:1865-1868, 1990.
Zhou et al., *Plant Cell Reports,* 12(11).612-616, 1993.
Zukowsky et al., Proc. Natl. Acad. Sci. USA, 80:1101-1105, 1983.

The invention claimed is:

1. An isolated nucleic acid selected from the group consisting of: (a) a nucleic acid encoding the polypeptide of SEQ ID NO:1; b) a nucleic acid comprising the sequence of SEQ ID NO:2; (c) a nucleic acid sequence encoding a polypeptide with at least 95% amino acid identity to SEQ ID NO:1 that activates wax biosynthesis in a plant cell; (d) the complement of a sequence of (a) or (b).

2. The isolated nucleic acid of claim 1, wherein the nucleic acid sequence is operably linked to a heterologous promoter.

3. A recombinant vector comprising the isolated nucleic acid of claim 2.

4. The recombinant vector of claim 3, further comprising at least one additional sequence chosen from the group consisting of: a regulatory sequence, a selectable marker, a leader sequence and a terminator.

5. The recombinant vector of claim 4, wherein the additional sequence is a heterologous sequence.

6. The recombinant vector of claim 3, wherein the heterologous promoter is a plant developmentally-regulated, organelle-specific, inducible, tissue-specific, constitutive, cell-specific, seed specific, or germination-specific promoter.

7. The recombinant vector of claim 3, wherein the heterologous promoter is a drought-inducible promoter.

8. The recombinant vector of claim 3, defined as an isolated expression cassette.

9. A transgenic plant transformed with a selected DNA comprising the nucleic acid of claim 1.

10. The transgenic plant of claim 9, further defined as a dicotyledonous plant.

11. The transgenic plant of claim 9, further defined as a monocotyledonous plant.

12. The transgenic plant of claim 9, further defined as an $R_0$ transgenic plant.

13. The transgenic plant of claim 9, further defined as a progeny plant of any generation of an $R_0$ transgenic plant, wherein the transgenic plant comprises the selected DNA.

14. A seed of the transgenic plant of claim 9, wherein the seed comprises the selected DNA.

15. A bacterial or plant host cell transformed with a selected DNA comprising the nucleic acid of claim 1.

16. The host cell of claim 15, wherein the host cell expresses a protein encoded by the selected DNA.

17. The host cell of claim 15, wherein the host cell is a plant cell.

* * * * *

UNITED STATES PATENT AND TRADEMARK OFFICE
CERTIFICATE OF CORRECTION

| | | |
|---|---|---|
| PATENT NO. | : 7,253,342 B2 | Page 1 of 1 |
| APPLICATION NO. | : 11/253300 | |
| DATED | : August 7, 2007 | |
| INVENTOR(S) | : Zhang et al. | |

It is certified that error appears in the above-identified patent and that said Letters Patent is hereby corrected as shown below:

On the title page under item (75), INVENTORS, on line 1 please delete "US" and insert --PRC--.

On the title page under item (75), INVENTORS, on line 2 please delete "US" and insert --PRC--.

Signed and Sealed this

Twenty-ninth Day of April, 2008

JON W. DUDAS
*Director of the United States Patent and Trademark Office*